(12) United States Patent
Wu et al.

(10) Patent No.: US 6,777,543 B2
(45) Date of Patent: Aug. 17, 2004

(54) 13-METHYL ERYTHROMYCIN DERIVATIVES

(75) Inventors: Yong-Jin Wu, Madison, CT (US); Wei-Guo Su, East Lyme, CT (US); Takushi Kaneko, Guilford, CT (US); Hamish McArthur, Mystic, CT (US)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 10/441,347

(22) Filed: May 19, 2003

(65) Prior Publication Data

US 2003/0229031 A1 Dec. 11, 2003

Related U.S. Application Data

(63) Continuation of application No. 09/577,901, filed on May 24, 2000, now abandoned.
(60) Provisional application No. 60/135,468, filed on May 24, 1999.

(51) Int. Cl.$^7$ .............................................. C07H 17/08
(52) U.S. Cl. ........................ 536/7.4; 536/7.2; 536/7.3
(58) Field of Search ............................ 536/7.2, 7.3, 7.4; 519/29

(56) References Cited

U.S. PATENT DOCUMENTS

| | | | |
|---|---|---|---|
| 3,923,784 A | 12/1975 | Kierstead et al. ............ 260/210 |
| 4,328,334 A | 5/1982 | Kobrehel et al. ............. 536/7.4 |
| 4,331,803 A | 5/1982 | Watanabe et al. ............. 536/7.2 |
| 4,474,768 A | 10/1984 | Bright ......................... 424/180 |
| 4,517,359 A | 5/1985 | Kobrehel et al. ............. 536/7.4 |
| 4,668,776 A | 5/1987 | Yamada et al. ............... 536/7.4 |
| 4,672,056 A | 6/1987 | Fernandes et al. ............ 514/29 |
| 4,680,386 A | 7/1987 | Morimoto et al. ............ 536/7.4 |
| 4,826,820 A | 5/1989 | Brain ........................... 514/29 |
| 4,886,792 A | 12/1989 | Djokic et al. ................ 514/183 |
| 5,141,926 A | 8/1992 | Weber et al. ................. 514/29 |
| 5,332,807 A | 7/1994 | Waddell et al. ............... 536/7.4 |
| 5,414,926 A | 5/1995 | Ito et al. ........................ 29/753 |
| 5,439,889 A | 8/1995 | Agouridas et al. ............. 514/29 |
| 5,441,939 A | * 8/1995 | Yang ............................ 514/29 |
| 5,444,051 A | 8/1995 | Agouridas et al. ............. 514/29 |
| 5,523,399 A | 6/1996 | Asaka et al. ................... 536/7.3 |
| 5,527,780 A | 6/1996 | Agouridas et al. ............. 514/29 |
| 5,543,400 A | 8/1996 | Agouridas et al. ............. 514/29 |
| 5,561,118 A | 10/1996 | Agouridas et al. ............. 514/29 |
| 5,614,614 A | 3/1997 | Agouridas et al. ............. 536/7.5 |
| 5,629,296 A | 5/1997 | Kujundzic et al. ............. 514/29 |
| 5,635,485 A | 6/1997 | Agouridas et al. ............. 514/29 |
| 5,656,607 A | 8/1997 | Agouridas et al. ............. 514/29 |
| 5,747,466 A | 5/1998 | Elliott et al. ................... 514/29 |
| 5,747,467 A | 5/1998 | Agouridas et al. ............. 514/29 |
| 5,750,510 A | * 5/1998 | Elliott et al. ................... 514/29 |
| 5,760,233 A | 6/1998 | Agouridas et al. ........... 546/152 |
| 5,786,339 A | 7/1998 | Agouridas et al. ............ 519/30 |
| 5,824,513 A | 10/1998 | Katz et al. ..................... 435/76 |
| 5,866,549 A | * 2/1999 | Or et al. ........................ 514/29 |
| 5,985,844 A | 11/1999 | Heck et al. .................... 514/29 |
| 6,022,965 A | 2/2000 | Benedetti et al. ............ 536/125 |
| 6,025,350 A | 2/2000 | Masamune et al. .......... 514/183 |
| 6,043,226 A | * 3/2000 | Lundy et al. ................... 514/29 |
| 6,043,227 A | 3/2000 | Cheng et al. .................. 514/29 |
| 6,077,943 A | * 6/2000 | Omura et al. ................. 536/7.2 |
| 6,096,714 A | 8/2000 | Agouridas et al. ............. 514/29 |
| 6,100,240 A | 8/2000 | Cheng et al. .................. 514/29 |
| 6,121,432 A | 9/2000 | Bonnet et al. ................ 536/7.2 |
| 6,159,945 A | 12/2000 | Wu .............................. 514/29 |
| 6,162,793 A | 12/2000 | Agouridas et al. ............ 514/29 |
| 6,162,794 A | 12/2000 | Wu .............................. 514/29 |
| 6,165,986 A | 12/2000 | Asaka et al. ................... 514/29 |

(List continued on next page.)

FOREIGN PATENT DOCUMENTS

| | | | |
|---|---|---|---|
| CA | 2126665 | 7/1993 | ........... C07H/17/08 |
| CL | 40416 | 4/1995 | |
| EP | 1146051 | 10/1971 | ........... C07H/17/08 |
| EP | 0508699 | 3/1998 | ........... C07H/17/08 |
| EP | 0716093 | 10/1998 | ........... C07H/17/08 |
| EP | 0895999 | 2/1999 | ........... C07H/17/08 |
| EP | 0949268 | 10/1999 | ........... C07H/17/08 |
| EP | 1044985 | 10/2000 | ........... C07H/17/08 |
| EP | 1114826 | 7/2001 | ........... C07H/17/08 |
| EP | 1122261 | 8/2001 | ........... C07H/17/02 |
| EP | 1167376 | 1/2002 | ........... C07H/17/08 |
| EP | 1026170 | 1/2003 | ........... C07H/17/08 |
| EP | 1004592 | 7/2003 | ........... C07H/17/08 |
| FR | 2691464 | 5/1992 | ........... C07H/17/08 |

(List continued on next page.)

Primary Examiner—Elli Peselev
(74) Attorney, Agent, or Firm—Peter C. Richardson; Gregg C. Benson; Frank W. Forman

(57) ABSTRACT

The invention relates to compounds of the formula

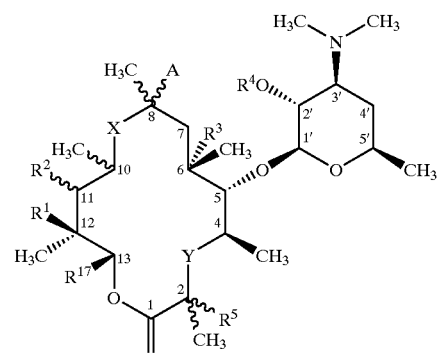

and to pharmaceutically acceptable salts, prodrugs and solvates thereof, wherein $R^1$, $R^2$, $R^3$, $R^4$, $R^5$, $R^{17}$, $R^j$, A, X, and Y are as defined herein. The invention also relates to pharmaceutical compositions containing the compounds of formulas 1, methods of using the compounds of formula 1 in the treatment of infections and methods of preparing the compounds of formula 1.

5 Claims, No Drawings

U.S. PATENT DOCUMENTS

| | | |
|---|---|---|
| 6,191,118 B1 | 2/2001 | Asaka et al. .................. 514/29 |
| 6,248,719 B1 | 6/2001 | Wu .............................. 514/29 |
| 6,271,255 B1 | 8/2001 | Leadlay et al. ............. 514/450 |
| 6,274,715 B1 | 8/2001 | Or et al. ...................... 536/7.4 |
| 6,291,656 B1 | 9/2001 | Wu .............................. 536/7.4 |
| 6,300,316 B1 | 10/2001 | Brighty et al. ................ 514/29 |
| 6,313,101 B1 | 11/2001 | Denis et al. ................... 514/29 |
| 6,329,345 B1 | 12/2001 | Rafka et al. .................. 514/28 |
| 6,355,620 B1 | 3/2002 | Ma et al. ...................... 514/29 |
| 6,399,582 B1 | 6/2002 | Hlasta et al. ................. 514/29 |
| 6,407,074 B1 | 6/2002 | Bronk et al. .................. 514/29 |
| 6,420,343 B1 | 7/2002 | Su et al. ....................... 514/29 |
| 6,420,536 B1 | 7/2002 | Bronk et al. .................. 536/7.4 |
| 6,472,371 B1 | 10/2002 | Dirlam et al. ................ 514/29 |
| 6,576,749 B2 | 6/2003 | Bronk et al. .................. 536/7.4 |
| 2002/0013281 A1 | 1/2002 | Agouridas et al. ............ 514/29 |
| 2002/0025937 A1 | 2/2002 | Wu .............................. 514/29 |
| 2002/0040007 A1 | 4/2002 | Kaneko ........................ 514/28 |
| 2002/0052328 A1 | 5/2002 | Kaneko et al. ............... 514/29 |
| 2002/0061856 A1 | 5/2002 | Wu .............................. 514/29 |
| 2002/0061857 A1 | 5/2002 | Wu .............................. 514/29 |
| 2002/0061858 A1 | 5/2002 | Bronk et al. .................. 514/29 |
| 2002/0077302 A1 | 6/2002 | Wu .............................. 514/29 |
| 2002/0111317 A1 | 8/2002 | Katz et al. ..................... 514/28 |
| 2002/0115621 A1 | 8/2002 | Su et al. ....................... 514/29 |
| 2002/0156027 A1 | 10/2002 | McMillen et al. ............ 514/29 |
| 2003/0013662 A1 | 1/2003 | Katz et al. ..................... 514/28 |
| 2003/0013665 A1 | 1/2003 | Kaneko ........................ 514/29 |
| 2003/0050254 A1 | 3/2003 | Denis ........................... 514/29 |
| 2003/0100518 A1 | 5/2003 | Wu et al. ...................... 514/29 |
| 2003/0100742 A1 | 5/2003 | Kaneko et al. ............... 536/7.4 |

FOREIGN PATENT DOCUMENTS

| | | | |
|---|---|---|---|
| FR | 2732023 | 3/1995 | ........... C07H/17/08 |
| FR | 2732684 | 4/1995 | ........... C07H/17/08 |
| FR | 2754821 | 10/1996 | ........... C07H/17/08 |
| WO | WO9313116 | 7/1993 | ........... C07H/17/08 |
| WO | WO9736912 | 10/1997 | ........... C07H/17/08 |
| WO | WO9800741 | 1/1998 | ............ G02B/6/38 |
| WO | WO9801546 | 1/1998 | ........... C12N/15/00 |
| WO | WO9801571 | 1/1998 | ........... C12N/15/62 |
| WO | WO9803530 | 1/1998 | ........... C07H/17/08 |
| WO | WO9813373 | 4/1998 | ........... C07H/17/08 |
| WO | WO9823628 | 6/1998 | ........... C07H/17/08 |
| WO | WO9825942 | 6/1998 | ........... C07H/17/08 |
| WO | WO9838199 | 9/1998 | ........... C07H/17/08 |
| WO | WO9851696 | 11/1998 | ........... C07H/17/08 |
| WO | WO9856800 | 12/1998 | ........... C07H/17/08 |
| WO | WO9856801 | 12/1998 | ........... C07H/17/08 |
| WO | WO9856802 | 12/1998 | ........... C07H/17/08 |
| WO | WO9900124 | 1/1999 | ........... A61K/31/33 |
| WO | WO9911651 | 3/1999 | ........... C07H/17/00 |
| WO | WO9912552 | 3/1999 | ........... A61K/31/70 |
| WO | WO9921865 | 5/1999 | ........... C07H/17/08 |
| WO | WO9921866 | 5/1999 | ........... C07H/17/08 |
| WO | WO9921869 | 5/1999 | ........... C07H/17/08 |
| WO | WO9925365 | 5/1999 | ........... A61K/31/70 |
| WO | WO9929709 | 6/1999 | ........... C07H/17/08 |
| WO | WO9935156 | 7/1999 | ........... C07H/17/08 |
| WO | WO9935157 | 7/1999 | ........... C07H/17/08 |
| WO | WO9962920 | 12/1999 | ........... C07H/17/08 |
| WO | WO0000500 | 1/2000 | ........... C07H/17/08 |
| WO | WO0000618 | 1/2000 | ........... C12N/15/52 |
| WO | WO0063225 | 10/2000 | ........... C07H/17/08 |
| WO | WO0071557 | 11/2000 | ........... C07H/17/08 |

\* cited by examiner

13-METHYL ERYTHROMYCIN DERIVATIVES

This is a continuation application based upon and claiming priority from U.S. patent application No. 09/577,901, filed May 24, 2000, now abandoned, which is based upon U.S. provisional patent application 60/135,468, filed May 24, 1999.

BACKGROUND OF THE INVENTION

This invention relates to novel macrolide compounds that are useful as antibacterial and antiprotozoal agents in mammals, including man, as well as in fish and birds. This invention also relates to methods of preparing the novel compounds and pharmaceutical compositions containing the novel compounds. In addition, the present invention includes methods of treating bacterial and protozoal infections through the administration of the novel compounds to mammals, fish and birds requiring such treatment.

Although some 13-methyl erythromycins (also known as 15-norerythromycins) have been reported previously (Kibwage et al., *J. Antibiotics*, vol. 40, pp. 1–6, (1987); Weber & McAlpine, U.S. Pat. No. 5,141,926), these have been confined to 15-norerythromycin C and 6-deoxy-15-norerythromycins B and D. Moreover, not only have these 15-norerythromycins been found as extremely minor components co-expressed with high levels of "natural" erythromycins (13-ethyl erythromycins), but the 13-methyl counterparts (15-norerythromycins A and B) to the most desirable and biologically-active "natural" erythromycins (erythromycin A and B) have never previously been isolated.

Chemical modification of "natural" erythromycins has proven to be an extremely effective means for enhancing the bioefficacy of the "natural" molecules. Thus, one would expect chemical modification of novel erythromycins to similarly produce compounds with desirable and enhanced bioefficacies. International Patent Application WO 98/01546, PUBLISHED Jan. 15, 1998, filed Jul. 4, 1997, describes in general terms the production of novel polyketides through recombinant DNA technologies. The use of these technologies to generate novel erythromycins, many of which have starter units different from the propionate starter unit characteristic of the "natural" erythromycins, is described in pending International Patent Application WO 98/01571, PUBLISHED Jan. 15, 1998, filed Jul. 4, 1997. Chemical modification of these novel erythromycins is also described in co-pending International Patent Applications WO 99/35156, PUBLISHED Jul. 15, 1999, filed Dec. 21, 1998, and WO 99/35157, published Jul. 15, 1999.

Macrolide antibiotics are known to be useful in the treatment of a broad spectrum of bacterial and protozoal infections in mammals (including humans), fish and birds. Various derivatives of erythromycin A that are useful as antibiotic agents are referred to in U.S. patent application serial No. 60/049,349, filed Jun. 11, 1997; U.S. patent application serial No. 60/046,150, filed May 9, 1997; U.S. patent application serial No. 60/063,676, filed Oct. 29, 1997; U.S. patent application serial No. 60/087,798, filed Jun. 3, 1998; U.S. patent application serial No. 60/054,866, filed Aug. 6, 1997; U.S. patent application serial No. 60/063,161, filed Oct. 29, 1997; U.S. patent application serial No. 60/117,342, filed Jan. 27, 1999; U.S. patent application serial No. 60/130,809, filed Apr. 23, 1999; U.S. patent application serial No. 60/130,912, filed Apr. 23, 1999; and U.S. patent application serial No. 60/130,913, filed Apr. 23, 1999. Each of the foregoing U.S. patent applications is incorporated herein by reference in its entirety. Like other macrolide antibiotics, the novel erythromycin derivatives of the present invention possess activity against infections caused by various gram-positive and gram-negative bacteria as well as protozoa, as described below.

SUMMARY OF THE INVENTION

The present invention relates to novel derivatives of erythromycin that are useful as antibacterial and antiprotozoal agents in mammals (including humans), fish and birds. In particular, the compounds of the present invention include novel 13-methyl erythromycin derivatives prepared by chemical modification of 13-methyl erythromycins, which have been produced by direct fermentation. The invention further relates to methods for preparing the claimed compounds, pharmaceutical compositions containing such compounds and methods of treatment with such compounds and compositions.

In particular, the present invention relates to compounds of formula 1:

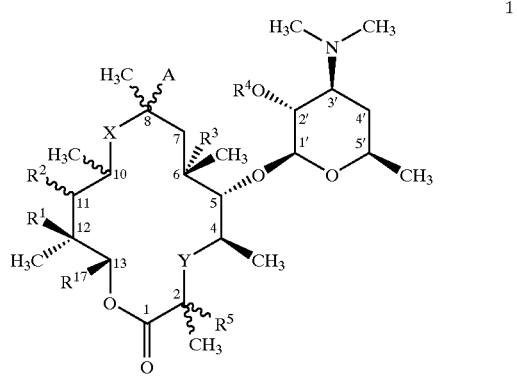

and to pharmaceutically acceptable salts, prodrugs and solvates thereof, wherein:

A is H or halogen;

X is selected from —C(O)—, —CH(NR$^8$R$^9$)—, —CHR$^8$NR$^9$—, —NR$^9$CHR$^8$—, —C(=NR$^8$)— and —C(=N—OR$^8$)—, wherein the first dash of each of the foregoing X groups is attached to the C-10 carbon of the compound of formula 1 and the last dash of each group is attached to the C-8 carbon of the compound of formula 1;

Y is selected from CH$_2$, C(O), CHF, CF$_2$, C=C(R$^a$R$^b$), CHSR$^7$, CHR$^7$, C=S, —C(=NR$^8$)—, —C(=N—OR$^8$), CH(OR$^8$), CH(OC(O)R$^8$), CH(OC(O)Ar), CH(OC(O)NR$^8$R$^9$), CH(O(CR$^a$R$^b$)$_n$Ar), CH(OC(O)(CR$^a$R$^b$)$_n$Ar), CH(OC(O)(CR$^a$R$^b$)$_n$NR$^8$(CR$^a$R$^b$)$_n$Ar), CH(OC(O)NR$^8$NR$^8$R$^9$), CH(OC(O)NR$^8$(CR$^a$R$^b$)$_n$NR$^8$(CR$^a$R$^b$)$_n$Ar), CH(OC(O)NR$^8$NR$^8$(CR$^a$R$^b$)$_n$NR$_8$(CR$^a$R$^b$)$_n$Ar), —CH(NR$^8$R$^9$)—, CH(NR$^8$C(O)R$^8$), CH(NR$^8$C(O)NR$^8$R$^9$), CH(NR$^8$C(O)OR$^8$), CH(S(CR$^a$R$^b$)$_n$Ar), —CH(NH(CR$^a$R$^b$)$_n$NR$^8$(CR$^a$R$^b$)$_n$Ar) and CH(NH(CR$^a$R$^b$)$_n$Ar), wherein n is an integer ranging from 0 to 10;

or Y has the following structure:

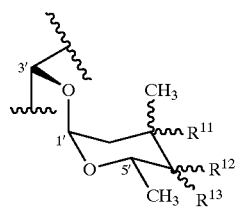

R¹ and R² can be taken separately or together;

when taken separately, R¹ is independently selected from $OR^8$, $OC(O)R^8$, $OC(O)NR^8R^9$, $NR^8R^9$, $NR^8C(O)R^8$, $NR^8C(O)NR^8R^9$, $O(CR^aR^b)_nAr$, $S(CR^aR^b)_nAr$ and $N(CR^aR^b)_nAr$, wherein n is an integer ranging from 0 to 10;

when taken separately, R² is independently selected from $OR^8$, O-mesyl, O-tosyl, $OC(O)R^8$, $OC(O)NR^8R^9$, $NR^8R^9$, $NR^8C(O)R^8$, $NR^8C(O)NR^8R^9$, $O(CR^aR^b)_nAr$, $S(CR^aR^b)_nAr$ and $NH(CR^aR^b)_nAr$, wherein n is an integer ranging from 0 to 10;

each of $R^a$ and $R^b$ is independently selected from H, halo and a $C_1$–$C_6$ alkyl;

$R^a$ and $R^b$ together with the carbon to which they are attached can form a 3- to 10-membered cyclic or heterocyclic diradical, wherein one or two carbons of said diradical are optionally replaced by a diradical independently selected from —O—, —S—, —S(O)—, —S(O)$_2$—, a —N(C$_1$–C$_6$)alkyl- and —C(O)— and are optionally substituted by 1 to 3 substituents independently selected from the group S substituents;

$(CR^aR^b)_n$ is alkylene, wherein n is an integer ranging from 0 to 10, uninterrupted or interrupted by a diradical independently selected from —O—, —S—, —S(O)—, —S(O)$_2$—, a —N(C$_1$–C$_6$)alkyl- and —C(O)— and optionally substituted by 1 to 3 substituents independently selected from the group S substituents;

when taken together, R¹ and R² taken with the intervening atoms form an additional ring having one of the following structures:

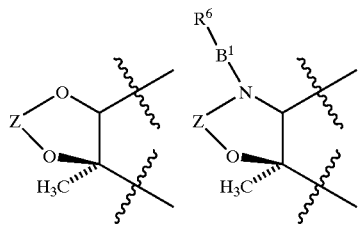

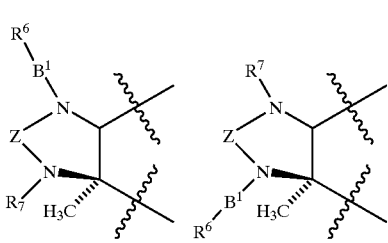

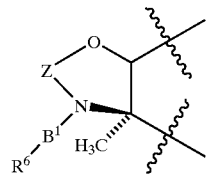

$B^1$ is selected from O, $(CR^{aa}R^{bb})_m$, $SO_2$, O and $NR^7$, wherein m is 0 or 1;

Z is selected from $(CR^{aa}R^{bb})_m$, C(O), C($NR^{aa}$), P—$OR^{aa}$, P(O)$OR^{aa}$, P(O)$NR^{aa}R^{bb}$, Si($R^cR^d$), SO, $SO_2$, $(CR^{aa}R^{bb})_m$CO and CO$(CR^{aa}R^{bb})_m$, wherein m is 1 or 2;

$R^c$ and $R^d$ are independently selected from a $C_1$–$C_8$ alkyl, a $C_6$–$C_{10}$ aryl and a $C_4$–$C_{10}$ heterocyclic;

$R^{aa}$ and $R^{bb}$ are independently selected from H and a $C_1$–$C_6$ alkyl;

$R^{aa}$ and $R^{bb}$ together with the carbon to which they are attached can form a 3- to 10-membered cyclic or heterocyclic diradical, wherein one or two carbons of said diradical are optionally replaced by a diradical independently selected from —O—, —S—, —S(O)—, —S(O)$_2$—, a —N(C$_1$–C$_6$) alkyl- and —C(O)— and are optionally substituted by 1 to 3 substituents independently selected from the group S substituents;

when $B^1$ is $NR^7$, $B^1$ and $R^6$ together with the nitrogen to which they are attached can form a 3- to 10-membered ring wherein one or two carbons of said ring are optionally replaced by a diradical independently selected from —O—, —S—, —S(O)—, —S(O)$_2$—, a —N(C$_1$–C$_6$) alkyl- and —C(O)— and are optionally substituted by 1 to 3 substituents independently selected from the group S substituents;

when $B^1$ is $NR^7$, $B^1$ and $R^6$ together with the nitrogen to which they are attached can form —N=C($R^7$)($R^aR^b$)$_n$ Ar, wherein n is an integer ranging from 0 to 10;

R¹, R² and X can be taken together;

when taken together, R¹, R² and X taken with the intervening atoms form an additional two rings having one of the following structures:

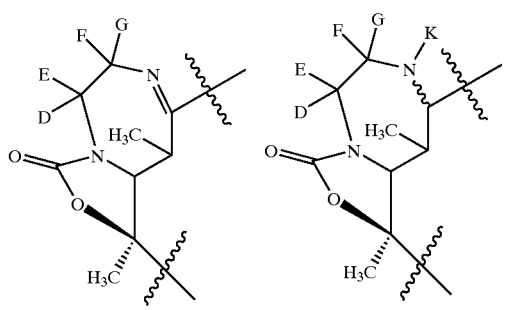

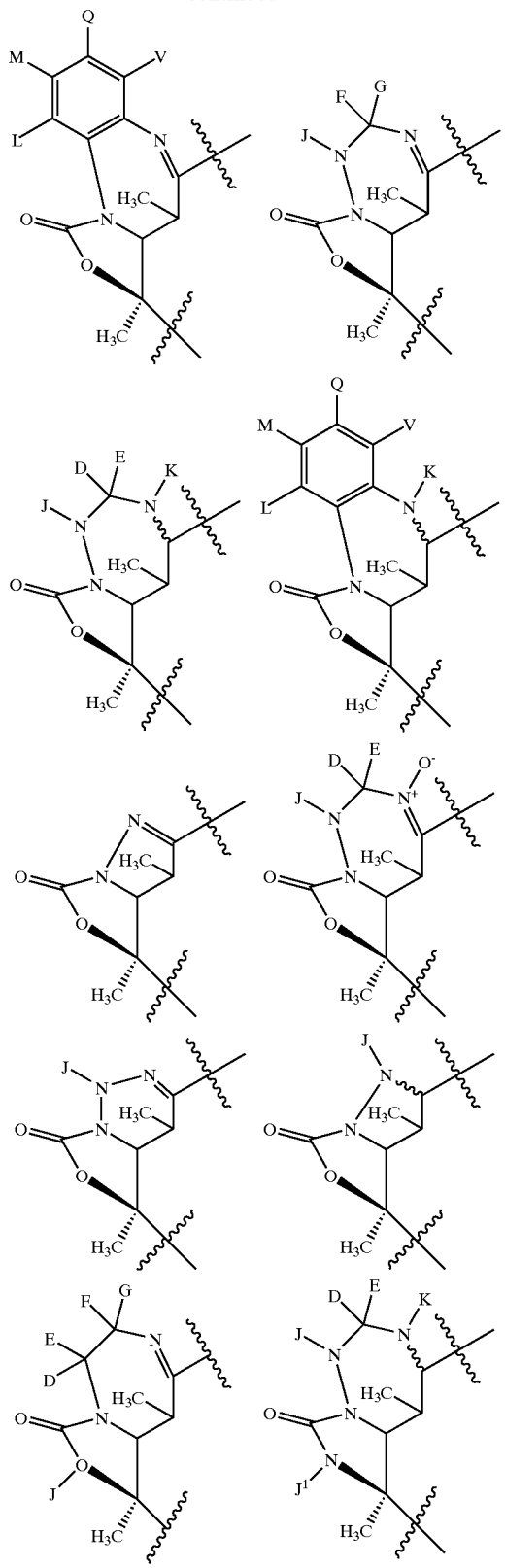

-continued each of D, E, F and G is independently selected from H, halo, a $C_1$–$C_{12}$ alkyl, a $C_3$–$C_{10}$ alkenyl, a $C_3$–$C_{10}$ alkynyl and $CH_2(R^aR^b)_nAr$, wherein n is an integer ranging from 0 to 10, wherein one or two carbons of said alkyl are optionally replaced by a diradical independently selected from —O—, —S—, —S(O)—, —S(O)$_2$—, a —N($C_1$-$C_6$)alkyl- and —C(O)— and are optionally substituted by 1 to 3 substituents independently selected from the group S substituents;

D and E or F and G together with the carbon to which they are attached can form a 3- to 10-membered cyclic or heterocyclic diradical, wherein one or two carbons of said diradical are optionally replaced by a diradical independently selected from —O—, —S—, —S(O)—, —S(O)$_2$—, a —N($C_1$-$C_6$)alkyl- and —C(O)— and are optionally substituted by 1 to 3 substituents independently selected from the group S substituents;

each of J, $J^1$ and K is independently selected from $C(O)R^8$, $C(O)NR^8R^9$, $C(O)OR^8$, $(CR^aR^b)_nAr$, $S(CR^aR^b)_nAr$ and $NH(CR^aR^b)_nAr$; wherein n is an integer ranging from 0 to 10;

each of L, M, Q and V is independently selected from the group S substituents;

one or two carbons of the phenyl ring in which L, M, Q and V are attached can be replaced with nitrogen;

$R^1$ and X can be taken together;

when taken together, $R^2$ and X taken with the intervening atoms form an additional ring having one of the following structures:

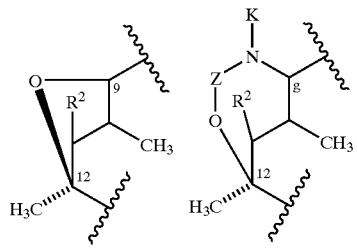

$R^2$ and X can be taken together;

when taken together, $R^2$ and X taken with the intervening atoms form an additional ring having one of the following structures:

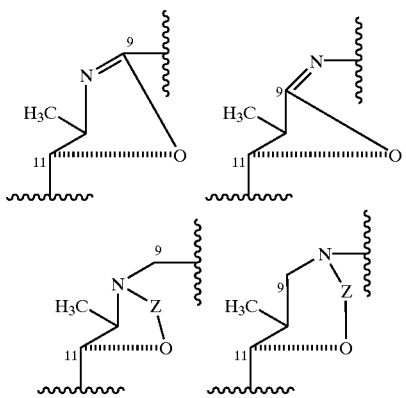

$R^3$ is $OR^{10}$;

$R^3$ and X can be taken together;

when taken together, $R^3$ and X taken with the intervening atoms form an additional ring having one of the following structures:

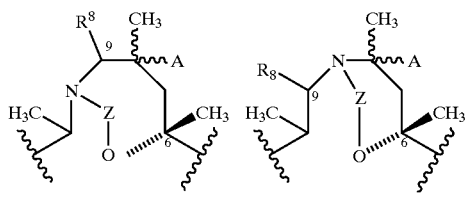

R³ and Y can be taken together;

when taken together, R³ and Y taken with the intervening atoms form an additional ring having one of the following structures:

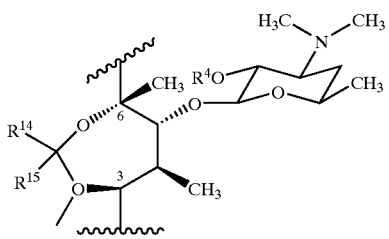

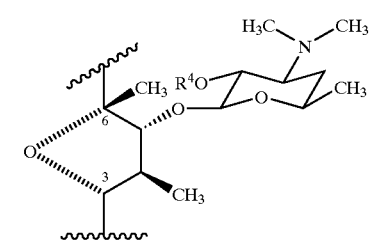

R⁴ is selected from H, a C(O)(C₁–C₁₈)alkyl, C(O)Ar, a OC(O)(C₁–C₁₈)alkyl and OC(O)Ar, wherein the alkyl moieties of the foregoing R⁴ groups are optionally replaced by a diradical independently selected from —O—, —S—, —S(O)—, —S(O)₂—, a —N(C₁–C₆)alkyl- and —C(O)— and are optionally substituted by 1 to 3 substituents independently selected from the group S substituents;

R⁵ is selected from H, halo, a C₁–C₁₀ alkyl, a C₃–C₁₀ alkenyl, a C₃–C₁₀ alkynyl, —C(RᵃRᵇ)— C(Rᵃ)=C(Rᵇ)—Ar, (CRᵃRᵇ)ₙAr, OR⁸, O(CO)R⁸, OC(O)NR⁸R⁹, NR⁸R⁹, NR⁸C(O)R⁸, NR⁸C(O)NR⁸R⁹, O(CRᵃRᵇ)ₙAr, S(CRᵃRᵇ)ₙAr and NR⁸(CRᵃRᵇ)ₙAr, wherein n is an integer ranging from 0 to 10, wherein one or two carbons of said alkyl, alkenyl and alkynyl are optionally replaced by a diradical independently selected from —O—, —S—, —S(O)—, —S(O)₂—, a —N(C₁–C₆)alkyl- and —C(O)— and are optionally substituted by 1 to 3 substituents independently selected from the group S substituents;

R⁵ and Y can be taken together;

when taken together, R⁵ and Y taken with the intervening atoms form the following structure:

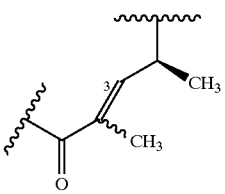

R⁶ is selected from H, a C₁–C₁₂ alkyl, a C₃–C₁₀ alkenyl, a C₃–C₁₀ alkynyl and CH₂(RᵃRᵇ)ₙAr, wherein n is an integer ranging from 0 to 10, wherein one or two carbons of said alkyl are optionally replaced by a diradical independently selected from —O—, —S—, —S(O)—, —S(O)₂—, a —N(C₁–C₆)alkyl- and —C(O)— and are optionally substituted by 1 to 3 substituents independently selected from the group S substituents;

each of R⁷, R⁸ and R⁹ is independently selected from H and a C₁–C₁₂ alkyl, wherein one or two carbons of said alkyl are optionally replaced by a diradical independently selected from —O—, —S—, —S(O)—, —S(O)₂—, a —N(C₁–C₆) alkyl- and —C(O)— and are optionally substituted by 1 to 3 substituents independently selected from the group S substituents;

R⁸ and R⁹ together with the nitrogen to which they are attached can form a 3- to 10-membered ring, in which one or two carbons are optionally replaced by a diradical independently selected from —O—, —S—, —S(O)—, —S(O)₂—, a —N(C₁–C₆) alkyl- and —C(O)— and are optionally substituted by 1 to 3 substituents independently selected from the group S substituents;

R¹⁰ is selected from a C₁–C₁₀ alkyl, a C₃–C₁₀ alkenyl, a C₃–C₁₀ alkynyl, —C(RᵃRᵇ)— C(Rᵃ)=C(Rᵇ)—Ar and (CRᵃRᵇ)ₙAr, wherein n is an integer ranging from 1 to 10, wherein one or two carbons of said alkyl, alkenyl and alkynyl are optionally replaced by a diradical independently selected from —O—, —S—, —S(O)—, —S(O)₂—, a —N(C₁–C₆)alkyl- and —C(O)— and are optionally substituted by 1 to 3 substituents independently selected from the group S substituents, provided that R¹⁰ is not unsubstituted methyl;

R¹¹ is H or OCH₃;

R¹² and R¹³ together with the carbon to which they are attached can form —C(O)—, —C(=NR⁸)— or —C(=N—OR⁸);

R¹² and R¹³ together with the carbon to which they are attached can form a 3- to 10-membered ring, wherein one or two carbons of said ring are optionally replaced by a diradical independently selected from —O—, —S—, —S(O)—, —S(O)₂—, a —N(C₁–C₆) alkyl- and —C(O)— and are optionally substituted by 1 to 3 substituents independently selected from the group S substituents;

R¹² is selected from H, a C₁–C₁₀ alkyl, a C₃–C₁₀ alkenyl, a C₃–C₁₀ alkynyl, —C(RᵃRᵇ)— C(Rᵃ)=C(Rᵇ)—Ar and (CRᵃRᵇ)ₙAr, wherein n is an integer ranging from 0 to 10, wherein one or two carbons of said alkyl, alkenyl and alkynyl are optionally replaced by a diradical independently selected from —O—, —S—, —S(O)—, —S(O)$_2$—, a —N(C$_1$–C$_6$)alkyl- and —C(O)— and are optionally substituted by 1 to 3 substituents independently selected from the group S substituents;

R$^{13}$ is selected from H, a C$_1$–C$_{10}$ alkyl, a C$_3$–C$_{10}$ alkenyl, a C$_3$–C$_{10}$ alkynyl, OR$^8$, OC(O)R$^8$, OC(O)(CR$^a$R$^b$)$_n$Ar, OC(O)(CR$^a$R$^b$)$_n$NR$^8$(CR$^a$R$^b$)$_n$Ar, OC(O)NR$^8$R$^9$, OC(O)NR$^8$NR$^8$R$^9$, OC(O)NR$^8$(CR$^a$R$^b$)$_n$NR$^8$(CR$^a$R$^b$)$_n$Ar, OC(O)NR$^8$NR$^8$(CR$^a$R$^b$)$_n$NR$^8$(CR$^a$R$^b$)$_n$Ar, NR$^8$R$^9$, NR$^8$(CO)R$^8$, NR$^8$C(O)NR$^8$R$^9$, NR$^8$C(O)OR$^8$, O(CR$^a$R$^b$)$_n$Ar, O(CR$^a$R$^b$)$_n$NR$^8$(CR$^a$R$^b$)$_n$Ar, S(CR$^a$R$^b$)$_n$Ar, NH(CR$^a$R$^b$)$_n$NR$^8$(CR$^a$R$^b$)$_n$Ar and NH(CR$^a$R$^b$)$_n$Ar, wherein n is an integer ranging from 0 to 10;

each of R$^{14}$ and R$^{15}$ is independently selected from H, a C$_1$–C$_{12}$ alkyl, an aryl-substituted C$_1$–C$_{12}$ alkyl and a heteroaryl-substituted C$_1$–C$_{12}$ alkyl, wherein one or two carbons of said alkyl are optionally replaced by a diradical independently selected from —O—, —S—, —S(O)—, —S(O)$_2$—, a —N(C$_1$–C$_6$) alkyl- and —C(O)— and are optionally substituted by 1 to 3 substituents independently selected from the group S substituents;

R$^{14}$ and R$^{15}$ together with the carbon to which they are attached can form a 3- to 10-membered ring, in which one or two carbons are optionally replaced by a diradical independently selected from —O—, —S—, —S(O)—, —S(O)$_2$—, a —N(C$_1$–C$_6$)alkyl- and —C(O)— and are optionally substituted by 1 to 3 substituents independently selected from the group S substituents;

R$^{17}$ is a C$_1$–C$_{20}$ alkyl, wherein one or two carbons of said alkyl are optionally replaced by a diradical independently selected from —O—, —S—, —S(O)—, —S(O)$_2$—, a —N(C$_1$–C$_6$)alkyl- and —C(O)— and are optionally substituted by 1 to 3 substituents independently selected from the group S substituents, provided that R$^{17}$ is not unsubstituted ethyl;

R$^{18}$ is selected from the group consisting of an aryl, a substituted aryl, a heteroaryl, a substituted heteroaryl and a heterocycloalkyl;

each of R$^{19}$ and R$^{20}$ is independently selected from the group consisting of a C$_1$–C$_{12}$ alkenyl, a C$_1$–C$_{12}$ alkynyl, an aryl, a C$_3$–C$_8$ cycloalkyl, a heterocycloalkyl and a heteroaryl, wherein said alkenyl, alkynyl, aryl, cycloalkyl, heterocycloalkyl and heteroaryl are substituted or unsubstituted;

R$^{19}$ and R$^{20}$ together with the carbon to which they are attached can form a 3- to 10-membered heterocycloalkyl ring that may be substituted with one or more substituents independently selected from the group consisting of halogen, hydroxy, a C$_1$–C$_3$ alkoxy, a C$_1$–C$_3$ alkoxy-C$_1$–C$_3$ alkoxy, oxo, a C$_1$–C$_3$ alkyl, a halo-C$_1$–C$_3$ alkyl and a C$_1$–C$_3$ alkoxy-C$_1$–C$_3$ alkyl;

each Ar is independently a 4- to 10-membered heterocyclic or a C$_6$–C$_{10}$ aryl, wherein said heterocyclic and aryl groups are optionally substituted by one or more substituents independently selected from the group S substituents; and the group S substituents are selected from the group consisting of:
(a) nitro;
(b) halogens;
(c) hydroxy;
(d) N$_3$;
(e) CN;
(f) CHO;
(g) C$_1$–C$_{10}$ alkoxy;
(h) C$_1$–C$_3$ alkoxy-C$_1$–C$_3$ alkoxy;
(i) oxo;
(j) C$_1$–C$_{10}$ alkanoyl;
(k) C$_1$–C$_{10}$ alkyl;
(l) C$_1$–C$_{12}$ alkyl substituted with an aromatic heterocyclic;
(m) C$_1$–C$_6$ alkyl substituted with O—SO$_2$;
(n) C$_2$–C$_{10}$ alkenyl;
(o) C$_2$–C$_{10}$ alkynyl;
(p) C$_3$–C$_{10}$ cycloalkyl;
(q) substituted C$_3$–C$_{10}$ cycloalkyl;
(r) heterocyclic;
(s) substituted heterocyclic;
(t) aryl;
(u) substituted aryl;
(v) trialkylsilyl;
(w) —C(O)R$^8$;
(x) —C(O)R$^{18}$;
(y) —C(O)OR$^8$;
(z) —C(O)NR$^8$R$^9$;
(aa) —NR$^8$R$^9$;
(bb) —NR$^{19}$R$^{20}$;
(cc) —NHC(O)R$^8$;
(dd) —NHC(O)NR$^8$R$^9$;
(ee) =N—O—R$^8$;
(ff) =N—NR$^8$R$^9$;
(gg) =N—NR$^{19}$R$^{20}$;
(hh) =N—R$^8$;
(ii) =N—R$^{18}$;
(kk) =N—NHC(O)R$^8$;
(kk) =N—NHC(O)NR$^8$R$^9$;
(ll) —C≡N; *
(mm) —S(O)$_n$, wherein n is 0, 1 or 2;
(nn) —S(O)$_n$R$^8$, wherein n is 0, 1 or 2;
(oo) —O—S(O)$_n$R$^8$, wherein n is 0, 1 or 2; and
(pp) —SO$_2$NR$^8$R$^9$.

The present invention relates to compounds of formula 1A

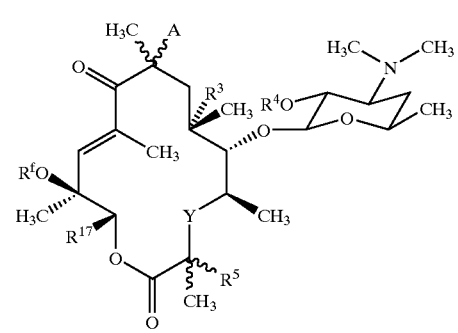

1A and to pharmaceutically acceptable salts, prodrugs and solvates thereof, wherein:

R$^f$ is selected from H, a —C(O)—imidazolyl, a C$_1$–C$_{12}$ alkyl, a C$_3$–C$_{10}$ alkenyl, a C$_3$–C$_{10}$ alkynyl, a —C(O)(C$_1$–C$_{18}$)alkyl, a —C(O)O(C$_1$–C$_{18}$)alkyl, —C(O)NR$^8$R$^9$ and CH$_2$( R$^a$R$^b$)$_n$Ar, wherein n is an integer ranging from 0 to 10, wherein one or two carbons of said alkyl are optionally replaced by a diradical independently selected from —O—, —S—, —S(O)—, —S(O)$_2$—, a —N(C$_1$–C$_6$)alkyl- and —C(O)— and are optionally substituted by 1 to 3 substituents independently selected from the group S substituents;

R$^3$ is selected from H and OR$^{10}$;

R$^{10}$ is selected from H, a C$_1$–C$_{10}$ alkyl, a C$_3$–C$_{10}$ alkenyl, a C$_3$–C$_{10}$ alkynyl, —C(R$^a$R$^b$)— C(R$^a$)=C(R$^b$)—Ar and $(CR^aR^b)_n Ar$, wherein n is an integer ranging from 1 to 10, wherein one or two carbons of said alkyl, alkenyl and alkynyl are optionally replaced by a diradical independently selected from —O—, —S—, —S(O)—, —S(O)$_2$—, a —N($C_1$-$C_6$)alkyl- and —C(O)— and are optionally substituted by 1 to 3 substituents independently selected from the group S substituents, provided that $R^{10}$ is not unsubstituted methyl; and A, Y, $R^4$, $R^5$, $R^7$, $R^8$, $R^9$, $R^{11}$, $R^{12}$, $R^{13}$, $R^{14}$, $R^{15}$, $R^{17}$, $R^{18}$, $R^{19}$, $R^{20}$, $R^a$, $R^b$, Ar and the group S substituents are defined as for formula 1.

More specific embodiments of this invention include compounds of formula 1 wherein A is H or F. Within this subset of compounds, all other variables are as originally defined.

More specific embodiments of this invention include compounds of formula 1 wherein X is selected from —C(O)—, —CH(NH$_2$)—, —CH$_2$NR$^9$—, —NR$^9$CH$_2$— and —C(=N—OR$^8$)—, wherein the first dash of each of the foregoing X groups is attached to the C-10 carbon of the compound of formula 1 and the last dash of each group is attached to the C-8 carbon of the compound of formula 1. Within this subset of compounds, all other variables are as originally defined.

More specific embodiments of this invention include compounds of formula I wherein X is selected from —CH$_2$N H—, —CH$_2$N(Me)—, —N(Me)CH$_2$—, —C(=N—OH)—, —C(=N—OMe)— and —C(=N—OCH$_2$CH$_2$OMe)—, wherein the first dash of each of the foregoing X groups is attached to the C-10 carbon of the compound of formula 1 and the last dash of each group is attached to the C-8 carbon of the compound of formula 1. Within this subset of compounds, all other variables are as originally defined.

More specific embodiments of this invention include compounds of formula 1 wherein $R^1$ is OH. Within this subset of compounds, all other variables are as originally defined.

More specific embodiments of this invention include compounds of formula 1 wherein $R^2$ is OH. Within this subset of compounds, all other variables are as originally defined.

More specific embodiments of this invention include compounds of formula 1 wherein $R^1$ is OH and $R^2$ is OH. Within this subset of compounds, all other variables are as originally defined.

More specific embodiments of this invention include compounds of formula 1 wherein $R^1$ is OH, $R^2$ is OH, A is H and X is selected from —CH$_2$NH—, —CH$_2$N(Me)—, —N(Me)CH$_2$—, —C(=N—OH)—, —C(=N—OMe)— and —C(=N—OCH$_2$CH$_2$OMe)—, wherein the first dash of each of the foregoing X groups is attached to the C-10 carbon of the compound of formula 1 and the last dash of each group is attached to the C-8 carbon of the compound of formula 1. Within this subset of compounds, all other variables are as originally defined.

More specific embodiments of this invention include compounds of formula 1 wherein $R^1$ is OH, $R^2$ is OH, A is F and X is selected from 'CH$_2$NH—, —CH$_2$N(Me)—, —N(Me)CH$_2$—, —C(=N—OH)—, —C(=N—OMe)— and —C(=N—OCH$_2$CH$_2$OMe)—, wherein the first dash of each of the foregoing X groups is attached to the C-10 carbon of the compound of formula 1 and the last dash of each group is attached to the C-8 carbon of the compound of formula 1. Within this subset of compounds, all other variables are as originally defined.

More specific embodiments of this invention include compounds of formula 1 wherein $R^1$ and $R^2$ taken with the intervening atoms form an additional ring having one of the following structures:

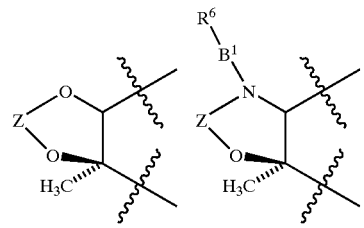

wherein Z is CH$_2$ or C(=O); $B^1$ is selected from NH, NMe and CH$_2$; and $R^6$ is (CH$_2$)$_n$Ar, wherein n is an integer ranging from 0 to 10. Within this subset of compounds, all other variables are as originally defined.

More specific embodiments of this invention include compounds of formula 1 wherein $R^1$ and X taken with the intervening atoms form an additional ring having the following structure:

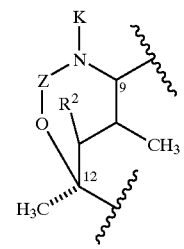

Within this subset of compounds, all other variables are as originally defined.

More specific embodiments of this invention include compounds of formula 1 wherein $R^1$ and X taken with the intervening atoms form an additional ring having the following structure:

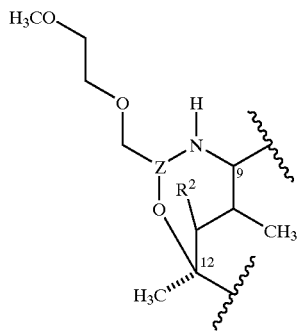

Within this subset of compounds, all other variables are as originally defined.

More specific embodiments of this invention include compounds of formula 1 wherein $R^1$ and $R^2$ taken with the intervening atoms form an additional ring having one of the following structures:

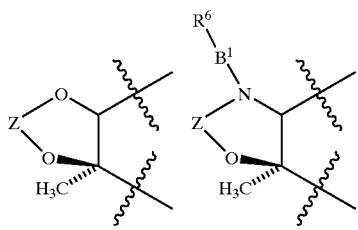

wherein Z is CH$_2$ or C(=O); B$^1$ is selected from NH, NMe and CH$_2$; and R$^6$ is (CH$_2$)$_3$Ar, wherein n is an integer ranging from 0 to 10. Within this subset of compounds, all other variables are as originally defined.

More specific embodiments of this invention include compounds of formula 1 wherein R$^1$ and R$^2$ taken with the intervening atoms form an additional ring having one of the following structures:

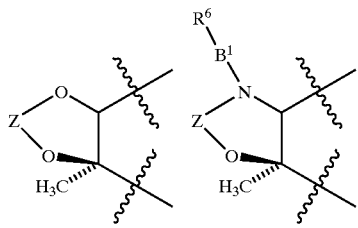

wherein Z is CH$_2$ or C(=O); B$^1$ is selected from NH, NMe and CH$_2$; R$^6$ is (CH$_2$)$_3$Ar; and Ar is selected from quinolin-4-yl, 4-phenyl-imidazol-1-yl, imidazo(4,5-b) pyridin-3-yl and 4-pyridin-3-yl-imidazol-1-yl. Within this subset of compounds, all other variables are as originally defined.

More specific embodiments of this invention include compounds of formula 1 wherein R$^3$ is selected from an O(C$_1$–C$_4$)alkyl, OCH$_2$CH=CH—Ar and O(CH$_2$)$_n$Ar. Within this subset of compounds, all other variables are as originally defined.

More specific embodiments of this invention include compounds of formula 1 wherein Y is selected from CH$_2$, C(O), C=S, CH(OR$^8$), CH(OC(O)R$^8$), CH(OC(O)Ar), CH(OC(O)NR$^8$R$^9$) and CH(O(CR$^a$R$^b$)$_n$Ar), wherein n is an integer ranging from 0 to 10.

More specific embodiments of this invention include compounds of formula 1 wherein Y has the following structure:

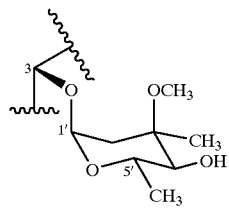

More specific embodiments of this invention include compounds of formula 1 wherein Y has the following structure:

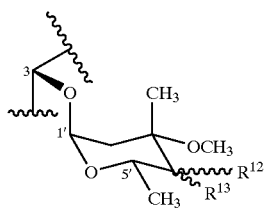

wherein R$^{12}$ is H and R$^{13}$ is selected from OR$^8$, OC(O)R$^8$, O(CR$^a$R$^b$)$_n$Ar, OC(O)(CR$^a$R$^b$)$_n$Ar, OC(O)(CR$^a$R$^b$)$_n$NR$^8$(CR$^a$R$^b$)$_n$Ar, OC(O)NR$^8$R$^9$, OC(O)NR$^8$NR$^8$R$^9$, OC(O)NR$^8$(CR$^a$R$^b$)$_n$NR$^8$(CR$^a$R$^b$)$_n$Ar, OC(O)NR$^8$NR$^8$ (CR$^a$R$^b$)$_n$NR$^8$(CR$^a$R$^b$)$_n$Ar, OC(O)NR$^8$R$^9$, OC(O) NR$^8$NR$^8$R$^9$, NR$^8$C(O)NR$^8$R$^9$, NR$^8$C(O)OR$^8$, O(CR$^a$R$^b$)$_n$NR$^8$(CR$^a$R$^b$)$_n$Ar, S(CR$^a$R$^b$)$_n$Ar, NH(CR$^a$R$^b$)$_n$NR$^8$(CR$^a$R$^b$)$_n$Ar and NH(CR$^a$R$^b$)$_n$Ar, wherein n is an integer ranging from 0 to 10, and all other variables are as originally defined;

or R$^{13}$ is OH and R$^{12}$ is selected from CH$_2$N$_3$, CH$_2$NH$_2$, CH$_2$NR$^8$(CR$^a$R$^b$)$_n$Ar, CH$_2$NR$^8$R$^9$, CH$_2$NR$^8$NR$^8$R$^9$, CH$_2$NR (CR$^a$R$^b$)$_n$NR$^8$(CR$^a$R$^b$)$_n$Ar, CH$_2$NR$^8$NR$^8$ (CR$^a$R$^b$)$_n$NR$^8$(CR$^8$R$^b$)$_n$Ar, CH$_2$NR$^8$C(O)R$^8$, CH$_2$NR$^8$C(O)NR$^8$R$^9$, CH$_2$NR$^8$C(O)OR$^8$, CH$_2$O (CR$^a$R$^b$)$_n$NR$^8$(CR$^a$R$^b$)$_n$Ar, CH$_2$S(CR$^a$R$^b$)$_n$Ar and CH$_2$NH(CR$^a$R$^b$)$_n$Ar, wherein n is an integer ranging from 0 to 10, and all other variables are as originally defined;

or R$^{13}$ is OH and R$^{12}$ is selected from H, a C$_1$–C$_{10}$ alkyl, a C$_3$–C$_{10}$ alkenyl, a C$_3$–C$_{10}$ alkynyl, —C(R$^a$R$^b$)—C (R$^a$)=C(R$^b$)—Ar and (CR$^a$R$^b$)$_n$Ar, wherein n is an integer ranging from 0 to 10, wherein one or two carbons of said alkyl, alkenyl and alkynyl are optionally replaced by a diradical independently selected from —O—, —S—, —S(O)—, —S(O)$_2$—, a —N(C$_1$–C$_6$)alkyl- or —C(O)— and are optionally substituted by 1 to 3 substituents independently selected from the group S substituents, and all other variables are as originally defined;

or R$^{12}$ and R$^{13}$ together with the carbon to which they are attached can form —C(O)—, —C(=N—OR$^8$)— or —C(=N—R$^8$)—, and all other variables are as originally defined.

More specific embodiments of this invention include compounds of formula 1 wherein R$^{14}$ and R$^{15}$ together with the carbon to which they are attached form the following structure:

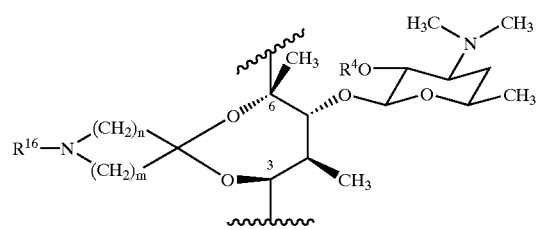

wherein each of n and m is independently an integer from 1 to 6; and R$^{16}$ is selected from R$^8$, C(O)R$^8$, C(O)Ar, C(O)OR$^8$ (CR$^a$R$^b$)$_n$Ar, C(O)(CR$^a$R$^b$)$_n$Ar, C(O) (CR$^a$R$^b$)$_n$NR$^8$(CR$^a$R$^b$)$_n$Ar, C(O)NR$^8$R$^9$, C(O) NR$^8$NR$^8$R$^9$, C(O)NR$^8$(CR$^a$R$^b$)$_n$NR$^8$(CR$^a$R$^b$)$_n$Ar, C(O) NR$^8$NR$^8$(CR$^a$R$^b$)$_n$NR$^8$(CR$^a$R$^b$)$_n$Ar, NR$^8$NR$^8$R$^9$, (CR$^a$R$^b$)$_n$NR$^8$(CR$^a$R$^b$)$_n$Ar and (CR$^a$R$^b$)$_n$NR$^8$(CR$^a$R$^b$)

$_n$Ar, wherein n is an integer ranging from 0 to 10, and all other variables are as originally defined.

More specific embodiments of this invention include compounds of formula 1 wherein $R^4$ is H or Ac. Within this subset of compounds, all other variables are as originally defined.

More specific embodiments of this invention include compounds of formula 1 wherein $R^5$ is H or F. Within this subset of compounds, all other variables are as originally defined.

More specific embodiments of this invention include compounds of formula 1A wherein A is H or F. Within this subset of compounds, all other variables are as originally defined.

More specific embodiments of this invention include compounds of formula 1A wherein $R^f$ is selected from H, a —C(O)—imidazolyl, —C(O)$OR^8$, —C(O)(CH$_2$)$_n$Ar, —C(O)$NR^8R^9$ and —C(O)$NR^8NR^8R^9$, wherein n is an integer ranging from 0 to 10. Within this subset of compounds, all other variables are as originally defined.

More specific embodiments of this invention include compounds of formula 1A wherein $R^3$ is selected from OH, an O(C$_2$-C$_4$)alkyl, OCH$_2$CH=CH—Ar and O(CH$_2$)$_n$Ar, wherein n is an integer ranging from 1 to 10. Within this subset of compounds, all other variables are as originally defined.

More specific embodiments of this invention include compounds of formula 1A wherein Y is selected from CH$_2$, C(O), C=S, CH(OR$^8$), CH(OC(O)R$^8$), CH(OC(O)Ar), CH(OC(O)NR$^8$R$^9$) and CH(O(CR$^a$R$^b$)$_n$Ar), wherein n is an integer ranging from 0 to 10. Within this subset of compounds, all other variables are as originally defined.

More specific embodiments of this invention include compounds of formula 1A wherein Y has the following structure:

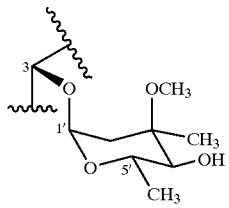

Within this subset of compounds, all other variables are as originally defined.

More specific embodiments of this invention include compounds of formula 1A wherein Y has the following structure:

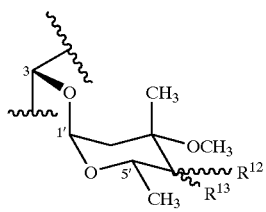

wherein $R^{12}$ is H and $R^{13}$ is selected from OR$^8$, OC(O)R$^8$, O(CR$^a$R$^b$)$_n$Ar, OC(O)(CR$^a$R$^b$)$_n$Ar, OC(O)(CR$^a$R$^b$)$_n$NR$^8$(CR$^a$R$^b$)$_n$Ar, OC(O)NR$^8$R$^9$, OC(O)NR$^8$NR$^8$R$^9$, OC(O)NR$^8$(CR$^a$R$^b$)$_n$NR$^8$(CR$^a$R$^b$)$_n$Ar, OC(O)NR$^8$NR$^9$ (CR$^a$R$^b$)$_n$NR$^8$(CR$^a$R$^b$)$_n$Ar, NR$^8$R$^9$, NR$^8$(CO)R$^8$, NR$^8$C (O)NR$^8$R$^9$, NR$^8$C(O)OR$^8$, O(CR$^a$R$^b$)$_n$NR$^8$(CR$^a$R$^b$)$_n$ Ar, S(CR$^a$R$^b$)$_n$Ar, NH(CR$^a$R$^b$)$_n$NR$^8$(CR$^a$R$^b$)$_n$Ar and N(CR$^a$R$^b$)$_n$Ar, wherein n is an integer ranging from 0 to 10, and all other variables are as originally defined;

or $R^{13}$ is OH and $R^{12}$ is selected from CH$_2$N$_3$, CH$_2$NH$_2$, CH$_2$NR$^8$(CR$^a$R$^b$)$_n$Ar, CH$_2$NR$^8$R$^9$, CH$_2$NR$^8$NR$^8$R$^9$, CH$_2$NR$^8$(CR$^a$R$^b$)NR$^8$(CR$^a$R$^b$)$_n$Ar, CH$_2$NR$^8$NR$^8$ (CR$^a$RB$^b$)$_n$NR (CR$^a$R$^b$)$_n$Ar, CH$_2$NR$^8$C(O)R$^8$, CH$_2$NR$^8$C(O)NR$^8$R$^9$, CH$_2$NR$^8$C(O)OR$^8$, CH$_2$O (CR$^a$R$^b$)$_n$NR$^8$(CR$^a$R$^b$)$_n$Ar, CH$_2$S(CR$^a$R$^b$)$_n$Ar and CH$_2$NH(CR$^a$R$^b$)$_n$Ar, wherein n is an integer ranging from 0 to 10, and all other variables are as originally defined;

or $R^{13}$ is OH and $R^{12}$ is selected from H, a C$_1$-C$_{10}$ alkyl, a C$_3$-C$_{10}$ alkenyl, a C$_3$-C$_{10}$ alkynyl, —C(R$^a$R$^b$)—C (R$^a$)=C(R$^b$)—Ar and (CR$^a$R$^b$)$_n$Ar, wherein n is an integer ranging from 0 to 10, wherein one or two carbons of said alkyl, alkenyl and alkynyl are optionally replaced by a diradical independently selected from —O—, —S—, —S(O)—, —S(O)$_2$—, a —N(C$_1$-C$_6$)alkyl- and —C(O)— and are optionally substituted by 1 to 3 substituents independently selected from the group S substituents, and all other variables are as originally defined;

or $R^{12}$ and $R^{13}$ together with the carbon to which they are attached can form —C(O)—, —C(=N—OR$^8$)— or —C(=N—R$^8$)—, and all other variables are as originally defined.

More specific embodiments of this invention include compounds of formula 1A wherein $R^{14}$ and $R^{15}$ together with the carbon to which they are attached form the following structure:

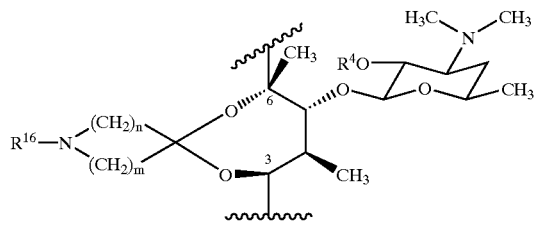

wherein each of n and m is independently an integer from 1 to 6, and $R^{16}$ is selected from R$^8$, C(O)R$^8$, C(O)Ar, C(O)OR$^8$, (CR$^a$R$^b$)$_n$Ar, C(O)(CR$^a$R$^b$)$_n$Ar, C(O) (CR$^a$R$^b$)$_n$NR$^8$(CR$^a$R$^b$)$_n$Ar, C(O)NR$^8$R$^9$, C(O) NR$^8$NR$^8$R$^9$, C(O)NR$^8$(CR$^a$R$^b$)$_n$NR$^8$(CR$^a$R$^b$)$_n$Ar, C(O) NR$^8$NR$^8$(CR$^a$R$^b$)$_n$NR$^8$(CR$^a$R$^b$)$_n$Ar, NR$^8$NR$^8$R$^9$, (CR$^a$R$^b$)$_n$NR$^8$(CR$^a$R$^b$)$_n$Ar and (CR$^a$R$^b$)$_n$NR$^8$(CR$^a$R$^b$)$_n$ Ar, wherein n is an integer ranging from 0 to 10. Within this subset of compounds, all other variables are as originally defined.

More specific embodiments of this invention include compounds of formula 1A wherein $R^4$ is H or Ac. Within this subset of compounds, all other variables are as originally defined.

More specific embodiments of this invention include compounds of formula 1A wherein $R^5$ is H or F. Within this subset of compounds, all other variables are as originally defined.

Examples of preferred compounds of this invention include the following compounds:

the compound of formula 1 wherein $R^1$ is OH; $R^2$ is OH; A is F; X is selected from —C(O)—, —CH$_2$NH—, —CH$_2$NMe—, —NHCH$_2$—, —N(Me)CH$_2$—, —CH (NH$_2$)—, —C(=N—OMe)— and —C(=N—OCH$_2$O (CH$_2$)$_2$OMe)—; $R^4$ is H; $R^5$ is H; and Y is CH(O-cladinose), wherein O-cladinose represents the following structure:

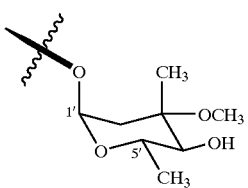

the compound of formula 1 wherein $R^1$ and $R^2$ together form —OC(O)O—; A is F; X is selected from —C(O)—, —CH$_2$NH—, —CH$_2$NMe—, —NHCH$_2$—, —N(Me)CH$_2$—, —CH(NH$_2$)—, —C(=N—OMe)— and —C(=N—OCH$_2$O(CH$_2$)$_2$OMe)—; $R^3$ is OH; $R^4$ is H; $R^5$ is H; and Y is CH(O-cladinose);

the compound of formula I wherein $R^1$ and $R^2$ together form —OCH$_2$O—; A is F; X is selected from —C(O)—, —CH$_2$NH—, —CH$_2$NMe—, —NHCH$_2$—, —N(Me)CH$_2$—, —CH(NH$_2$)—, —C(=N—OMe)— and —C(=N—OCH$_2$O(CH$_2$)$_2$OMe)—; $R^4$ is H; $R^5$ is H; and Y is CH(O-cladinose);

compounds having the following formulas:

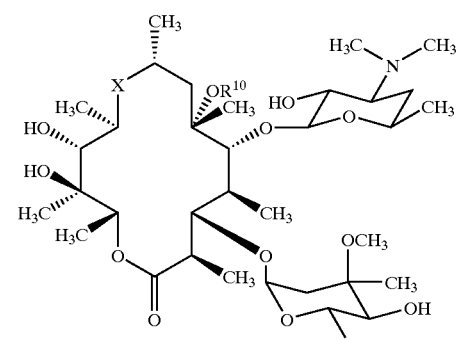

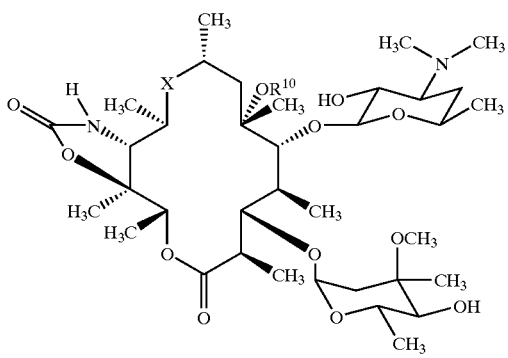

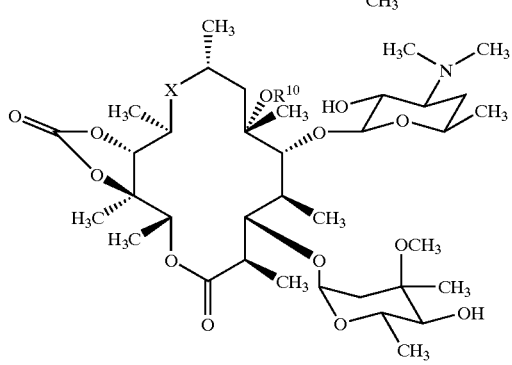

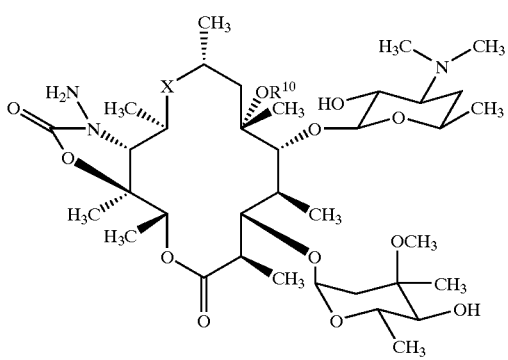

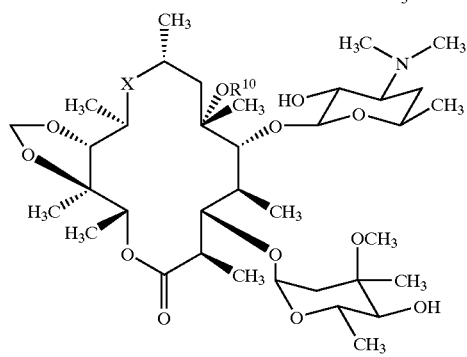

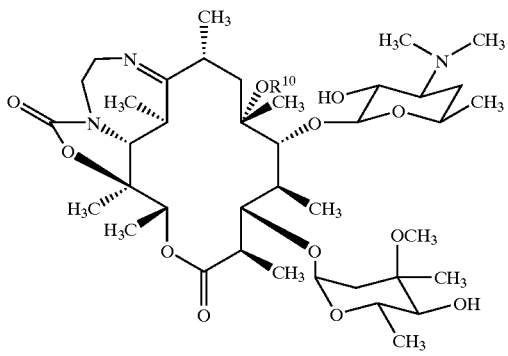

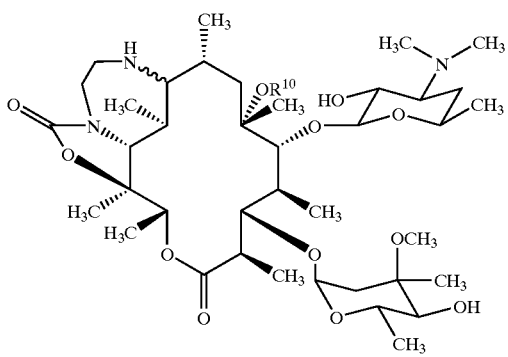

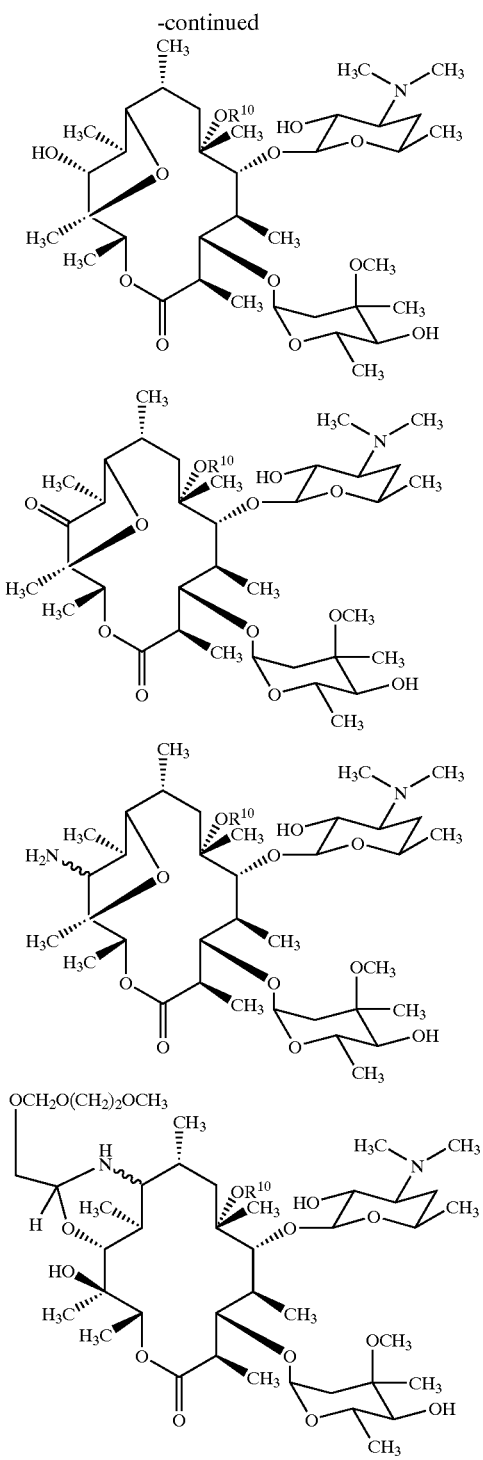

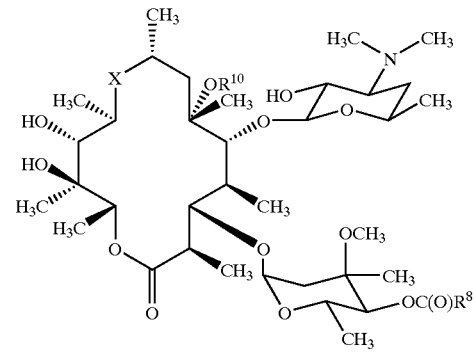
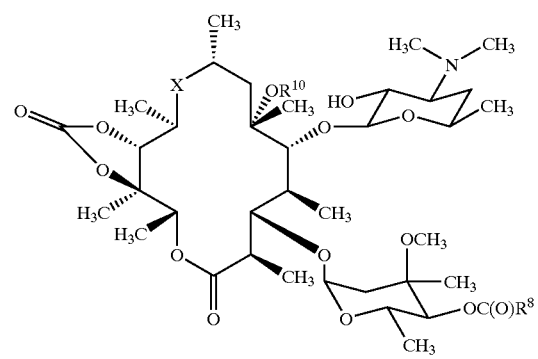
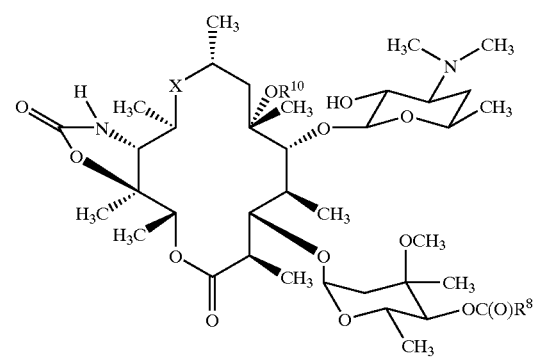
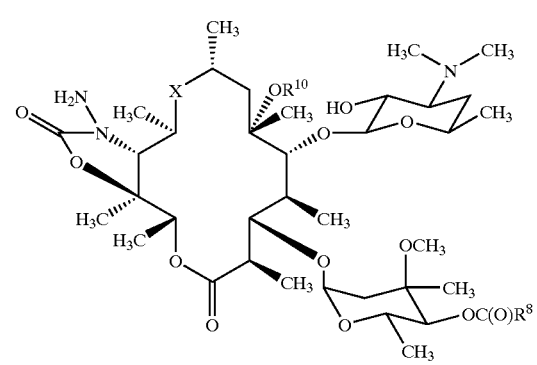

quinolyl), CH₂CH=CH-(8-quinolyl), CH₂CH₂NHCH₂-(4-pyridyl) and CH₂CH₂NHCH₂-(4-quinolyl);

compounds having the following formulas:

wherein X is selected from —C(O)—, —CH₂NH—, —CH₂NMe—, —NHCH₂—, —N(Me)CH₂—, —CH(NH₂)—, —C(=N—OMe)— and —C(=N—OCH₂O(CH₂)₂OMe)—; and $R^{10}$ is selected from Et, n-Pr, cyclopropyl, cyclobutyl, COCH₃, CH₂CH₂CH₂-(4-pyridyl), CH₂CH=CH₂-(4-pyridyl), CH₂CH₂CH₂-(4-quinolyl), CH₂CH=CH-(4-quinolyl), CH₂CH₂CH₂-(5-quinolyl), CH₂CH=CH-(5quinolyl), CH₂CH₂CH₂-(4-benzimidazolyl), CH₂CH=CH-(4-benzimidazolyl), CH₂CH₂CH₂-(8-

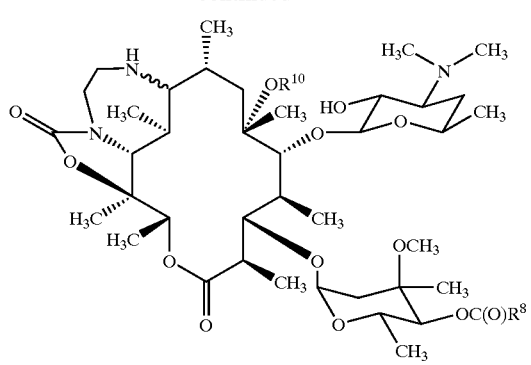

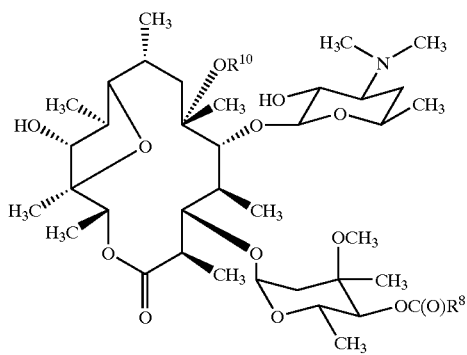

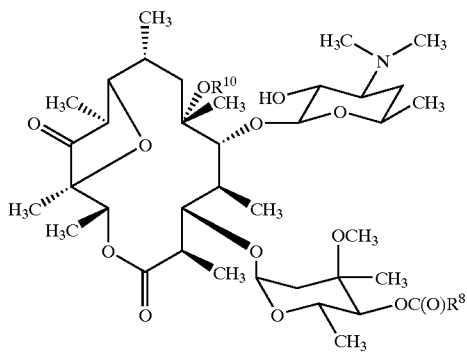

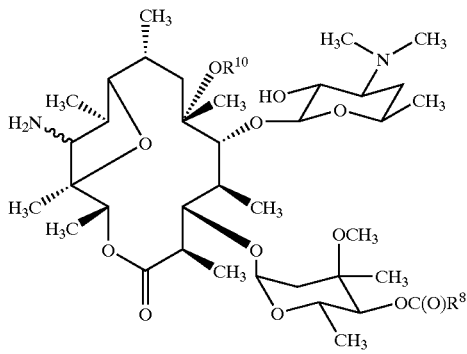

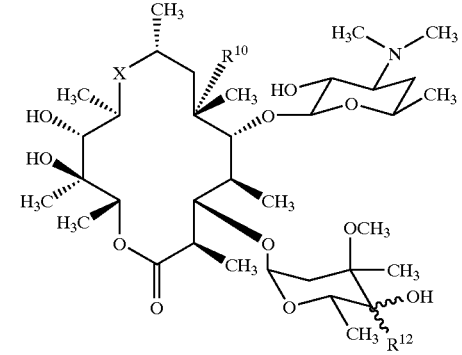

wherein X is selected from —C(O)—, —CH₂NMe—, —NHCH₂—, —N(Me)CH₂—, —CH(NH₂)—, —C(=N—OMe)— nd —C(=N—OCH₂O(CH₂)₂OMe)—;

$R^{10}$ is selected from Et, n-Pr, cyclopropyl, cyclobutyl, COCH₃, CH₂CH₂CH₂-(4-pyridyl), CH₂CH=CH₂-(4-pyridyl), CH₂CH₂CH₂-(4-quinolyl), CH₂cH=CH—(4-quinolyl), CH₂CH₂CH₂-(5-quinolyl), CH₂CH=CH-(5-quinolyl), CH₂CH₂CH₂-(4-benzimidazolyl), CH₂CH=CH—(4-benzimidazolyl), CH₂CH₂CH₂-(8-quinolyl), CH₂CH=CH-(8-quinolyl), CH₂CH₂NHCH₂-(4-pyridyl) and CH₂CH₂NHCH₂-(4-quinolyl);

$R^8$ is selected from NH(CH₂)₂N(me)CH₂Ar, NH(CH₂)₂NHCH₂Ar, O(CH₂)N(Me)CH₂Ar and O(CH₂)₂NHCH₂Ar; and Ar is selected from phenyl, 2-methoxyphenyl, 4-methoxyphenyl, quinolin-4-yl, 7-methoxy-quinolin-4-yl, 4-phenyl-imidaol-1-yl, pyridin-4-yl, pyridin-3-yl, pyridin-2-yl, 4-pyridin-3-yl-imidazol-1-yl, imidazo(4,5-b)pyridin-3-yl, 2-phenyl-thiazol-5-yl, 2-pyridin-3-yl-thiazol-4-yl and benzoimidazol-1-yl;

compounds having the following formulas:

-continued
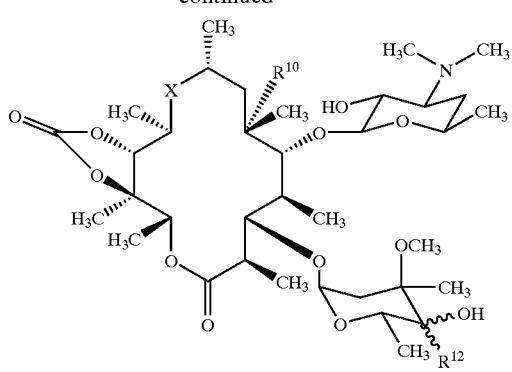
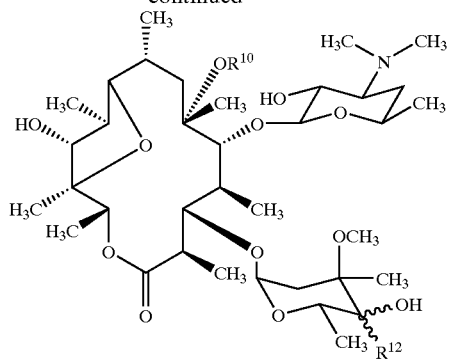
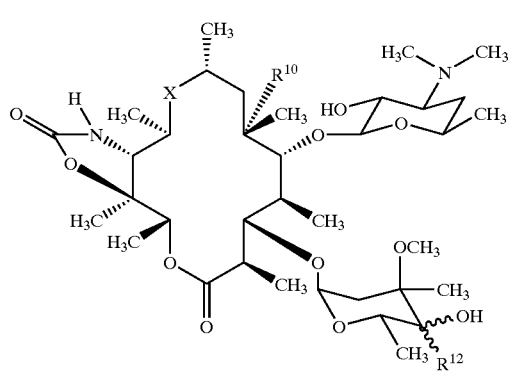
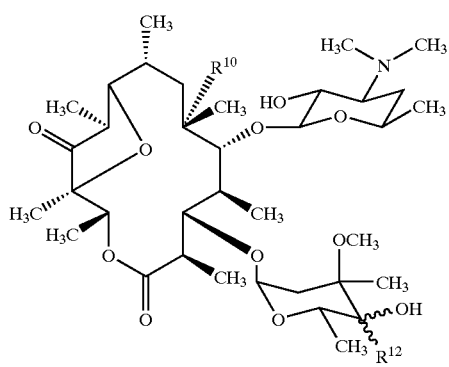
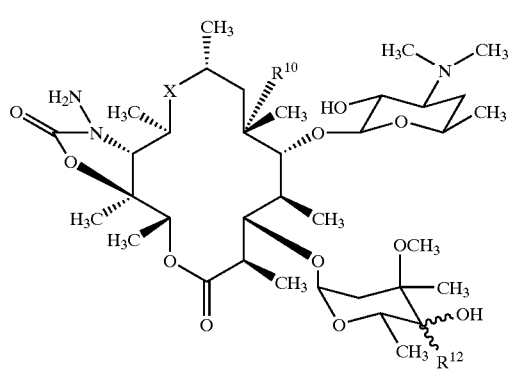
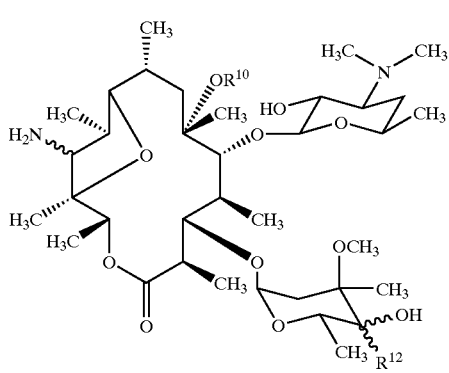
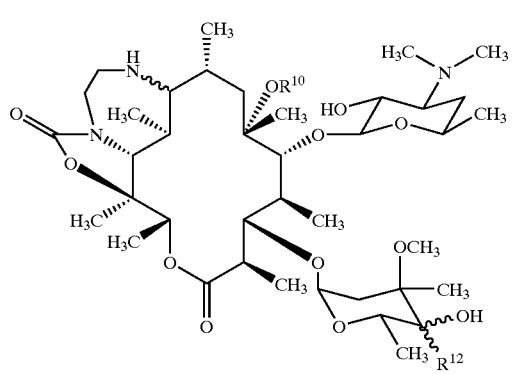
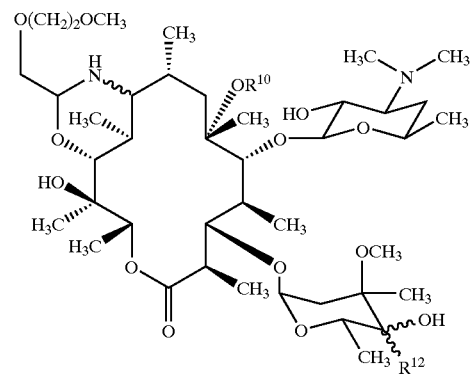

wherein X is selected from —C(O)—, —CH$_2$NH—, —CH$_2$NMe—, —NHCH$_2$—, —N(Me)CH$_2$—, —CH(NH$_2$)—, —C(=N—OMe)— and —C(=N—OCH$_2$O(CH$_2$)$_2$OMe)—;

R$^{10}$ is selected from Et, n-Pr, cyclopropyl, cyclobutyl, COCH$_3$, CH$_2$CH$_2$CH$_2$-(4-pyridyl), CH$_2$CH=CH$_2$-(4-pyridyl), CH$_2$CH$_2$CH$_2$-(4-quinolyl), CH$_2$CH=CH—(4-quinolyl), CH$_2$CH$_2$CH$_2$-(5-quinolyl), CH$_2$CH=CH-(5-quinolyl), CH$_2$CH$_2$CH$_2$-(4-benzimidazolyl), CH$_2$CH=CH-(4-benzimidazolyl), CH$_2$CH$_2$CH$_2$-(8-quinolyl), CH$_2$CH=CH-(8-quinolyl), CH$_2$CH$_2$NHCH$_2$-(4-pyridyl) and CH$_2$CH$_2$NHCH$_2$-(4-quinolyl);

R$^{12}$ is selected from H, Me, Et, propyl, cyclopropyl, cyclobutyl, CH$_2$N$_3$, CH$_2$NH$_2$, CH$_2$NHMe, CH$_2$NHEt, CH$_2$NH-n-pr, CH$_2$NH-cyclopropyl, CH$_2$NH-iso-propyl, CH$_2$NH(CH$_2$)$_2$NH$_2$, CH$_2$NH(CH$_2$)$_2$NHCH$_2$Ar and CH$_2$NH(CH$_2$)$_2$N(Me)CH$_2$Ar; and Ar is selected from phenyl, 2-methoxyphenyl, 4-methoxyphenyl, quinolin-4-yl, 7-methoxy-quinolin-4-yl, 4-phenyl-imidazol-1-yl, pyridin4-yl, pyridin-3-yl, pyridin-2-yl, 4-pyridin-3-yl-imidazol-1-yl, imidazo(4,5-b)pyridin-3-yl, 2-phenyl-thiazol-5-yl, 2-pyridin-3-yl-thiazol-4-yl and benzoimidazol-1-yl;

compounds having the following formulas:

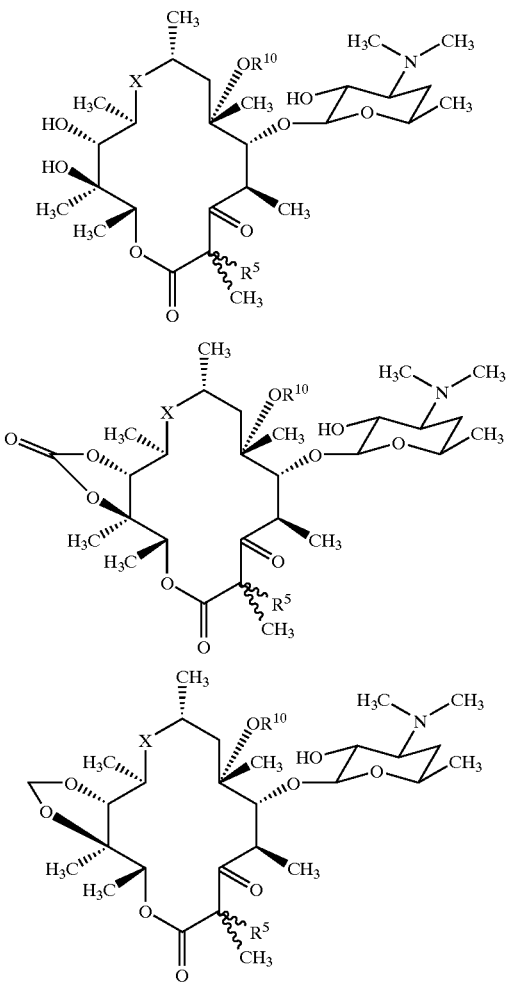

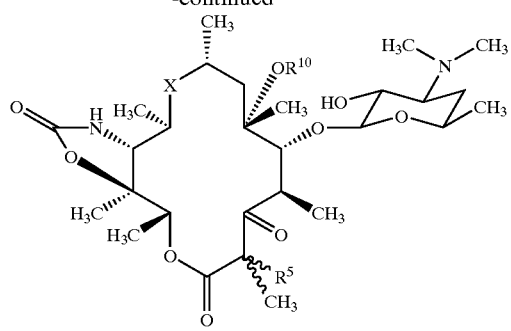

-continued

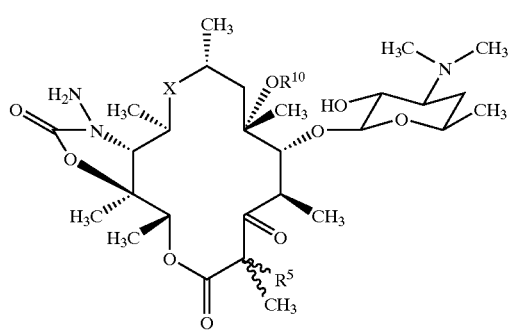

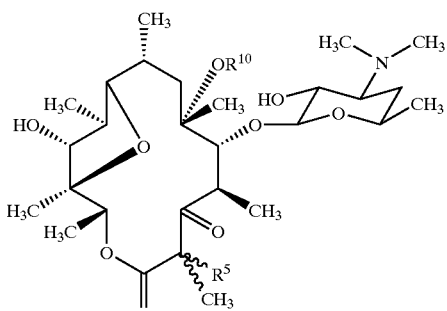

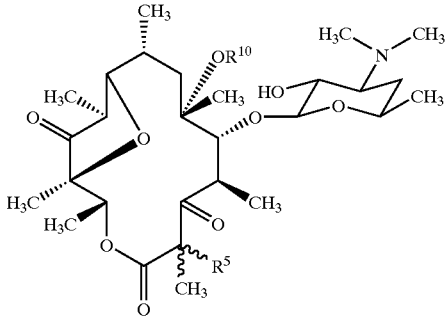

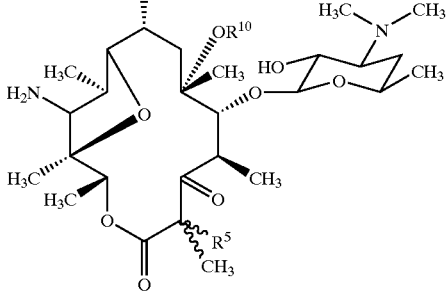

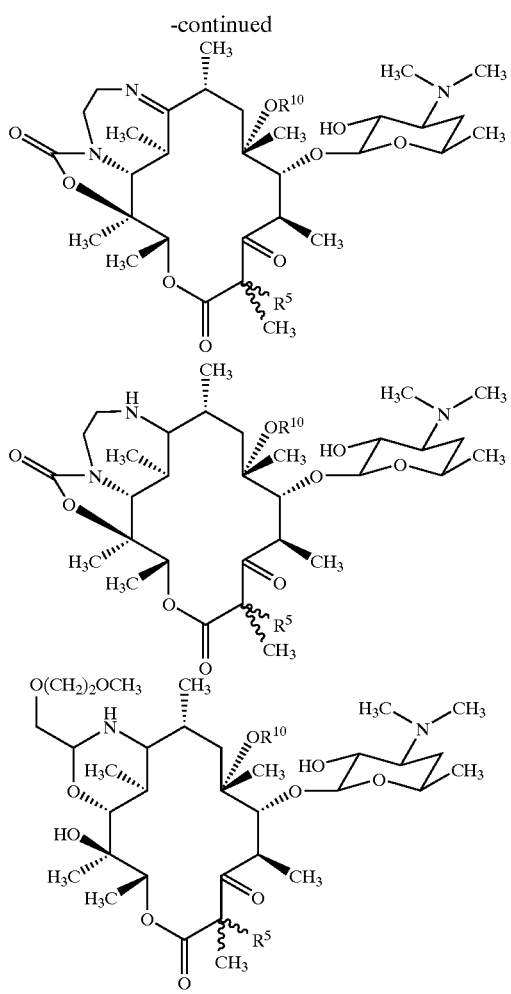

wherein $R^{10}$ is selected from Et, n-Pr, cyclopropyl, cyclobutyl, $COCH_3$, $CH_2CH_2CH_2$-(4-pyridyl), $CH_2CH=CH_2$-(4-pyridyl), $CH_2CH_2CH_2$-(4-quinolyl), $CH_2CH=CH$-(4-quinolyl), $CH_2CH_2CH_2$-(5-quinolyl), $CH_2CH=CH$-(8-quinolyl), $CH_2CH_2CH_2$-(4-benzimidazolyl), $CH_2CH=CH$-(4-benzimidazolyl), $CH_2CH_2CH_2$-(8-quinolyl), $CH_2CH=CH$-(8-quinolyl), $CH_2CH_2NHCH_2$-(4pyridyl) and $CH_2CH_2NHCH_2$-(4quinolyl);

$R^5$ is H or F; and

X is selected from —C(O)—, —$CH_2$NH—, —$CH_2$NMe—, —NH$CH_2$—, —N(Me)$CH_2$—, —CH(NH$_2$)—, —C(=N—OMe)— and —C(=N—O$CH_2$O(CH$_2$)$_2$OMe)—;

compounds having the following formula:

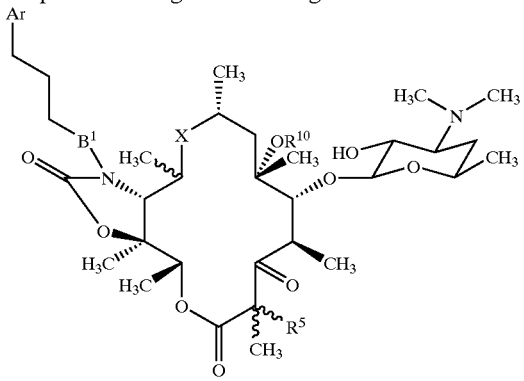

wherein $B^1$ is selected from NH, O and $CH_2$;

X is selected from —C(O)—, —$CH_2$NH—, —$CH_2$NMe—, —NH$CH_2$—, —N(Me)$CH_2$—, —CH(NH$_2$)—, —C(=N—OMe)— and —C(=N—O$CH_2$O(CH$_2$)$_2$OMe)—;

$R_5$ is H or F; and

Ar is selected from quinolin4-yl, 7-methoxy-quinolin4-yl, 4-phenyl-imidazol-1-yl, pyridin-4-yl, pyridin-3-yl, pyridin-2-yl, 4-pyridin-3-yl-imidazol-1-yl, phenyl, imidazo(4,5-b)pyridin-3-yl, 2-phenyl-thiazol-5-yl, 2-pyridin-3-yl-thiazol-4-yl and benzoimidazol-1-yl;

compounds having the following formula:

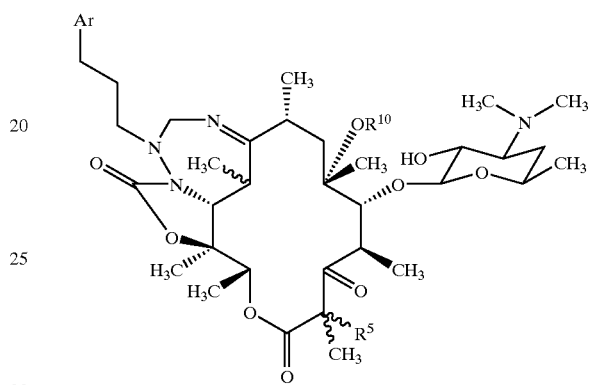

wherein Ar is selected from quinolin4-yl, 7-methoxy-quinolin4-yl, 4-phenyl-imidazol-1-yl, pyridin4-yl, pyridin-3-yl, pyridin-2-yl, 4-pyridin-3-yl-imidazol-1-yl, phenyl, imidazo(4,5-b)pyridin-3-yl, 2-phenyl-thiazol-5-yl, 2-pyridin-3-yl-thiazol-4-yl and benzoimidazol-1-yl; and $R^5$ is H or F;

compounds having the following formula:

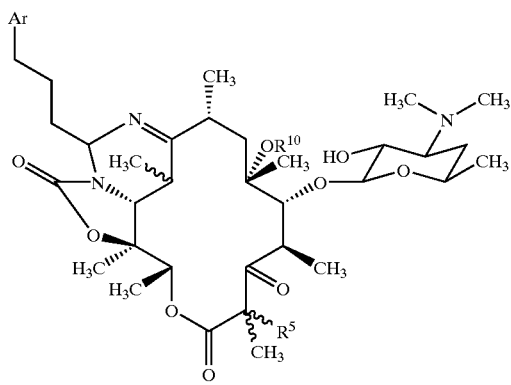

wherein Ar is selected from quinolin-4-yl, 7-methoxy-quinolin4-yl, 4-phenyl-imidazol-1-yl, pyridin4-yl, pyridin-3-yl, pyridin-2-yl, 4-pyridin-3-yl-imidazol-1-yl, phenyl, imidazo(4,5-b)pyridin-3-yl, 2-phenyl-thiazol-5-yl, 2-pyridin-3-yl-thiazol4-yl and benzoimidazol-1-yl; and $R^5$ is H or F;

compounds having the following formula:

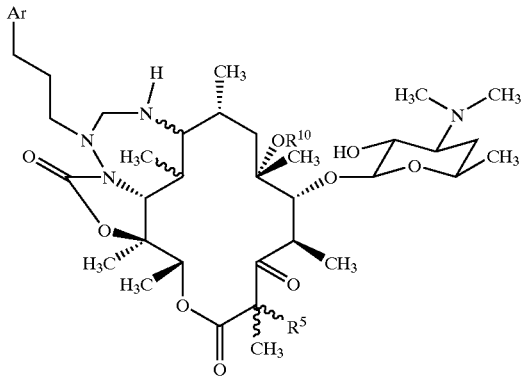

wherein Ar is selected from quinolin-4-yl, 7-methoxy-quinolin-4-yl, 4-phenyl-imidazol-1-yl, pyridin4-yl, pyridin-3-yl, pyridin-2-yl, 4-pyridin-3-yl-imidazol-1-yl, phenyl, imidazo(4,5-b)pyridin-3-yl, 2-phenyl-thiazol-5-yl, 2-pyridin-3-yl-thiazol-4-yl and benzoimidazol-1-yl; and $R^5$ is H or F;

compounds having the following formula:

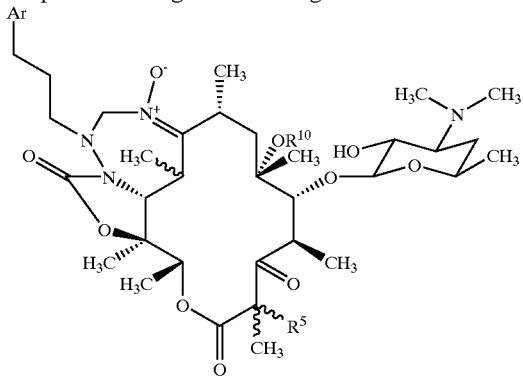

wherein Ar is selected from quinolin4-yl, 7-methoxy-quinolin4-yl, 4-phenyl-imidazol-1-yl, pyridin4-yl, pyridin-3-yl, pyridin-2-yl, 4-pyridin-3-yl-imidazol-1-yl, phenyl, imidazo(4,5-b)pyridin-3-yl, 2-phenyl-thiazol-5-yl, 2-pyridin-3-yl-thiazol-4-yl and benzoimidazol-1-yl; and $R^5$ is H or F;

compounds having the following formula:

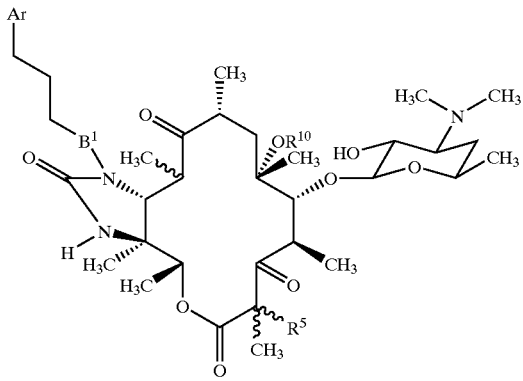

wherein Ar is selected from quinolin4-yl, 7-methoxy-quinolin-4-yl, 4-phenyl-imidazol-1-yl, pyridin-4-yl, pyridin-3-yl, pyridin-2-yl, 4-pyridin-3-yl-imidazol-1-yl, phenyl, imidazo(4,5-b)pyridin-3-yl, 2-phenyl-thiazol-5-yl, 2-pyridin-3-yl-thiazol-4-yl and benzoimidazol-1-yl; and $R^5$ is H or F;

compounds having the following formula:

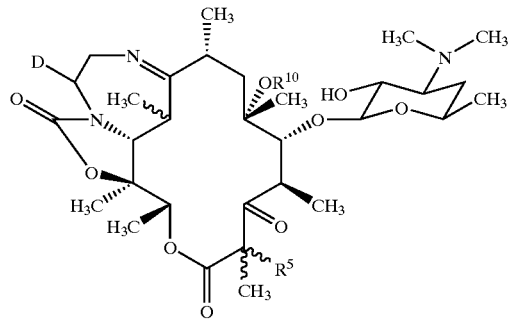

wherein $R^5$ is H or F;

D is selected from $CH_2Ar$, $CH_2NH_2$, $CH_2NHCH_2Ar$, $CH_2OH$, $(CH_2)_3Ar$, $CH_2OCH_2Ar$, $CH_2SCH_2Ar$, $CH_2NHCH_2Ar$, $CH_2N(Me)CH_2Ar$ and $CH_2OCH_2$—Ar; and Ar is selected from quinolin-4-yl, 7-methoxy-quinolin-4-yl, 4-phenyl-imidazol-1-yl, pyridin-4-yl, pyridin-3-yl, pyridin-2-yl, 4-pyridin-3-yl-imidazol-1-yl, phenyl, imidazo(4,5-b)pyridin-3-yl, 2-phenyl-thiazol-5-yl, 2-pyridin-3-yl-thiazol-4-yl and benzoimidazol-1-yl;

compounds having the following formula:

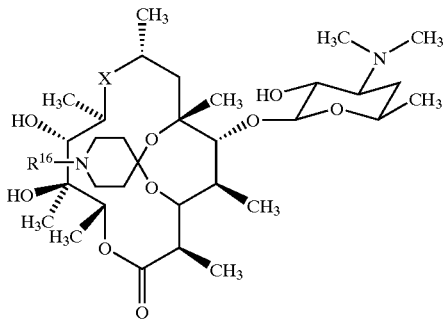

wherein $R^{16}$ is selected from H, Me, Et, n-propyl, cyclopropyl, cyclobutyl, C(O)Me, C(O)Ar, C(O)OMe, $(CH_2)_3Ar$, $(CH_2)_2Ar$, $(CH_2)_2NHCH_2Ar$ and $(CH_2)_2N(Me)CH_2Ar$; and Ar is selected from phenyl, quinolin-4-yl, 7-methoxy-quinolin-4-yl, 4-phenyl-imidazol-1-yl, pyridin-4-yl, pyridin-3-yl, pyridin-2-yl, 4-pyridin-3-yl-imidazol-1-yl, phenyl, imidazo(4,5-b)pyridin-3-yl, 2-phenyl-thiazol-5-yl, 2-pyridin-3-yl-thiazol-4-yl and benzoimidazol-1-yl;

the compound of formula 1A wherein $R^1$ is H or —C(O)-imidazolyl; A is H or F; $R^3$ is selected from OH, OEt, O-cyclopropyl and O-n-propyl; $R^4$ is selected from H, Ac and trimethylsilyl; $R^5$ is H or F; and Y is selected from CH(O-cladinose), CH(O-(4"-O-acetyl)-cladinose), CH(OH), C=O and CH(OAc).

Certain compounds of formulas 1 and 1A may contain one or more asymmetric carbons and may therefore exist in different isomeric forms. This invention includes all pure individual enantiomers and individual diastereomers of the compounds of formulas 1 and 1A and mixtures comprising any combination of these isomers. Each stereogenic carbon may be of the R or S configuration. In particular, the invention includes both the R and S configurations of C-2, C-8, C-9, C-10 and C-11 of the macrolide ring of formula 1. The invention further includes all E and Z configurations of the compounds of formulas 1 and 1A and mixtures thereof. Although specific compounds exemplified in this application may be depicted in a particular stereochemical configuration, compounds having either the opposite stereochemistry at any given chiral center or mixtures thereof are also envisioned. The compounds of formulas 1 and 1A may additionally exist as tautomers. This invention includes all such pure tautomers and mixtures thereof. The invention includes uses of any of the above compounds or mixtures of compounds.

The compounds of this invention may be modified by appropriate functionalities to enhance selective biological properties. This invention includes all pharmaceutically acceptable derivatives or prodrugs of the compounds of formulas 1 and IA. This invention also includes all pharmaceutically acceptable salts of the compounds of formulas 1 and 1A.

The present invention includes all isotopically labelled forms of the compounds of formulas 1 and 1A, and pharmaceutically acceptable salts thereof. Such isotopically labelled compounds are useful as research or diagnostic tools.

The invention also relates to processes for preparing a compound of formula 1.

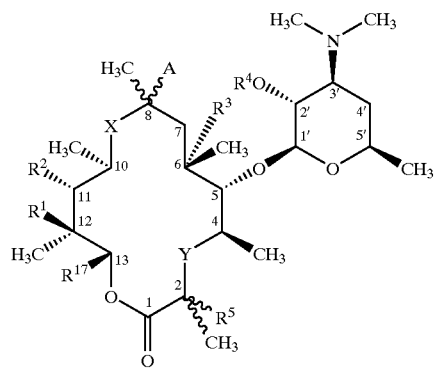

One such process comprises treating a compound of formula 3, wherein $R^8$ is hydrogen, with mesyl chloride or mesyl chloride and a base such as DBU, pyridine or triethylamine.

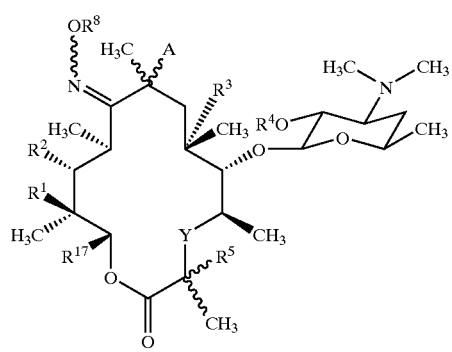

Another process comprises treating a compound of formula 50 with an appropriate nucleophile in the presence of an acid to open the epoxide moiety at the 4" position.

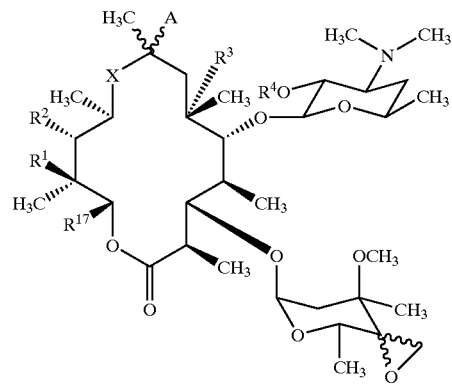

Another process comprises treating a compound of formula 63 with $R^6B^1NH_2$ or $NH_2C(D)(E)C(F)(G)NH_2$.

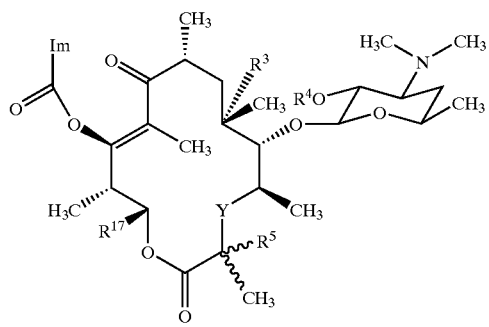

Another process comprises treating a compound of formula 69 with $C(D)(E)(O)$ in the presence of an acid such as acetic acid.

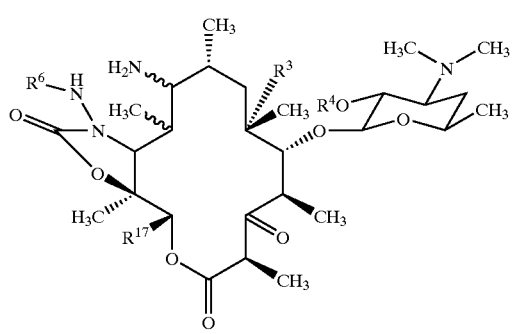

Another process comprises treating a compound of formula 82 with an azide reagent such as $TMS-N_3$ in the presence of a Lewis acid.

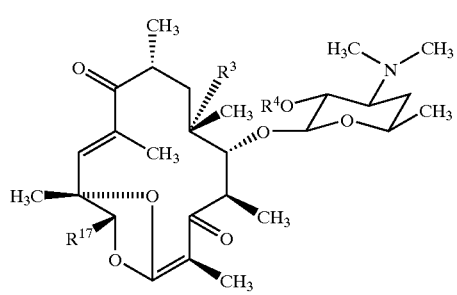

Another process comprises treating a compound of formula 87 with $R^{14}R^{15}C(O)$ in the presence of an acid such as para-toluenesulfonic acid.

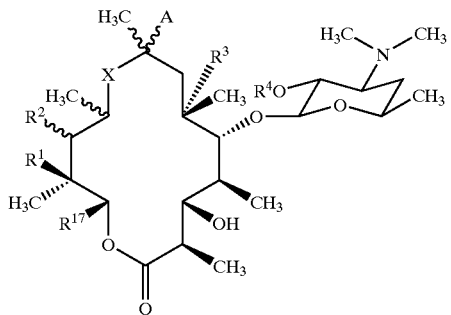

87

The present invention also relates to a pharmaceutical composition for the treatment of a bacterial or protozoal infection, or a disorder related to a bacterial or protozoal infection. This pharmaceutical composition comprises a therapeutically effective amount of a compound of formula 1 or 1A, or a pharmaceutically acceptable salt, prodrug or solvate thereof, and a pharmaceutically acceptable carrier or diluent. The pharmaceutical composition may comprise one or more additional agents having an antibiotic effect or other therapeutic or prophylactic effect.

The present invention further includes a method of treating a bacterial infection or a protozoal infection, or a disorder related to a bacterial or protozoal infection, in humans, other mammals, fish or birds in need of such treatment. The methods of the present invention comprise administering to said human, other mammal, fish or bird a therapeutically effective amount of a compound of formula 1 or 1A, a pharmaceutically acceptable salt, prodrug or solvate thereof, or a pharmaceutical composition comprising the compound as defined above. This invention contemplates treatment methods in which the compounds of the present invention are administered either as a single agent or in combination with other therapeutic agents.

Patients that can be treated with the compounds of formulas 1 and 1A, pharmaceutically acceptable salts, solvates and prodrugs thereof, or pharmaceutical compositions comprising the compounds include mammals (particularly humans), fish and birds suffering from infections caused by various microorganisms, including Gram-positive and Gram-negative bacteria.

As used herein, unless otherwise indicated, the term "infection(s)" includes "bacterial infection(s)", "protozoal infection(s)" and "disorders related to bacterial infections or protozoal infections". These terms include bacterial infections and protozoal infections that occur in mammals, fish and birds, as well as disorders related to bacterial infections or protozoal infections that may be treated or prevented by administering the compounds of the present invention. Such bacterial infections, protozoal infections and disorders related to such bacterial and protozoal infections include the following: pneumonia, otitis media, sinusitus, bronchitis, tonsillitis and mastoiditis related to infection by *Streptococcus pneumoniae, Haemophilus influenzae, Moraxella catarrhalis, Staphylococcus aureus, Enterococcus faecalis, E. faecium, E. casselflavus, S. epidermidis, S. haemolyticus* or *Peptostreptococcus* spp.; pharyngitis, rheumatic fever and glomerulonephritis related to infection by *Streptococcus pyogenes*, Groups C and *G streptococci, Clostridium diptheriae, Corynebacterium diphtheriae* or *Actinobacillus haemolyticum*; respiratory tract infections related to infection by *Mycoplasma pneumoniae, Legionella pneumophlla, Streptococcus pneumoniae, Haemophilus influenzae* or *Chiamydia pneumoniae*; blood and tissue infections, including endocarditis and osteomyelitis, caused by *S. aureus, S. haemolyticus, E faecalis, E. faecium* or *E. durans*, including strains resistant to known antibacterials such as, but not limited to, beta-lactams, vancomycin, aminoglycosides, quinolones, chloramphenicol, tetracylines and macrolides; uncomplicated skin and soft tissue infections and abscesses, and puerperal fever related to infection by *Staphylococcus aureus*, coagulase-positive staphylococci (i.e., *S. epidermidis, S. hemolyticus*, etc.), *Streptococcus pyogenes, Streptococcus agalactiae*, Streptococcal groups C–F (minute-colony streptococci), viridans streptococci, *Corynebacterium minutissimum*, Clostridium spp. or *Bartonella henselae*; uncomplicated acute urinary tract infections related to infection by *Staphylococcus aureus, Staphylococcus saprophyticus*, coagulase-negative staphylococcal species or Enterococcus spp.; urethritis and cervicitis; sexually transmitted diseases related to infection by *Chlamydia trachomatis, Haemophilus ducreyi, Treponema pallidum, Ureaplasma urealyticum* or *Neiserria gonorrheae*; toxin diseases related to infection by *S. aureus* (food poisoning and toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis and dacrocystitis related to infection by *Chlamydia trachomatis, Neisseria gonorrhoeae, S. aureus, S. pneumoniae, S. pyogenes, H. influenzae* or Listeria spp.; disseminated Mycobacterium avium complex (MAC) disease related to infection by *Mycobacterium avium* or *Mycobacterium intracellulare*; infections caused by Mycobacterium tuberculosis, *M. leprae, M. paratuberculosis, M. kansasli* or *M. chelonei*; gastroenteritis related to infection by *Campylobacter jejuni*; intestinal protozoa related to infection by Cryptosporidium spp.; odontogenic infection related to infection by *viridans streptococci*; persistent cough related to infection by *Bordetella pertussis*; gas gangrene related to infection by *Clostridium peffringens* or Bacteroides spp.; and atherosclerosis or cardiovascular disease related to infection by *Helicobacter pylon* or *Chlamydia pneumoniae*. Bacterial infections and protozoal infections, and disorders related to such infections, that may be treated or prevented in animals include the following: bovine respiratory disease related to infection by *P. haemolytica, P. multocida, Mycoplasma bovis* or Bordetella spp.; cow enteric disease related to infection by *E. coli* or protozoa (i.e., coccidia, cryptosporidia, etc.); dairy cow mastitis related to infection by *S. aureus, Strep. uberis, Streptococcus agalactiae, Streptococcus dysgalactiae*, Klebsiella spp., Corynebacterium or Enterococcus spp.; swine respiratory disease related to infection by *A. pleuro., P. multocida* or Mycoplasma spp.; swine enteric disease related to infection by *E. coli, Lawsonia intracellularis*, Salmonella or *Serpulina hyodysinte-*

*riae*; cow footrot related to infection by Fusobacterium spp.; cow metritis related to infection by *E. coli*; cow hairy warts related to infection by *Fusobacterium necrophorum* or *Bacteroides nodosus*; cow pink-eye related to infection by *Moraxella bovis*; cow premature abortion related to infection by protozoa (i.e. neosporium); urinary tract infection in dogs and cats related to infection by *E. coli*; skin and soft tissue infections in dogs and cats related to infection by *S. epidermidis, S. intermedius,* coagulase neg. Staphylococcus or *P. multocida*; and dental or mouth infections in dogs and cats related to infection by Alcaligenes spp., Bacteroides spp., Clostridium spp., Enterobacter spp., Eubacterium, Peptostreptococcus, Porphyromonas or Prevotella. Other bacterial infections, protozoal infections and disorders related to bacterial or protozoal infections that may be treated or prevented in accord with the method of the present invention are referred to in J. P. Sanford et al., "The Sanford Guide To Antimicrobial Therapy," 26th Edition (Antimicrobial Therapy, Inc., 1996).

DETAILED DESCRIPTION OF THE INVENTION

The present invention comprises novel compounds of formulas 1 and 1A and pharmaceutically acceptable salts, prodrugs and solvates thereof that are antibacterial and/or antiprotozoal agents. The present invention further comprises methods of preparing the claimed compounds, pharmaceutical compositions comprising the compounds, and methods of treatment using the compounds and compositions.

In the chemical structures depicted herein, a wavy line indicates that the stereochemistry at the chiral center to which the wavy line is connected is either an R or an S configuration where the wavy line is connected to a carbon atom. In the compound of formula 1, the wavy lines at positions 2, 8, 10 and 11 of the macrolide ring indicate that these carbons have either an R or an S configuration. A wavy line connected to an oxime nitrogen indicates that the oxime geometry is in an E or Z configuration.

The term "halo", as used herein, unless otherwise indicated, refers to fluoro, chloro, bromo or iodo. Preferred halo groups are fluoro, chloro and bromo.

The term "alkyl", as used herein, unless otherwise indicated, includes saturated monovalent hydrocarbon radicals having straight, cyclic or branched moieties, or a combination of the foregoing moieties. Said alkyl group may include one or two double or triple bonds. For cycloalkyls, at least three carbon atoms are required in said alkyl group. Said cycloalkyls may include mono- or polycyclic alkyl radicals. Examples of alkyl radicals include, but are not limited to, methyl, ethyl, n-propyl, isopropyl, n-butyl, isobutyl, sec-butyl, tert-butyl, pentyl, isoamyl, n-hexyl, cyclohexyl, adamantyl, norbomyl and the like.

The term "alkenyl", as used herein, unless otherwise indicated, includes straight-chain or branched-chain mono- or poly-unsaturated aliphatic hydrocarbon radicals containing at least one carbon-carbon double bond. Examples of alkenyl radicals include, but are not limited to, ethenyl, E- and Z-propenyl, isopropenyl, E- and Z-butenyl, E- and Z-isobutenyl, E- and Z-pentenyl, E- and Z-hexenyl, E,E-, E,Z-, Z,E- and Z,Z-hexadienyl and the like.

The term "alkynyl", as used herein, unless otherwise indicated, includes straight-chain or branched-chain mono- or poly-unsaturated aliphatic hydrocarbon radicals containing at least one carbon-carbon triple bond. Examples of alkynyl radicals include, but are not limited to, ethynyl, E- and Z-propynyl, isopropynyl, E- and Z-butynyl, E- and Z-isobutynyl, E- and Z-pentynyl, E- and Z-hexynyl and the like.

The term "alkoxy", as used herein, unless otherwise indicated, includes alkyl ether radicals, wherein the term "alkyl" is as defined above. Examples of suitable alkyl ether radicals include, but are not limited to, methoxy, ethoxy, n-propoxy, isopropoxy, n-butoxy, isobutoxy, sec-butoxy, tert-butoxy and the like.

The term "alkanoyl", as used herein, unless otherwise indicated, includes —C(O)—alkyl groups wherein "alkyl" is as defined above.

The term "aryl", as used herein, unless otherwise indicated, includes an organic radical derived from an aromatic hydrocarbon by the removal of one hydrogen. Examples of aryl radicals include, but are not limited to, phenyl, naphthyl, indenyl, indanyl, azulenyl, fluorenyl, anthracenyl and the like.

The term "substituted", whether preceded by the term "optionally" or not, and substitutions contained in formulas of this invention refer to the replacement of one or more hydrogen radicals in a given structure with the radical of a specified substituent. When more than one position in a given structure may be substituted with more than one substituent selected from a specified group, the substituents may be either the same or different at every position. In some cases, two positions in a given structure may be substituted with one shared substituent. Most preferred substituents are those that enhance antibacterial or antiprotozoal activity.

As used herein, unless otherwise indicated, "Ac" indicates an acetyl group.

As used herein, unless otherwise indicated, "Me" indicates a methyl group.

As used herein, unless otherwise indicated, "Et" indicates an ethyl group.

The term "4- to 10-membered heterocyclic", as used herein, unless otherwise indicated, includes aromatic and non-aromatic heterocyclic groups containing one or more heteroatoms, each selected from O, S and N, wherein each heterocyclic group has from 4 to 10 atoms in its ring system. Non-aromatic heterocyclic groups include groups having only 3 atoms in their ring system, but aromatic heterocyclic groups must have at least 5 atoms in their ring system. The heterocyclic groups include benzo-fused ring systems and ring systems substituted with one or more oxo moieties. An example of a 4-membered heterocyclic group is azetidinyl (derived from azetidine). An example of a 5-membered heterocyclic group is thiazolyl, and an example of a 10-membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached).

The term "protecting group" refers to a suitable chemical group that may be attached to a functional group and removed at a later stage to reveal the intact functional group. Examples of suitable protecting groups for various functional groups are described in T. W. Greene and P. G. M Wuts, *Protective Groups in Organic Synthesis*, 2d Ed., John Wiley and Sons (1991); L. Fieser and M. Fieser, *Fieser and Fieser's Reagents for Organic Synthesis*, John Wiley and Sons (1994); and L. Paquette, ed. *Encyclopedia of Reagents for Organic Synthesis*, John Wiley and Sons (1995).

The term "acid" refers to an electron pair acceptor.

The term "base" refers to an electron pair donor.

The term "therapeutically effective amount" refers to an amount effective in treating or ameliorating a bacterial infection or protozoal infection, or a disorder involving a bacterial or protozoal infection, in a patient, either as monotherapy or in combination with other agents. The term "treating" as used herein refers to the alleviation of symptoms of a bacterial infection or protozoal infection, or a particular disorder involving a bacterial infection or protozoal infection, in a patient, or the improvement of an ascertainable measurement associated with such a disorder. As used herein, the term "patient" refers to mammals (including humans), fish and birds suffering from a bacterial infection or a protozoal infection, or a disorder involving a bacterial infection or protozoal infection.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

The term "pharmaceutically acceptable carrier" refers to a carrier that may be administered to a patient together with a compound of this invention. The carrier does not destroy the pharmacological activity of the compound and is non-toxic when administered in doses sufficient to deliver a therapeutic amount of the compound.

As used herein, the compounds of this invention, including the compounds of formulas 1 and 1A, are defined to include pharmaceutically acceptable derivatives or prodrugs thereof. A "pharmaceutically acceptable derivative or prodrug" means any pharmaceutically acceptable salt, ester, salt of an ester or other derivative of a compound of this invention that, upon administration to a recipient, is capable of providing (directly or indirectly) a compound of this invention or a metabolite or residue thereof. Particularly favored derivatives and prodrugs are those that increase the bioavailability of the compounds of this invention when such compounds are administered to a patient (e.g., by allowing an orally administered compound to be more readily absorbed into the blood), enhance delivery of the parent compound to a given biological compartment, increase solubility to allow administration by injection, alter metabolism or alter rate of excretion.

Compounds of formulas 1 and 1A can be converted into prodrugs through, for example, free amino, amido, hydroxy or carboxylic groups. Examples of such prodrugs include compounds wherein an amino acid residue, or a polypeptide chain of two or more (e.g., two, three or four) amino acid residues is covalently joined through an amide or ester bond to a free amino, hydroxy or carboxylic acid group of a compound of formula 1 or 1A. The amino acid residues include but are not limited to the 20 naturally occurring amino acids commonly designated by three letter symbols and also include 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs are also encompassed. For instance, free carboxyl groups can be derivatized as amides or alkyl esters. The amide and ester moieties may incorporate groups including but not limited to ether, amine and carboxylic acid functionalities. Free hydroxy groups may be derivatized using groups including but not limited to hemisuccinates, phosphate esters, dimethylaminoacetates and phosphoryloxymethyloxycarbonyls, as outlined in D. Fleisher et al., *Advanced Drug Delivery Reviews*, vol. 19, p. 115 (1996). Carbamate prodrugs of hydroxy and amino groups are also included, as are carbonate prodrugs and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in R. P. Robinson et al., *J. Medicinal Chemistry*, vol. 39, p. 10 (1996).

The compounds of this invention also include pharmaceutically acceptable salts of the compounds of formulas 1 and 1A. The term "pharmaceutically acceptable salt(s)", as used herein, unless otherwise indicated, includes salts of acidic or basic groups that may be present in the compounds of the present invention.

The compounds of the present invention that are basic in nature are capable of forming a wide variety of salts with various inorganic and organic acids. The acids that may be used to prepare pharmaceutically acceptable acid addition salts of such basic compounds of formulas 1 and 1A are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. The compounds of the present invention that include a basic moiety, such as an amino group, may form pharmaceutically acceptable salts with various amino acids, in addition to the acids mentioned above.

Those compounds of the present invention that are acidic in nature are capable of forming base salts with various pharmacologically acceptable cations. Examples of such salts include the alkali metal or alkaline earth metal salts and, particularly, the calcium, magnesium, sodium and potassium salts of the compounds of the present invention.

The subject invention also includes isotopically-labelled compounds and pharmaceutically acceptable salts thereof that are identical to those recited in formulas 1 and 1A, but for the fact that one or more atoms are replaced by an atom having an atomic mass or mass number different from the atomic mass or mass number usually found in nature. Examples of isotopes that can be incorporated into compounds of this invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$ and $^{36}Cl$, respectively. Compounds of the present invention, prodrugs thereof, and pharmaceutically acceptable salts of said compounds or of said prodrugs that contain the aforementioned isotopes and/or other isotopes of other atoms are within the scope of this invention. Certain isotopically labelled compounds of the present invention, such as those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Substitution with heavier isotopes such as deuterium, i.e., $^2H$, can afford certain therapeutic advantages resulting from greater metabolic stability, for example, increased in vivo half-life or reduced dosage requirements, and hence may be preferred in some circumstances. Isotopically labelled compounds of formulas 1 and 1A of this invention and prodrugs thereof can generally be prepared by carrying out the procedures disclosed in the Schemes and/or in the Examples below and substituting a readily available isotopically labelled reagent for a non-isotopically labelled reagent.

The compounds of the present invention are readily prepared. Starting materials useful for the preparation of the compounds of formulas 1 and 1A can be prepared using methods such as those described in International Application WO 98/01571, PUBLISHED Jan. 15, 1998; International Application WO 98/01546, PUBLISHED Jan. 15, 1998; International Application WO 99/35156, PUBLISHED Jul. 15, 1999; and WO 99/35157, published Jul. 15, 1999; all of which are incorporated herein by reference in their entirety. In particular, starting materials may be prepared by fermenting suitable organisms. Production of such starting materials involves the manipulation of polyketide biosynthetic genes or portions of them, which may be derived from different polyketide biosynthetic gene clusters.

Polyketides are a large and structurally diverse class of natural products that includes many compounds possessing antibiotic or other pharmacological properties, such as erythromycin, tetracyclines, rapamycin, avermectin, polyether ionophores and FK506. In particular, polyketides are abundantly produced by Streptomyces and related actinomycete bacteria. They are synthesized by the repeated stepwise condensation of acylthioesters in a manner analogous to that of fatty-acid biosynthesis. The greater structural diversity found among natural polyketides arises from the selection of (usually) acetate or propionate as "starter" or "extender" units, and from the differing degree of processing of the β-keto group observed after each condensation. Examples of processing steps include reduction to β-hydroxyacyl-, reduction followed by dehydration to 2-enoyl-, and complete reduction to the saturated acylthioester. The stereochemical outcome of these processing steps is specified for each cycle of chain extension.

The biosynthesis of polyketides is initiated by a group of chain-forming enzymes known as polyketide synthases. Two classes of polyketide synthase ("PKS") have been described in actinomycetes. One class, designated Type I, includes the PKS's for the macrolides erythromycin, oleandomycin, avermectin and rapamycin. In Type I PKS's, a different set or "module" of enzymes is responsible for each cycle of polyketide chain extension (Cortes, J. et al., *Nature*, vol. 348, pp. 176–178 (1990); Donadio, S. et al., *Science*, vol. 252, pp. 675–679 (1991); Swan, D. G. et al., *Mol. Gen. Genet.*, vol. 242, pp. 358–362 (1994); MacNeil, D. J. et al., *Gene*, vol. 115, pp. 119–125 (1992); Schwecke, T. et al., *Proc. Natl. Acad. Sci. USA*, vol. 92, pp. 7839–7843 (1995)).

The term "extension module" as used herein refers to the set of contiguous domains, from a ketoacyl-ACP synthase ("AKS") domain to the next acyl carrier protein ("ACP") domain, that accomplishes one cycle of polyketide chain extension. The term "loading module" is used to refer to any group of contiguous domains that accomplishes the loading of the starter unit onto the PKS, rendering it available to the β-ketoacylsynthase ("KS") domain of the first extension module. The length of the polyketide formed has been altered, in the case of erythromycin biosynthesis, through specific relocation of the enzymatic domain of the erythromycin-producing PKS that contains the chain-releasing thioesterase/cyclase activity (Cortes et al., Science, vol. 268, pp. 1487–1489 (1995); Kao, C. M. etal., *J. Am. Chem. Soc.*, vol. 117, pp. 9105–9106 (1995)).

As noted in International Application WO 98101571, PUBLISHED Jan. 15, 1998, the Type I PKS gene assembly encodes a loading module that is followed by extension modules. The genes for the erythromycin-producing PKS (known as 6-deoxyerythronolide B synthase, "DEBS") contain three open reading frames that encode the DEBS polypeptides. The genes are organized in six repeated units designated modules. The first open reading frame encodes the first multi-enzyme or cassette (DEBS1), which consists of three modules: the loading module and two extension modules (modules 1 and 2). The loading module comprises an AT and an ACP.

The DEBS loading module has a slightly broader specificity than propionate only. In particular, acetate starter units are used both in vitro and in vivo, when the PKS containing this loading module is part of a PKS that is expressed either in the natural host for erythromycin production, *Saccharopolyspora erythraea* (see, for example, Cortes, J. et al., *Science*, vol. 268, pp. 1487–1489 (1995)), or in a heterologous host such as Saccharopolyspora coelicolor (Kao, C. M. et al., *J. Am. Chem. Soc.*, vol. 116, pp. 11612–11613 (1994); Brown, M. J. B. et al., *J. Chem. Soc. Chem. Commun.*, pp. 1517–1519 (1995)). In vitro experiments using purified DEBS1-TE have demonstrated that propionyl-CoA and acetyl-CoA are alternative substrates that efficiently supply propionate and acetate units, respectively, to the loading module (Wiessmann, K. E. H. et al., *Chemistry and Biology*, vol. 2, pp. 583–589 (1995); Pieper, R. et al., *J. Am. Chem. Soc.*, vol. 117, pp. 11373–11374 (1995)). The outcome of the competition between acetate and propionate starter units is influenced by the respective intracellular concentrations of propionyl-CoA and acetyl-CoA prevailing in the host cell used (see, for example, Kao, C. M. et al., *Science*, vol. 265, pp. 509–512 (1994); Pereda, A. et al., *Microbiology*, vol. 144, pp. 543–553 (1995)). It also depends upon the level of expression of the host PKS. As disclosed for example in International Application WO 98/01546, PUBLISHED Jan. 15, 1998, when recombinant DEBS or another hybrid PKS containing the DEBS loading module is overexpressed in *S. erythraea*, the products are generally mixtures whose components differ only in the presence of either an acetate or a propionate starter unit.

In-frame deletion of the DNA encoding part of the ketoreductase domain of module 5 in DEBS has been shown to lead to the formation of erythromycin analogues 5,6-dideoxy-3-mycarosyl-5-oxoerythronolide B, 5,6-dideoxy-5-oxoerythronolide B and 5,6-dideoxy6,6-epoxy-5-oxoerythronolide B (Donadio, S. et al., *Science*, vol. 252, pp. 675–679 (1991)). Likewise, alteration of active-site residues in the enoylreductase domain of module 4 in DEBS, by genetic engineering of the corresponding PKS-encoding DNA and its introduction into S. erythraea, has been shown to lead to the production of 6,7-anhydroerythromycin C (Donadio S. et al., *Proc. Natl. Acad. Sci. USA*, vol. 90, pp. 7119–7123 (1993)). International Application WO 93/13663, which is incorporated herein by reference in its entirety, describes additional types of DEBS gene manipulation that are capable of producing altered polyketides. However, many such attempts have been reported unproductive (Hutchinson C. R. and Fujii, I., *Annu. Rev. Microbiol.*, vol. 49, pp. 201–238, at p. 231 (1995)).

The complete DNA sequence has been disclosed for the genes from *Streptomyces hygroscopicus* that encode the modular Type I PKS governing the biosynthesis of rapamycin, a macrocyclic immunosuppressant polyketide (Schwecke, T. et al., *Proc. Natl. Acad. Sci. USA*, vol. 92, pp.7839–7843 (1995)). This DNA sequence has been deposited in the EMBUGenbank Database under the accession number X86780.

DNA sequences have also been disclosed for several Type I PKS gene clusters that govern the production of 16-membered macrolide polyketides, including the tylosin PKS from *Streptomyces fradiae* (EP 0 791 655 A2), the niddamycin PKS from *Streptomyces caelestis* (Kavakas, S. J. et al., *J. Bacteriol.*, vol. 179, pp. 7515–7522 (1998)) and the spiramycin PKS from *Streptomyces ambofaciens* (EP 0 791 655 A2). The loading modules of these PKS gene clusters differ from the loading modules of DEBS and of the avermectin PKS in that they include a domain resembling the KS domains of the extension modules in addition to the usual AT domain and ACP. The additional N-terminal KS-like domain has been named KSq, because it differs in each case from an extension KS by possessing a glutamine residue (Q in single letter notation) in place of the active site cysteine residue essential for β-ketoacyl-ACP synthase activity. The abbreviation ATq is used here simply to distinguish the AT domains found immediately C-terminal of KSq from extension AT's; the label has no other significance.

The PKS's for certain 14-membered macrolides (particularly, the oleandomycin PKS from *Streptomyces antibioticus*) and also the PKS's for certain polyether ionophore polyketides (particularly, the putative monensin PKS from *Streptomyces cinnamonensis*), similarly possess a loading domain comprising a KSq domain, an ATq domain and an ACP.

The KSq domain of the tylosin PKS and the associated ATq domain together are responsible for the highly specific production of propionate starter units. That is, the ATq is specific for the loading of methylmalonyl-CoA, and the KSq is responsible for the highly specific decarboxylation of the enzyme-bound methylmalonate unit to form a propionate unit. This proprionate unit is attached to the ACP domain of the loading module and appropriately placed to be transferred to the KS of extension module 1 for the initiation of chain extension. In a like manner, the ATq and the adjacent KSq of the spiramycin and niddamycin PKS's are responsible for the specific loading of malonate units and for their subsequent specific decarboxylation to provide acetate starter units for polyketide chain extension.

The second class of PKS, designated Type II, includes the synthases for aromatic compounds. Type II PKS's contain a single set of enzymatic activities for chain extension, and these are re-used as appropriate in successive cycles (Bibb, M. J. et al., *EMBO J.*, vol. 8, pp. 2727–2736 (1989); Sherman, D. H. et al., *EMBO J.*, vol. 8, pp. 2717–2725 (1989); Fernandez-Moreno, M. A. et al.,*J. Biol. Chem.*, vol. 267, pp. 19278–19290 (1992)). The "extender" units for the Type II PKS's are usually acetate units. The presence of specific cyclases dictates the preferred pathway for cyclisation of the completed chain into an aromatic product (Hutchinson, C. R. and Fujii, I., *Annu. Rev. Microbiol.*, vol. 49, pp. 201–238 (1995)).

The minimal number of domains required for polyketide chain extension on a Type 11 PKS when expressed in a *S. coelicolor* host cell has been defined, as for example in International Application WO 95/08548, as containing the following three polypeptides, which are products of the actI genes: (1) a KS; (2) a polypeptide termed the CLF, with end-to-end amino acid sequence similarity to the KS, but in which the essential active-site residue of the KS, a cysteine residue, is substituted either by a glutamine residue or, in the case of the PKS for a spore pigment such as the whiE gene product (Chater, K. F. and Davis, N. K., *Mol. Microbiol.*, vol. 4, pp. 1679–1691 (1990)), by a glutamic acid residue; and (3) an ACP.

Hybrid polyketides have been obtained by the introduction of clones containing DNA coding for one Type II PKS into another strain containing a different Type II PKS gene cluster. For example, DNA derived from the gene cluster for actinorhodin, a blue-pigmented polyketide from *S. coelicolor*, has been introduced into an anthraquinone polyketide-producing strain of *Streptomyces galileus* (Bartel, P. L. et al., *J. Bacteriol.*, vol. 172, pp. 4816–4826 (1990)).

In addition, International Application WO 95/08548 describes the production of hybrid polyketides by replacement of actinorhodin PKS genes with heterologous DNA from other Type II PKS gene clusters. International Application WO 95/08548 also describes the construction of a strain of *S. coelicolor* that substantially lacks the native gene cluster for actinorhodin, and the use in that strain of a plasmid vector pRM5 derived from the low-copy number vector SCP2* isolated from *S. coelicolor* (Bibb, M. J. and Hopwood, D. A., *J. Gen. Microbiol.*, vol. 126, p. $4^27$ (1981)) and in which heterologous PKS-encoding DNA may be expressed under the control of the divergent actI/actIII promoter region of the actinorhodin gene cluster (Fernandez-Moreno, M. A. et al., *J. Biol. Chem.*, vol. 267, pp. 19278–19290 (1992)). The plasmid pRM5 also contains DNA from the actinorhodin biosynthetic gene cluster encoding the gene for a specific activator protein, ActII-orf4. The ActiI-orf4 protein is required for transcription of the genes placed under the control of the actI/actII bidirectional promoter and activates gene expression during the transition from growth to stationary phase in the vegetative mycelium (Hallam, S. E. et al., *Gene*, vol. 74, pp. 305–320 (1988)).

Type II clusters in Streptomyces are known to be activated by pathway-specific activator genes (Narva, K. E. and Feitelson, J. S., *J. Bacteriol.*, vol. 172, pp. 326–333 (1990); Stutzman-Engwall, K. J. et al., *J. Bacteriol.*, vol. 174, pp. 144–154 (1992); Fernandez-Moreno, M. A. et al., *Cell*, vol. 66, pp. 769–780 (1991); Takano, E. et al., *Mol. Microbiol.*, vol. 6, pp. 2797–2804 (1992); Takano, E. et al., *Mol. Microbiol.*, vol. 7, pp. 837–845 (1992)). The Dnrl gene product complements a mutation in the actII-orf4 gene of *S. coelicolor*, implying that Dnrl and ActII-orf4 proteins act on similar targets. A gene (srmR) has been described (EP 0 524 832 A2) that is located near the Type I PKS gene cluster for the macrolide polyketide spiramycin. This gene specifically activates the production of the macrolide antibiotic spiramycin, but no other examples have been found of such a gene. Also, no homologues of the ActII-orf4/Dnrl/RedD family of activators have been described that act on Type I PKS genes.

International Application WO 98/01571, PUBLISHED Jan. 15, 1998; International Application WO 98/01546, PUBLISHED Jan. 15, 1998; International Application WO 99/35156, PUBLISHED Jul. 15, 1999; and WO 99/35157, published Jul. 15, 1999, describe the construction of hybrid PKS gene assemblies and the use of such assemblies to provide a variety of polyketides useful as starting materials for the preparation of the compounds of the present invention. For example, International Application WO 98/01546, PUBLISHED Jan. 15, 1998, describes in general terms the production of a hybrid PKS gene assembly comprising a loading module and at least one extension module. PKS gene modules can be treated as building blocks for the construction of enzyme systems, and thus novel erythromycin products, of desired types. This generally involves the cutting out and assembly of modules and multi-module groupings. Logical places for making and breaking intermodular connections are in the linking regions between modules. However, it may be preferable to make cuts and joins actually within domains (i.e., the enzyme-coding portions), close to the edges thereof. The DNA is highly conserved here among all modular PKS's, and this may aid in the construction of hybrids that can be transcribed. It also may assist in maintaining the spacing of the active sites of the encoded enzymes, which can be important. For example, International Application WO 98/01571, PUBLISHED Jan. 15, 1998, describes production of a hybrid gene by replacement of the ery loading module with an avr loading module, in which the ery module together with a small amount of the following KS domain is removed. The start of the KS domain (well spaced from the active site) is highly conserved and therefore provides a suitable splicing site as an alternative to the linker region between the loading domain and the start of the KS domain. The excised ery module is then replaced by an avr loading module.

In fact, when substituting a loading module, it may be desirable to replace not just the loading module domains (generally AT and ACP), but also the KS at the start of the following extension module. Typically, the excised loading module would have provided a propionate starter, and the replacement is intended to provide one or more different starters. Propionate, however, may feed into the KS of the extension module from a propionate pool in the host cell, leading to dilution of the desired products. This can largely be prevented by substituting an extended loading module that includes all or most of the KS domain. The splice site may be in the end region of the KS gene, early in the following AT gene or in the linker region between them.

Different types of hybrid PKS gene assemblies can be constructed, to provide a corresponding variety of novel polyketides useful as starting materials in the present invention. For example, International Application WO 98/01546, PUBLISHED Jan. 15, 1998, describes construction of a hybrid PKS gene assembly containing a wide-specificity loading module (see also Marsden, A. F. A. et al., *Science*, vol. 279, pp. 199–202 (1998)). In particular, International Application WO 98/01546, PUBLISHED Jan. 15, 1998, describes grafting of the wide-specificity avr loading module onto the first multienzyme component of DEBS in place of the normal loading module. International Application WO 98/01571, PUBLISHED Jan. 15, 1998, describes certain novel polyketides that can be prepared using this hybrid PKS gene assembly.

Patent Application WO 98/01546, PUBLISHED Jan. 15, 1998, further describes the construction of a hybrid PKS gene assembly by grafting of the loading module for the rapamycin PKS onto the first multienzyme component of DEBS in place of the normal loading module. The loading module of the rapamycin PKS differs from the loading modules of DEBS and the avermectin PKS in that it comprises a CoA ligase domain, an enoylreductase ("ER")

domain and an ACP. Suitable organic acids including the natural starter unit 3,4-dihydroxycyclohexane carboxylic acid may be activated in situ on the PKS loading domain, with or without reduction by the ER domain transferred to the ACP for intramolecular loading of the KS of extension module 1.

International Application WO 98/01571, PUBLISHED Jan. 15, 1998, teaches that it is possible to determine the specificity of the natural loading module for unnatural starter units and to use a loading module with relaxed specificity to generate novel polyketides. Thus, International Application WO 98/01571, PUBLISHED Jan. 15, 1998, describes the unexpected ability of the ery loading module to incorporate unnatural carboxylic acids and derivatives thereof to produce novel erythromycins in erythromycin-producing strains containing only DEBS genes.

One may also make alterations within a product polyketide by replacing an extension module with one that provides a ketide unit with a different oxidation state and/or with a different stereochemistry. It has generally been assumed that the stereochemistry of the methyl groups in the polyketide chain is determined by the AT. In fact, this stereochemistry is a feature of other. domains of the PKS and thus open to variation only by replacement of those domains, individually or by module replacement. Methyl and other substituents can be added or removed by AT domain replacement or total module replacement.

It is possible to combine the technique of extension-module replacement with the technique of loading-module replacement or the use of the relaxed substrate specificity of the ery loading module to produce a wide range of novel erythromycins. International Application WO 98/01571, PUBLISHED Jan. 15, 1998, describes the use of such techniques to produce novel erythromycins in non-transformed organisms. International Application WO 98/01571, PUBLISHED Jan. 15, 1998, also describes gene assemblies, vectors containing such gene assemblies, and transformant organisms that can express them to produce novel erythromycins.

International Application WO 00/00500, PUBLISHED Jan. 6, 2000, teaches that one may construct a hybrid PKS gene assembly by replacing the genetic material encoding the natural starter unit with genes coding for a desirable starter unit. This technique can be used to prepare 14-membered macrolides with the desired starter unit, while minimizing the formation of by-products containing a different starter unit. In particular, International Application WO 00/00500, PUBLISHED Jan. 6, 2000, discloses a method of synthesizing novel, 14-membered polyketides having substantially exclusively an acetate starter unit by providing a PKS multienzyme incorporating a loading module of the form KSq-ATq-ACP that specifically provides the desired acetate starter unit. This method may comprise providing nucleic acid encoding the PKS multienzyme and introducing it into an organism where it can be expressed. In addition, additional methods may be disclosed in WO 00/00618, published Jan. 6, 2000, which is herein incorporated by reference.

In the loading module of the type KSq-ATq-ACP, the domains or portions of them may be derived from the same or from different sources and may comprise either natural or engineered domains. For example, the ATq domain can be replaced by an AT domain derived from any extension module of a Type I PKS having specificity for the loading of malonate units, so long as the KSq domain is chosen to have a matching specificity towards malonate units. Particularly suitable for this purpose are components of the PKS's for the biosynthesis of erythromycin, methylmycin, oleandomycin, tylosin, spiramycin, midecamycin and niddamycin, for all of which the gene and modular organization is known at least in part. Particularly suitable sources of the genes encoding a loading module of the type KSq-ATq-ACP are the loading modules of oleandomycin, spiramycin, niddamycin, methylmycin and monensin, which are specific for the loading of malonate units that are subsequently decarboxylated to acetate starter units.

Alternatively, International Application WO 00/00500, PUBLISHED Jan. 6, 2000, teaches that the KSq domain in a loading module of the type KSq-ATq-ACP may be substituted by a CLF polypeptide of a Type II PKS. The CLF, in addition to any other activities that it may possess, is an analogue of the KSq domain and can act as a decarboxylase toward bound malonate units.

The loading module of the type KSq-ATq-ACP may be linked to a hybrid PKS produced for example as in International Applications WO 98/01546, PUBLISHED Jan. 15, 1998, and WO 98/01571, PUBLISHED Jan. 15, 1998. It is particularly useful to link such a loading module to gene assemblies encoding hybrid PKS's that produce novel derivatives of 14-membered macrolides.

As described in, for example, International Application WO 98/01546, PUBLISHED Jan. 15, 1998, the production of novel polyketides for use as starting materials in the present invention may also involve the use of transformant organisms that are capable of modifying the initial products, e.g., by carrying out all or some of the biosynthetic modifications normal in the production of erythromycins. Use may be made of mutant organisms in which some of the normal pathways are blocked, e.g., to produce products without one or more "natural" hydroxy groups or sugar groups. See, for instance, International Application WO 91/16334 or Weber et al., *J. Bacteriol.*, vol. 164, pp. 425–433 (1985), both of which are incorporated herein by reference in their entirety. Alternatively, use may be made of organisms in which some of the normal pathways are overexpressed, to overcome potential rate-limiting steps in the production of the desired product. See, for example, International Application WO 97/06266, which is incorporated herein by reference in its entirety.

International Application WO 98/01571, PUBLISHED Jan. 15, 1998; International Application WO 98/01546, PUBLISHED Jan. 15, 1998; International Application WO 99/35156, PUBLISHED Jul. 15, 1999; WO 99/35157 and International Application WO 00/00500, PUBLISHED Jan. 6, 2000, describe a variety of novel erythromycin analogues obtainable by means of the previous aspects. These applications also describe methods for the production of such novel polyketides. In the simplest method, unnatural starter units (preferably; but not restricted to the carboxylic acid analogues of the unnatural starter units) are introduced to untransformed organisms that are capable of producing erythromycins. A preferred approach involves the introduction of a starter unit into a fermentation broth of an erythromycin-producing organism. This approach is more effective for transformed organisms capable of producing erythromycins. Alternatively, the starter unit analogue can be introduced to preparations of untransformed or transformed erythromycin-producing organisms, for example, fractionated or unfractionated broken-cell preparations.

In another method, one or more segments of DNA encoding individual modules or domains within a heterologous Type I PKS (the "donor" PKS) may be used to replace the DNA encoding individual modules or domains, respectively, within the DEBS genes of an erythromycin-producing organism. Loading modules and extension modules drawn from natural or non-natural PKS's are suitable for this "donor" PKS. Particularly suitable for this purpose are components of the Type I PKS's for the biosynthesis of erythromycin, rapamycin, avermectin, tetronasin, oleandomycin, monensin, amphotericin and rifamycin, for which the gene and modular organization is known through gene sequence analysis, at least in part. Particularly favorable examples of the loading modules of the donor PKS are loading modules showing a relaxed specificity, for example, the(loading module of the avermectin-producing PKS of Streptomyces avermitilis; loading modules possessing an unusual specificity, for example, the loading modules of the rapamycin-, FK506- and ascomycin-producing PKS's, all of which naturally accept a shikimate-derived starter unit; or loading modules that preferentially yield polypeptides with a desired starter unit such as acetate, for example, loading modules of the type KSq-ATq-ACP. Unexpectedly, when cultured under suitable conditions, both the untransformed and genetically engineered erythromycin-producing organisms have been found to produce non-natural erythromycins, and, where appropriate, the products are found to undergo the same processing as the natural erythromycin.

An additional method calls for the introduction of a plasmid containing "donor" PKS DNA into a host cell. The host cell may simply harbor the plasmid, or the plasmid may integrate into the genome of the cell. A plasmid with an int sequence will integrate into a specific attachment site (att) of a host's chromosome. Thus, International Application WO 98/01571, PUBLISHED Jan. 15, 1998, describes integration of such a plasmid into the DEBS genes on the chromosome of the erythromycin-producing strain by homologous recombination, to create a hybrid PKS. A preferred embodiment is when the donor PKS DNA includes a segment encoding a loading module in such a way that this loading module becomes linked to the DEBS genes on the chromosome. Such a hybrid PKS produces valuable and novel erythromycin products when cultured under suitable conditions as described by, for example, International Application WO 98/01571, PUBLISHED Jan. 15, 1998. To illustrate, when the DEBS loading module is replaced by the avr loading module, the novel erythromycin products contain a starter unit typical of those used by the avermectin PKS.

International Application WO 98/01571, PUBLISHED Jan. 15, 1998, describes the unexpected and surprising finding that transcription of any of the hybrid erythromycin genes can be specifically and significantly increased when the hybrid genes are placed under the control of a promoter for a Type II PKS gene linked to a specific activator gene for that promoter. Such specific increases in the yield of a valuable erythromycin product are also seen for natural erythromycin PKS placed under the control of a Type II PKS promoter and activator gene.

In one embodiment, desired genes present on an SCP2*-derived plasmid are placed under the control of the bidirectional acti promoter derived from the actinorhodin biosynthetic gene cluster of S. coelicolor. In this embodiment, the vector also contains the structural gene encoding the specific activator protein ActI-orf4. The recombinant plasmid is introduced into S. erythraea under conditions where either the introduced PKS genes, or PKS genes already present in the host strain, are expressed under the control of the acti promoter. Such strains produce the desired erythromycin product, and the activator gene requires only the presence of the specific promoter in order to enhance transcriptional efficiency from the promoter.

The recombinant strains can produce levels of erythromycin product more than ten times those produced when the same PKS genes are under the control of the natural promoter. The specific erythromycin product is also produced precociously in growing culture, rather than only during the transition from growth to stationary phase. Thus, when the genetically engineered cell is S. erythraea, the activator and promoter are derived from the actinorhodin PKS gene cluster, and the actI/actI/-orf4-regulated ery PKS gene cluster is housed in the chromosome following the site-specific integration of a low copy-number plasmid vector, culturing of the cells under suitable conditions can produce more than ten times the amount of 14-membered macrolide product produced by a comparable strain not under such heterologous control. When in such a genetically engineered cell the PKS genes under this heterologous control are hybrid Type I PKS genes whose construction is described herein, more than ten-fold hybrid polyketide product can be obtained compared to the same hybrid Type I PKS genes not under such control. Specifically, when the hybrid Type I PKS gene cluster is DEBS in which the ery loading module has been replaced by the avr loading module, a ten-fold increase is found in the total amounts of novel 14-membered macrolides produced by the genetically engineered cells when cultured under suitable conditions as described in International Application WO 98/01571, PUBLISHED Jan. 15, 1998.

Suitable and preferred means for growing the untransformed and genetically-engineered erythromycin-producing cells, and suitable and preferred means for the isolation, identification and practical utility of the novel erythromycins are described more fully in, for example, International Application WO 98/01571, PUBLISHED Jan. 15, 1998.

Untransformed or transformed organisms useful in the methods described above and capable of producing erythromycins include but are not limited to Saccharopolyspora species, *Streptomyces griseoplanus*, Nocardia sp., Micromonospora sp., Arthobacter sp., and *S. antibioticus*, but excluding *S. coelicolor*. Particularly suitable in this regard are untransformed and transformed strains of *S. erythraea*, for example NRRL 2338, 18643, 21484. Preferred transformed strains are those in which the erythromycin loading module has been replaced with the loading module from the avermectin producer, *S. avermitilis*, or the rapamycin producer, *S. hygroscopicus*.

The preferred method for producing starting compounds for the current invention requires fermentation of the appropriate organism in the presence of the appropriate carboxylic acid of the formula $R^{17}CO_2H$, wherein $R^{17}$ is as defined in claim 1. The carboxylic acid is added to the fermentation either at the time of inoculation or at intervals during the fermentation. Production of polyketides that may be useful in the preparation of the compounds of this invention may be monitored by removing samples from the fermentation, extracting with an organic solvent and following the appearance of the starting compounds by chromatography, such as high-pressure liquid chromatography. Incubation is continued until the yield of the starting compound has been maximized, generally for a period of 4 to 10 days. A preferred level of each addition of the carboxylic acid or derivative thereof is between 0.05 and 4.0 g/L. The best yields of the starting compounds are generally obtained by gradually adding the acid or derivative to the fermentation, for example by daily addition over a period of several days.

The preparation of the compounds of the present invention is illustrated in Schemes 1 to 20 below.

Scheme 1

Scheme 1 describes the general synthesis of compounds of formula I wherein X is —C(=N—$OR^8$)— or —CH($NR^8R^9$)—. Starting compounds of formula 2 can be prepared from 13-methyl erythromycin A by a variety of synthetic routes using conventional methods known to those skilled in the art. Treatment of compounds of formula 2 with $R^8O.NH_2HCl$ in the presence of a base such as triethylamine or pyridine can afford compounds of formula 3. Reduction of compounds of formula 3, wherein $R^8$ is H, with a reducing agent or by catalytic hydrogenation can provide amines of formula 4, which can be converted to compounds of formula 5 via reductive alkylation or direct alkylation.

SCHEME 1

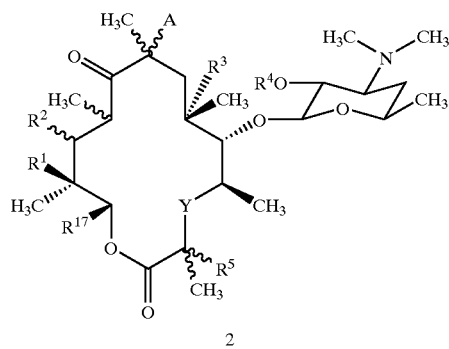

2

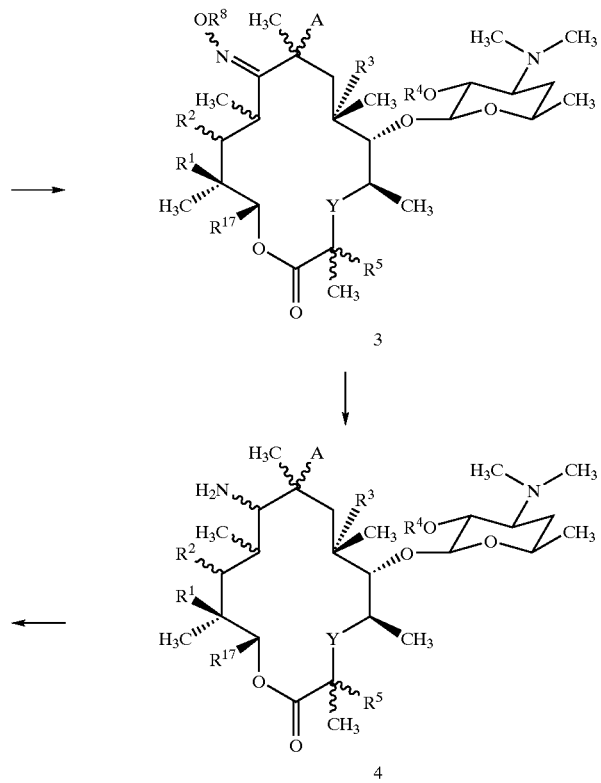

3

4

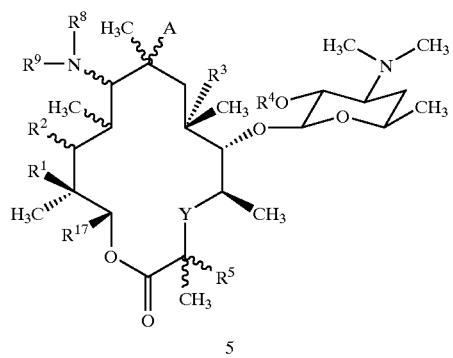

5

The medium used for the fermentation may be a conventional complex medium containing assimilable sources of carbon, nitrogen and trace elements.

It should be understood that the methods for preparing starting materials as described in International Application WO 98/01571, PUBLISHED Jan. 15, 1998; International Application WO 98/01546, PUBLISHED Jan. 15, 1998; International Application WO 99/35156, PUBLISHED Jul. 15, 1999; WO 99/35157 and International Application WO 00/00500, PUBLISHED Jan. 6, 2000, are not limited to the specific detail of the examples in those applications.

Scheme 2

Scheme 2 describes the synthesis of compounds of formula 1 wherein X is $NR^9CHR^8$—. Starting compounds of formula 6 can be made according to Scheme 1. Compounds of formula 6 can be converted to those of formula 8 via compounds of formula 7 by means of Beckmann rearrangement as described by Yamamoto et al. (see B. M. Trost, Comprehensive Organic Transformations, vol. 4, pp. 763–794 (hereinafter "Trost"); Yamamoto et al., J. Amer. Chem. Soc., p. 7368 (1981) (hereinafter "Yamamoto 1981")). Compounds of formula 8 wherein $R^8$ is hydrogen can be made by following substantially the same procedures as those of Yamamoto et al., *Tetrahedron Letters*, vol. 24, p. 4711 (1983) (hereinafter "Yamamoto 1983"). Compounds of formula 8 can undergo reductive alkylation or direct alkylation to afford those of formula 9.

SCHEME 2

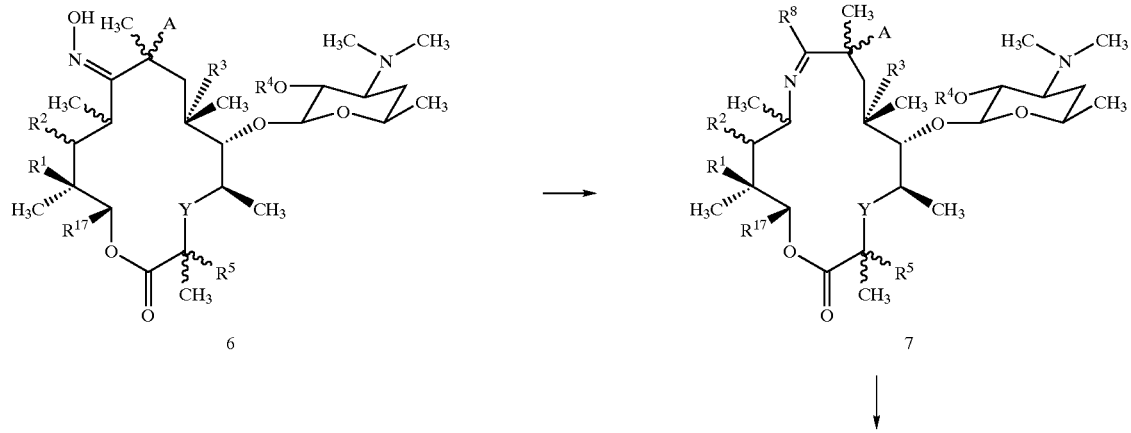

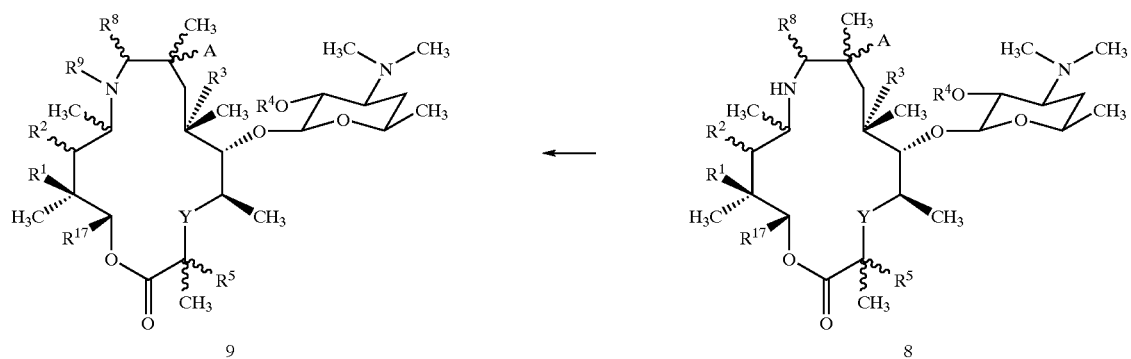

Scheme 3

Scheme 3 describes the synthesis of compounds of formula 1 wherein X is —$CHR^8NR^9$—. Starting compounds of formula 10 can be made according to Scheme 1 or prepared from the oxime of formula 6 via base-induced epimerization (see R. R. Wilkening et al., *Bioorganic & Med. Chem. Lett.*, vol. 3, pp. 1287–1292 (1993) (hereinafter "Wilkening")). Compounds of formula 10 can be converted to those of formula 12 via compounds of formula 11 by means of Beckmann rearrangement as described by Yamamoto et al. (see *Trost*, pp. 763–794; *Yamamoto* 1981, p. 7368). Compounds of formula 12 wherein $R^8$ is hydrogen can be made by following substantially the same procedures as those of *Yamamoto* 1983, p. 4711. Compounds of formula 12 can undergo reductive alkylation or direct alkylation to afford compounds of formula 13.

SCHEME 3

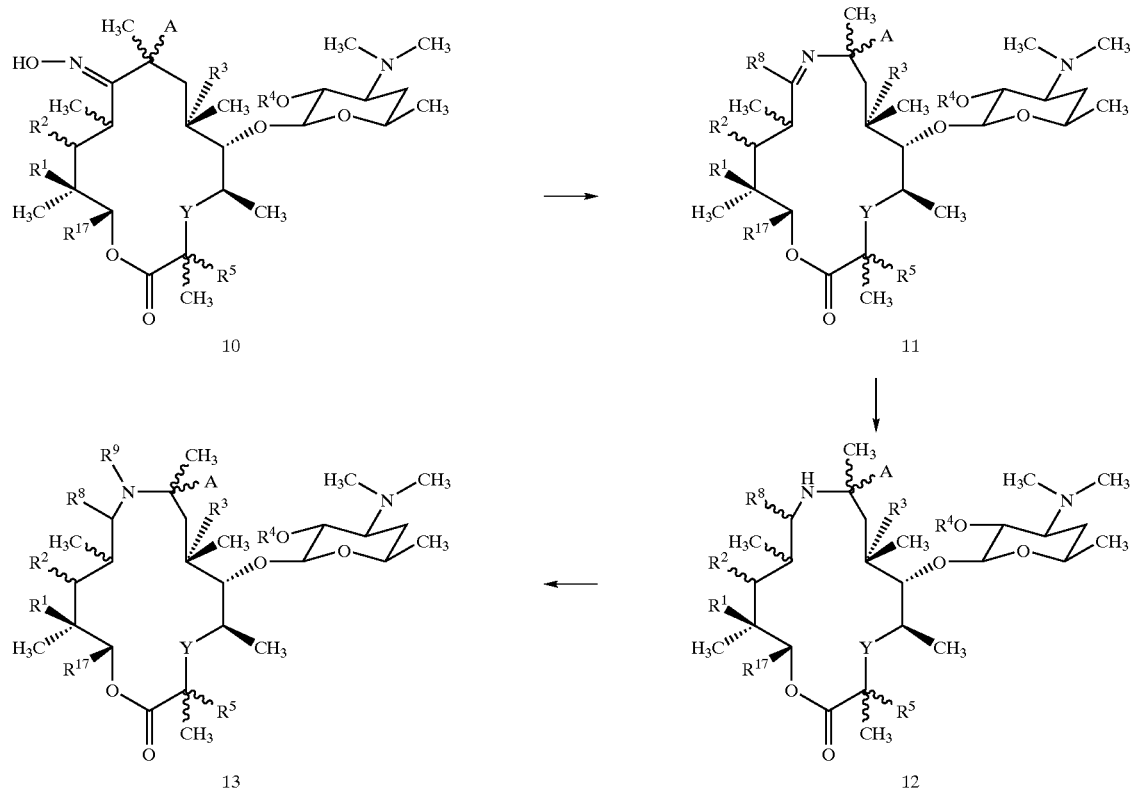

Scheme 4

Scheme 4 describes the synthesis of compounds of formula 1 wherein X is —NR$^9$CH$_2$—. The starting compound of formula 14 can be made from 13-methyl erythromycin A according to Scheme 1. The transformation of the compound of formula 14 to those of formula 17 can be done by following substantially the same procedures as those described by S. Djokic et al., *J. Chem. Soc., Perkin Trans.* I, pp. 1881–1890 (1986), and M. Bright et al., *J. Antibiotics*, vol. 41, p. 1029 (1998). The compound of formula 15 can be obtained from that of formula 14 via Beckmann rearrangement. Reduction of the compound of formula 15 can provide that of formula 16, which can undergo reductive alkylation or direct alkylation to afford the compounds of formula 17. Compounds of formula 18 can be prepared from those of formula 17 by a variety of synthetic routes using conventional methods known to those skilled in the art.

SCHEME 4

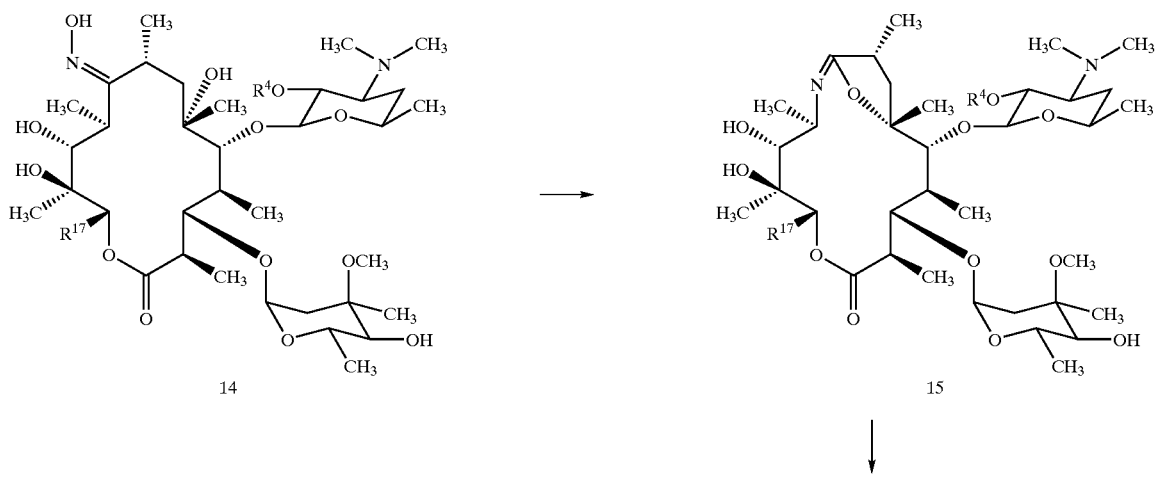

-continued

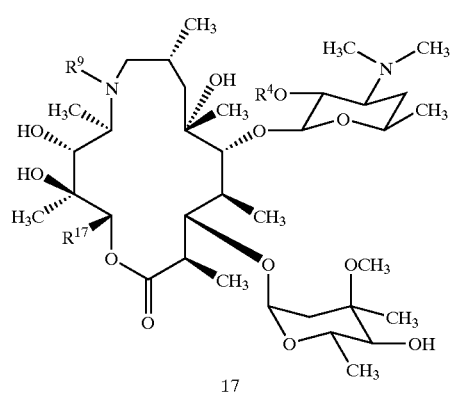

17

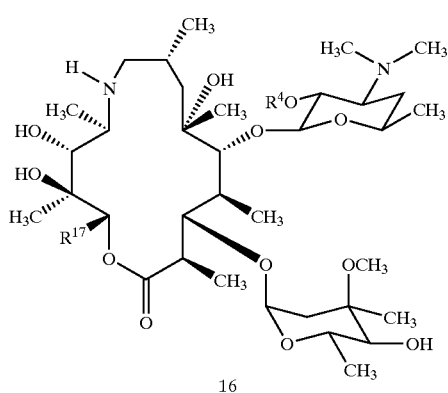

16 several steps ↓

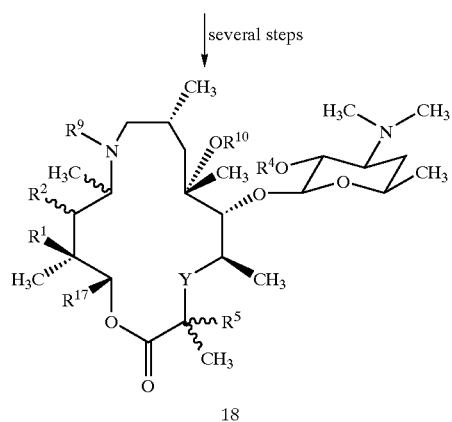

18

Scheme 5

Scheme 5 describes another synthesis of compounds of formula 1 wherein X is —NR⁹CH₂—. Starting compounds of formula 19 wherein $R^{10}$ is not hydrogen can be made from 13-methyl erythromycin A according to Scheme 8 as described below. The transformation of compounds of formula 19 to those of formula 22 can be achieved by following substantially the same procedures as those described by A. Dennis et al., *Bioorganic & Med. Chem. Lett.*, pp. 2427–2432 (1998), and S. T. Waddell et al., *Biorganic & Med. Chem. Lett.*, pp. 1321–1326 (1998). Compounds of formula 19 can undergo Beckmann rearrangement to provide those of formula 20, which can be reduced to afford the compounds of formula 21. Reductive alkylation or direct alkylation can generate the compounds of formula 22. The compounds of formula 18 can be made from those of formula 22 by a variety of synthetic routes using conventional methods known to those skilled in the art.

SCHEME 5

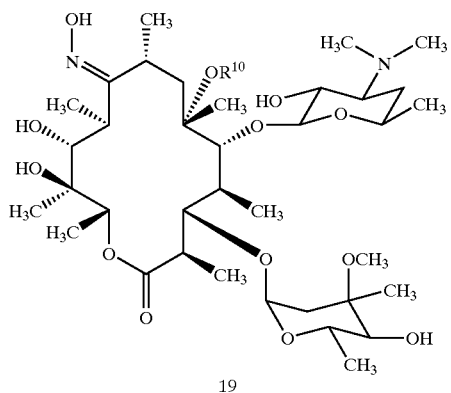

19

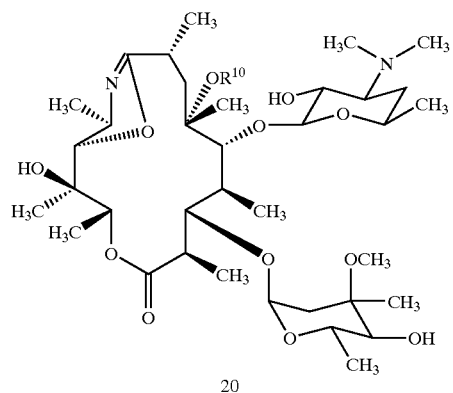

20

↓

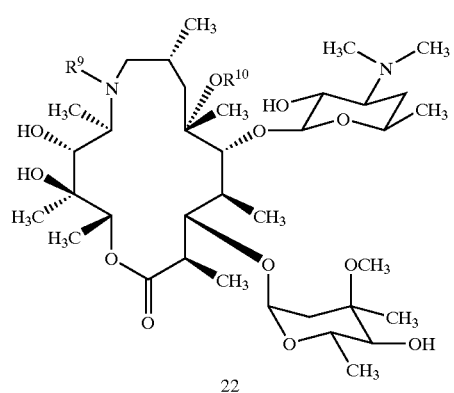

22

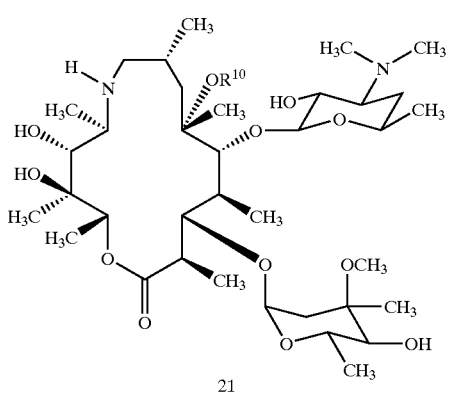

21

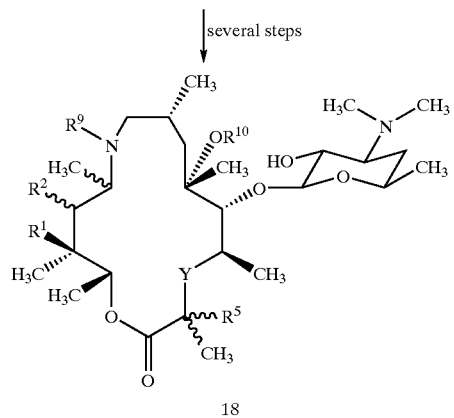

18

Scheme 6

Scheme 6 describes the synthesis of compounds of formula 1 wherein X is —CH$_2$NR$^9$—. The starting compound of formula 23 can be made from 13-methyl erythromycin A according to Scheme 1 or by base-initiated epimerization of the oxime of formula 14 (see *Wilkening*, pp. 1287–1292). The transformation of the compound of formula 23 to those of formula 27 can be accomplished by following substantially the same procedures as those described by *Wilkening*, pp. 1287–1292. Beckmann rearrangement of the compound of formula 23 can provide a mixture of the compounds of formulas 24 and 25, and both can be reduced to provide the compound of formula 26 by catalytic hydrogenation or by using a reducing agent. Reductive alkylation or direct alkylation of the compound of formula 26 leads to those of formula 27, which can be converted to the compounds of formula 28 by a variety of synthetic routes using conventional methods known to those skilled in the art.

SCHEME 6

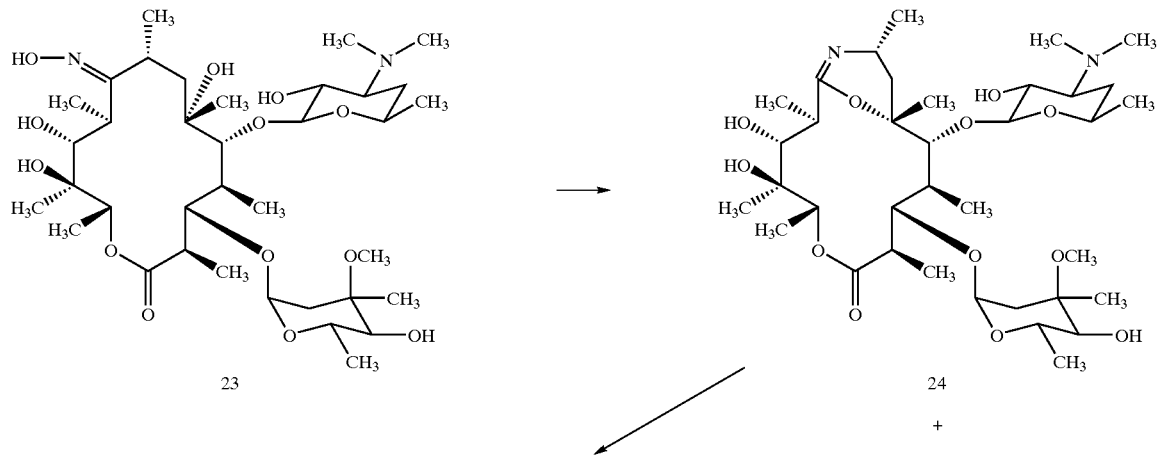

-continued

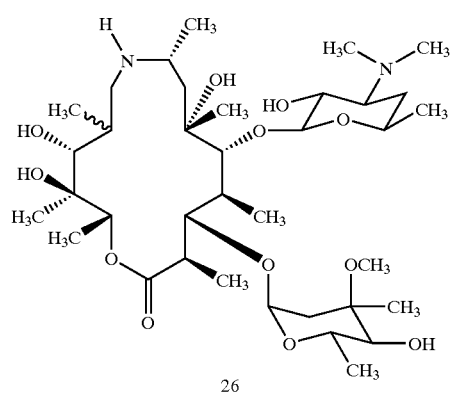
26

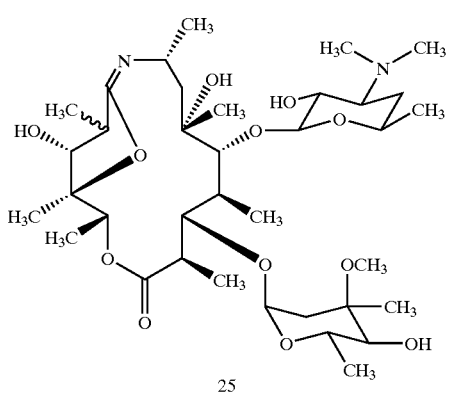
25

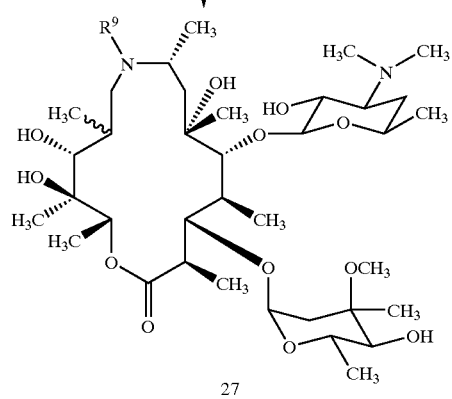
27

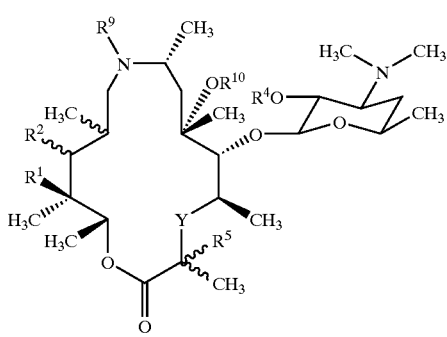
28

Scheme 7

Scheme 7 describes another synthesis of compounds of formula 1 wherein X is —$CH_2NR^9$—. Starting compounds of formula 29 wherein $R^{10}$ is not hydrogen can be made from 13-methyl erythromycin A according to Scheme 8 as described below, or by base-initiated epimerization of oximes of formula 19 wherein $R^{10}$ is not hydrogen (see Wilkening, pp. 1287–1292). The transformation of compounds of formula 29 to those of formula 33 can be accomplished by following substantially the same procedures as those described by Wilkening, pp. 1287–1292. Beckmann rearrangement of compounds of formula 29 can provide a mixture of the compounds of formulas 30 and 31, and both can be reduced to provide the compounds of formula 32 by catalytic hydrogenation or by using a reducing agent. Reductive alkylation or direct alkylation of the compounds of formula 32 leads to those of formula 33, which can be converted to the compounds of formula 28 by a variety of synthetic routes using conventional methods known to those skilled in the art.

SCHEME 7

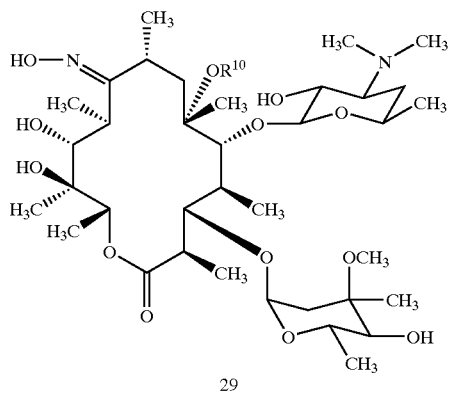
29

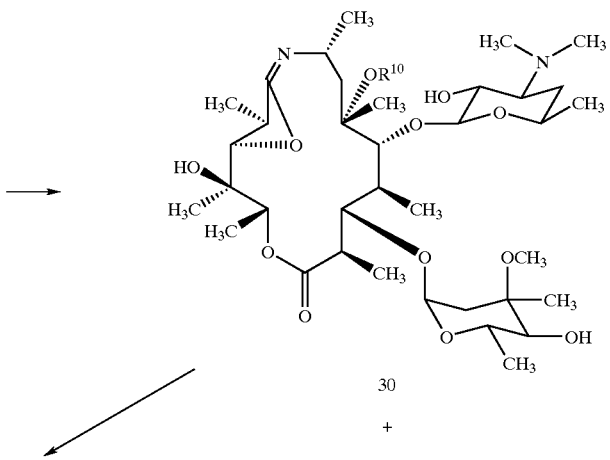
30

+

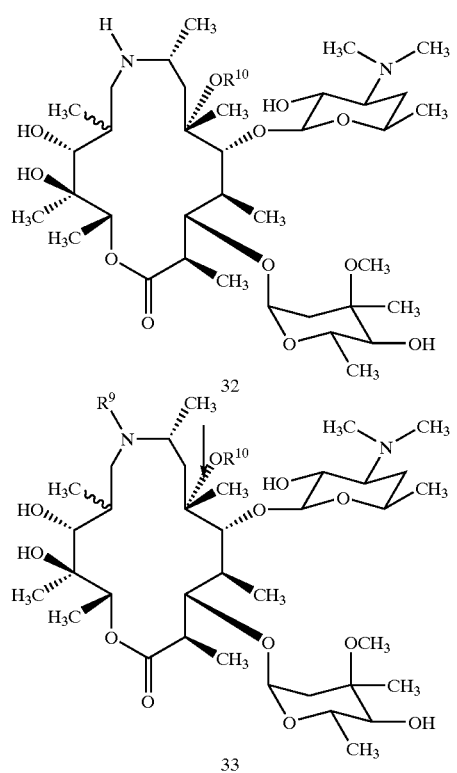

32

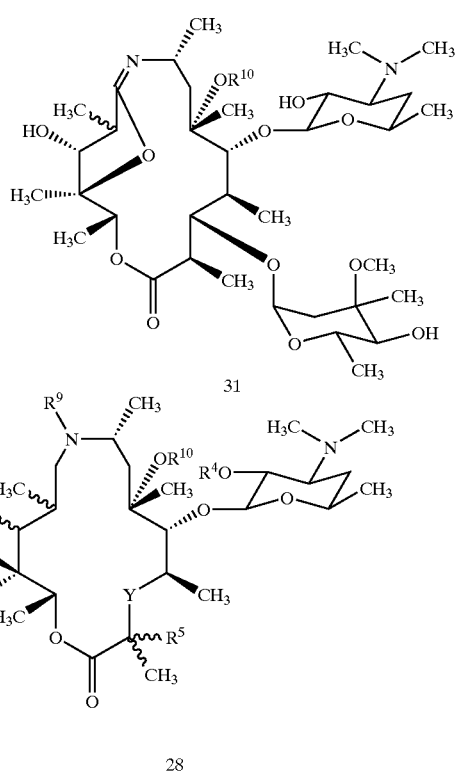

31

33

28 several steps →

Scheme 8

Scheme 8 outlines the synthesis of compounds of formula 1. The starting compound, the oxime of formula 14, can be made from 13-methyl erythromycin A according to Scheme 1. The transformation of the compound of formula 14 to those of formula 37 can be accomplished by following substantially the same procedures as those reported by Y. Watanabe et al., *J. Antibiotics*, pp. 1163–1167 (1993). The 9-oxime hydroxyl, 2' hydroxyl and 4' hydroxyl of the compound of formula 14 can be protected by using the methods summarized in T.W. Greene and P. G. M Wuts, *Protective Groups in Organic Synthesis. 2d Ed.*, John Wiley & Sons, pp. 10–142 (1992) (hereinafter "*Greene and Wuts*"), to provide compounds of formula 34, wherein $P^1$, $P^2$ and $P^3$ represent the same or different protecting groups. The preferred protecting groups are silyl ethers, such as trimethylsilyl ether, or esters, such as acetate or benzoate. Alkylation of the 6-hydroxyl of compounds of formula 34 can generate those of formula 35, which can be converted to compounds of formula 36 by means of deprotection following the methods summarized in *Greene and Wuts*, pp. 10–142. Deoximation of the compounds of formula 36 can provide those of formula 37. Compounds of formula 1 can be made from the compounds of formula 37 by a variety of synthetic routes using conventional methods known to those skilled in the art.

SCHEME 8

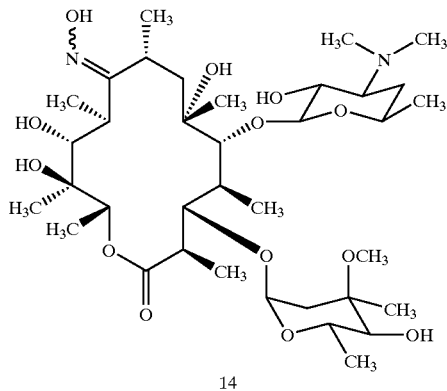

14

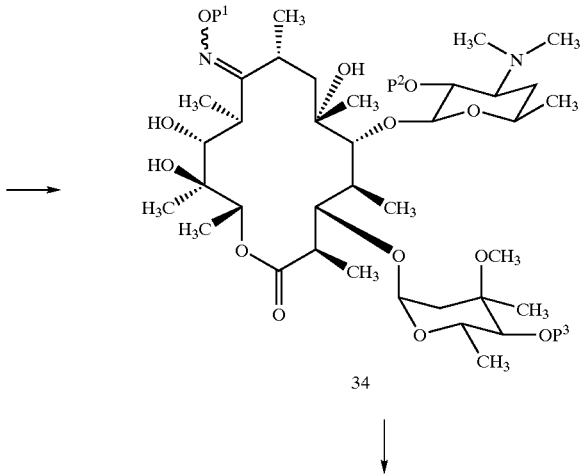

34

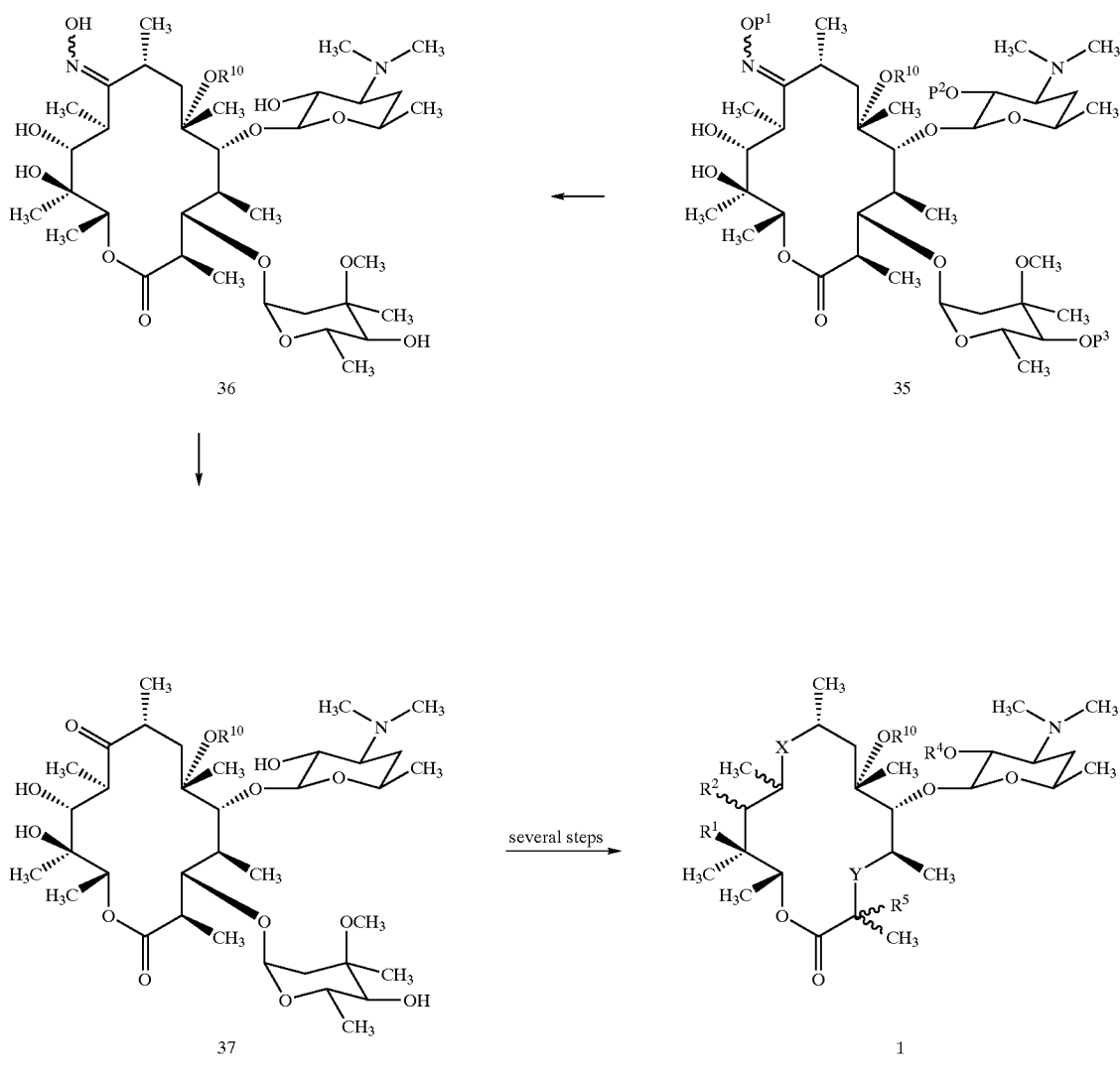

Scheme 9

Scheme 9 describes the synthesis of compounds of formula 1 wherein Y is CH(O—4"—O— acylated cladinose) as shown in formula 39. Starting compounds of formula 38 can be made from 13-methyl erythromycin A by a variety of methods known to those skilled in the art. The acylation of the compounds of formula 38 can be carried out to provide the compounds of formula 39 using conventional methods known to those skilled in the art. The acylation reactions may necessitate protection of other hydroxyl groups. This may be accomplished by protection as a silyl ether, an ester, a mixed carbonate or any of a variety of hydroxyl protecting groups well known to those skilled in the art.

SCHEME 9

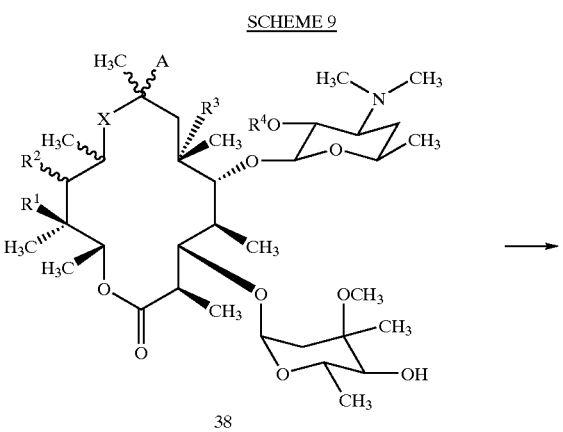

-continued

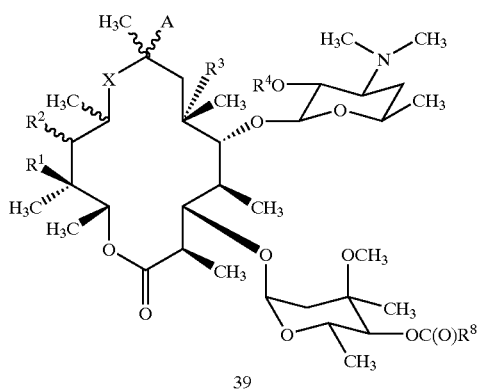
39

Scheme 10

Scheme 10 describes another synthesis of compounds of formula 1 wherein Y is CH(O—4"—O-acylated cladinose), as shown in formulas 41 and 42. Starting compounds of formula 38 can be made from 13-methyl erythromycin A by a variety of methods known to those skilled in the art. Acylation of compounds of formula 38 can be carried out to provide the compounds of formula 40, wherein L represents a leaving group such as mesyl, tosyl or halogen, using conventional methods known to those skilled in the art. The acylation reactions may necessitate protection of other hydroxyl groups. This may be accomplished by protection as a silyl ether, an ester, a mixed carbonate or any of a variety of hydroxyl protecting groups well known to those skilled in the art. Compounds of formula 40 can undergo nucleophilic substitution to provide the compounds of formulas 41 and 42 by using methods well known to those skilled in the art.

SCHEME 10

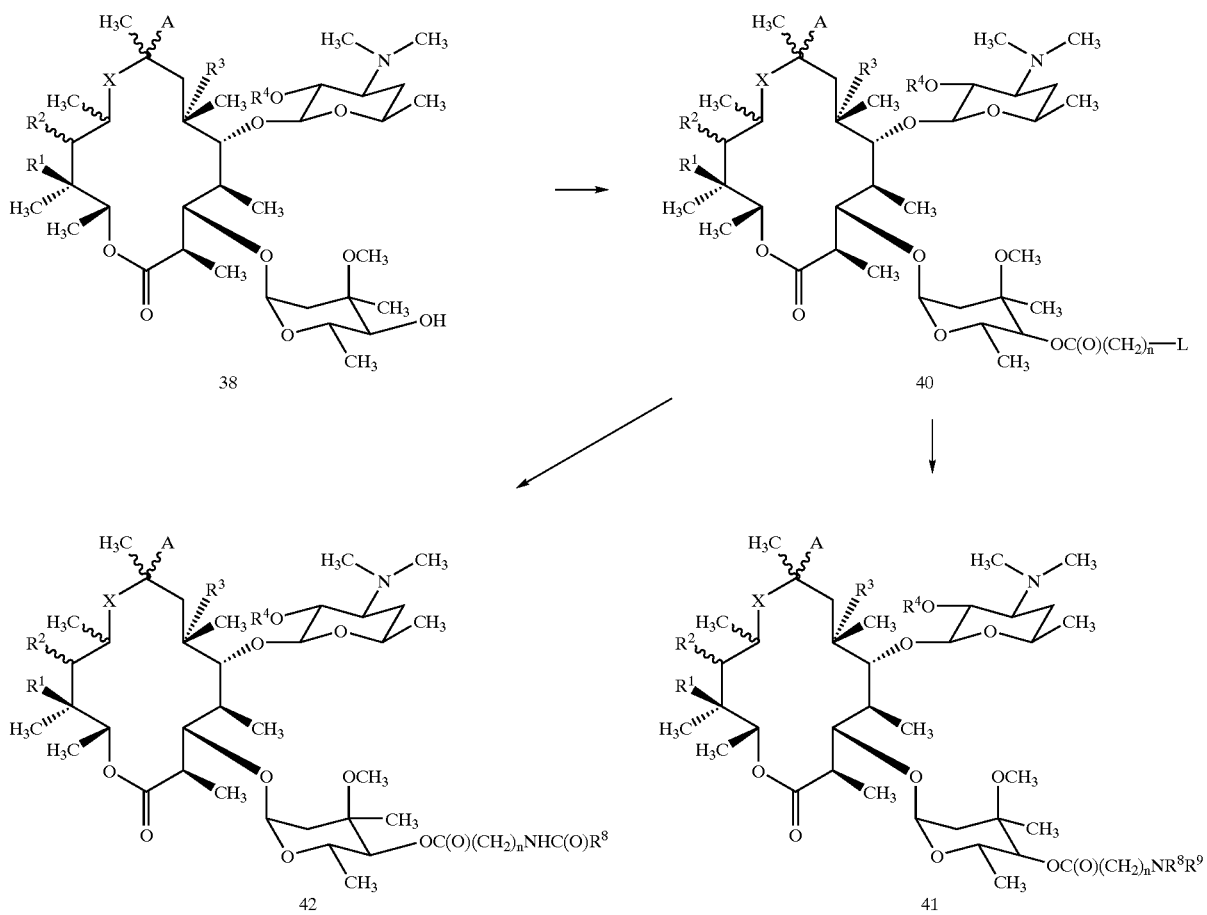

Scheme 11

Scheme 11 describes the synthesis of compounds of formula 1 wherein Y is CH(O—4"—O— carbamated cladinose) as shown in formulas 44, 45 and 46. Starting compounds of formula 38 can be made from 13-methyl erythromycin A by a variety of methods known to those skilled in the art. Treatment of compounds of formula 38 with carbonyldiimidazole and a base can provide compounds of formula 43. This reaction may necessitate the protection of other hydroxyl groups. This may be accomplished by protection as a silyl ether, an ester, a mixed carbonate or any of a variety of hydroxyl protecting groups well known to those skilled in the art. Compounds of formula 43 can be converted to those of formulas 44 and 45 by using methods well known to those skilled in the art. Reductive alkylation or direct alkylation of compounds of formula 45 can provide those of formula 46.

SCHEME 11

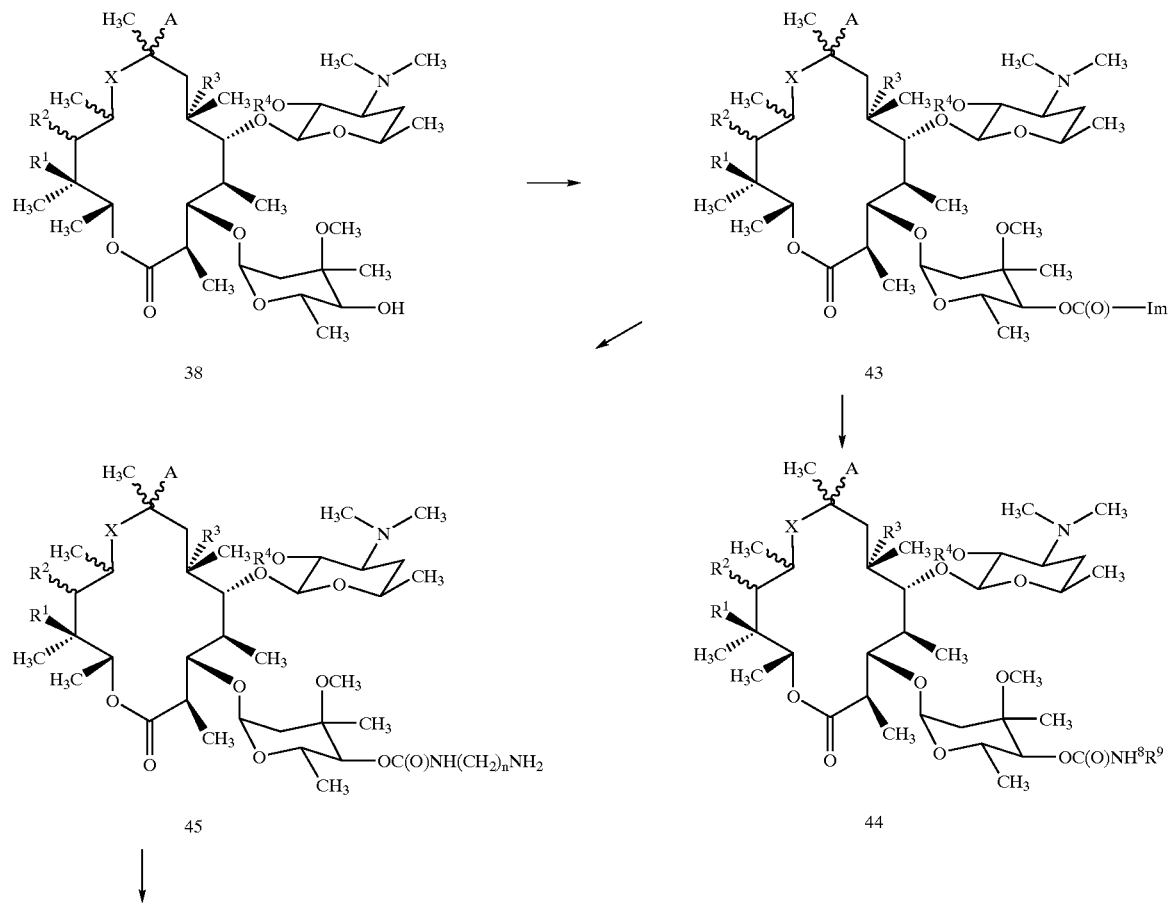

Scheme 12

Scheme 12 describes the synthesis of compounds of formula 1 wherein Y is CH(4"—substituted-3"-desmethoxy cladinose) as shown in formula 49. Starting compounds of formula 38 cam be made from 13-methyl erythromycin A by a variety of methods known to those skilled in the art. Oxidation of compounds of formula 38 using methods well known to those skilled in the art can provide compounds of formula 47 (see Yang et al., *J. Org. Chem.*, vol.61, pp.5149–5152 (1996) (hereinafter "*Yang*")). This oxidation reaction may necessitate the protection of other hydroxyl groups. This may be accomplished by protection as a silyl ether, an ester, a mixed carbonate or any of a variety of hydroxyl protecting groups well known to those skilled in the art. The 3" methoxy group can be removed by following substantially the same procedures as those described by *Yang*, pp. 5149–5152, to provide compounds of formula 48. Compounds of formula 48 can be converted to those of formula 49, wherein $R^{12}$ and $R^{13}$ are as defined previously, by using methods well known to those skilled in the art.

SCHEME 12

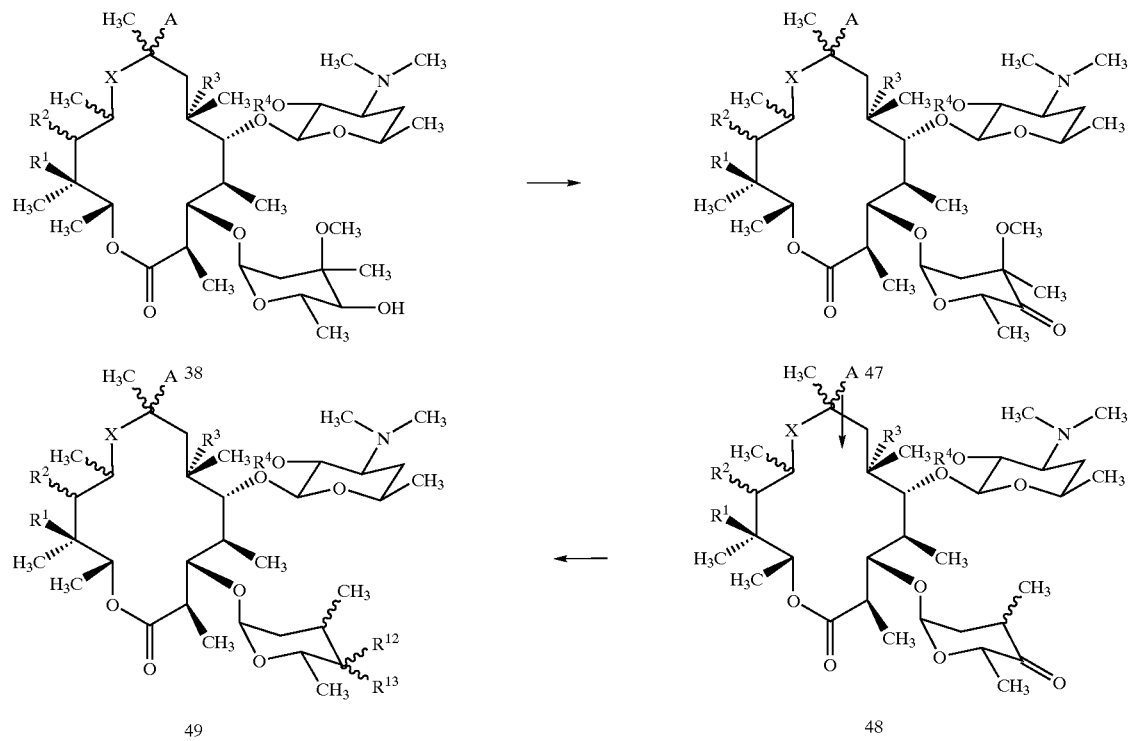

Scheme 13

Scheme 13 describes the synthesis of compounds of formula 1 wherein Y is CH(4"—substituted cladinose) as shown in formulas 54 and 55. Starting compounds of formula 47 are available from Scheme 12. Compounds of formula 47 can be converted to those of formula 52 by using methods well known to those skilled in the art. Epoxides of formula 50 can be formed by treating compounds of formula 47 with the sulfur ylides dimethyloxosulfonium methylide and dimethylsulfonium methylide summarized in J. March, *Advanced Organic Chemistry*. 4th Ed., John Wiley and Sons, pp. 974–975 (1992). Compounds of formula 51 can be converted to those of formula 53 via an epoxide-opening reaction with an azide reagent such as sodium azide. Reduction of compounds of formula 51 can provide compounds of formula 53, which can be converted to those of formulas 54 and 55 by using methods well known to those skilled in the art.

SCHEME 13

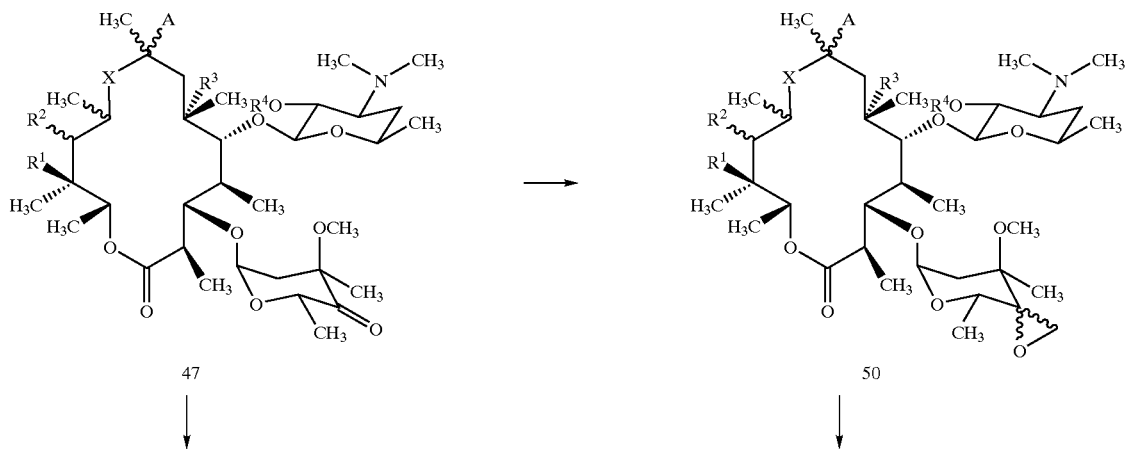

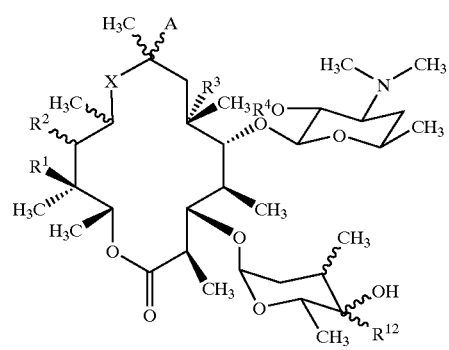

52

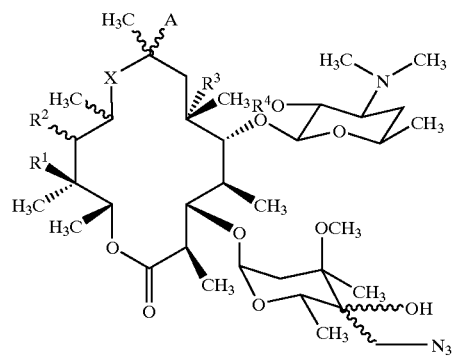

51

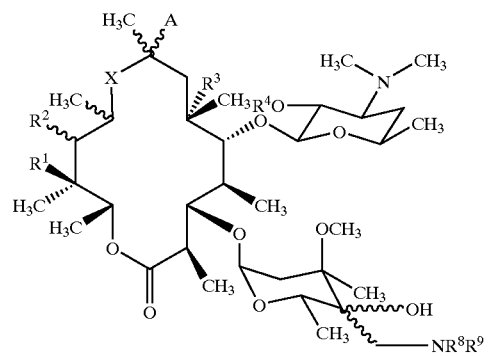

54

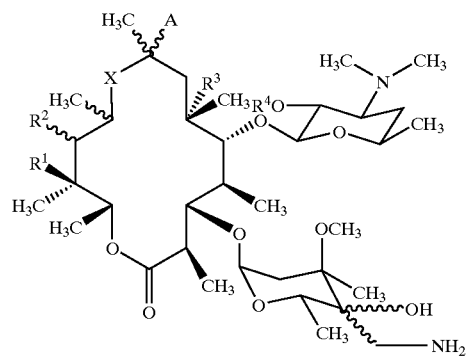

53

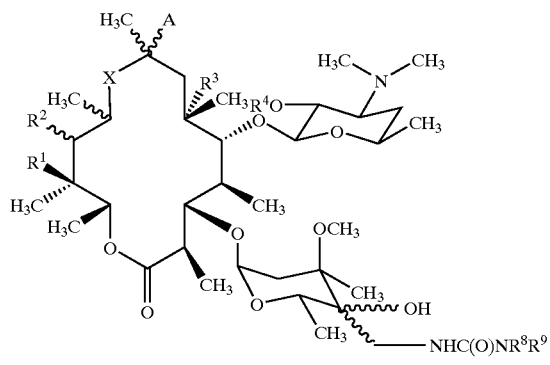

55

Scheme 14

Scheme 14 describes another synthesis of compounds of formula 1 wherein Y is CH(4"-substituted cladinose) as shown in formulas 57 and 58. Starting compounds of formula 50 are available from Scheme 13. Compounds of formula 50 can be converted to those of formula 56 by an epoxide-opening reaction with $NH_2(CH_2)_nNH_2$, wherein n is an integer ranging from 0 to 10. Reductive alkylation or direct alkylation of compounds of formula 56 can provide those of formula 57 by using methods well known to those skilled in the art. Compounds of formula 50 can be converted to those of formula 58 via an epoxide-opening reaction with $NH_2(CH_2)_nC(O)NR^8R^9$ by using methods well known to those skilled in the art.

SCHEME 14

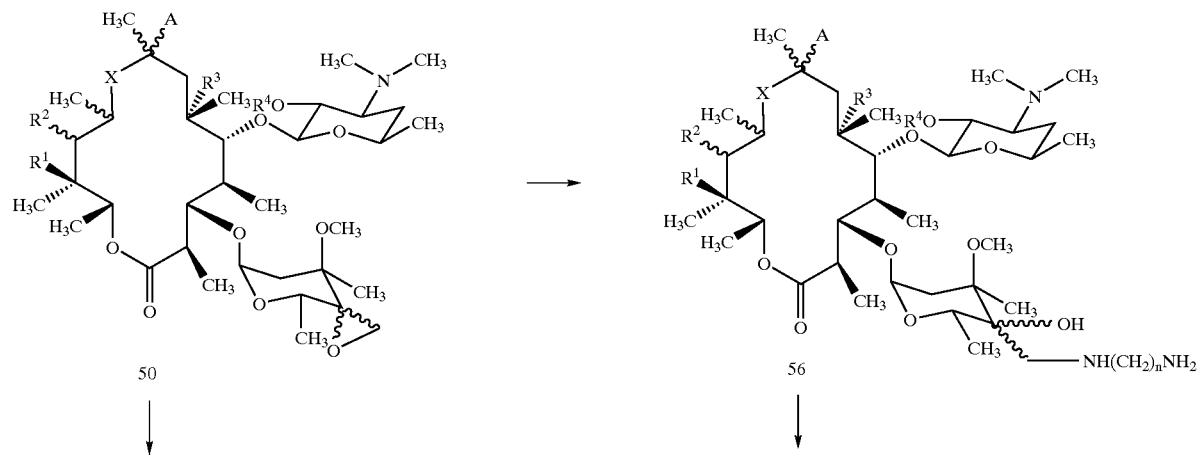

50

56

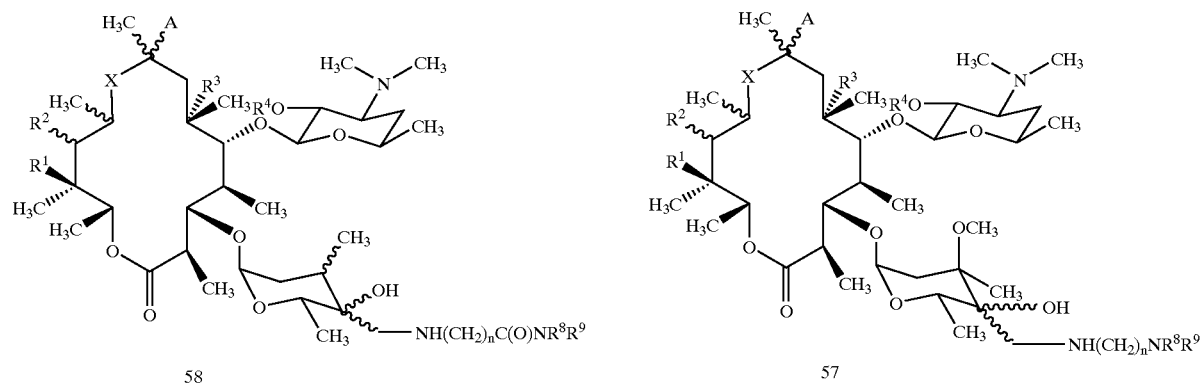

58

57

Scheme 15

Scheme 15 outlines the synthesis of compounds of formula 1, wherein $R^1$ and $R^2$ together form a cyclic carbamate or carbazate as shown in formula 65, and the synthesis of compounds of formula 1A, wherein $R^f$ is H or a —C(O)—imidazolyl and $R^3$ is $OR^{10}$ as shown in formulas 62 and 63, respectively. Starting compounds of formula 37 can be made from 13-methyl erythromycin A according to Scheme 8. The transformation of compounds of formula 37 to those of formula 64 can be achieved by following substantially the same procedures as those described in WO 99/35157. The 2' hydroxyl and 4" hydroxyl of compounds of formula 37 can be protected by using the methods summarized in Greene and Wuts, pp. 10–142, to provide compounds of formula 59, wherein $P^1$ and $P^2$ represent the same or different protecting groups. The preferred protecting groups are silyl ethers, such as trimethylsilyl ether, or esters, such as acetate or benzoate. The 11,12-cyclic carbonation of compounds of formula 59 can be accomplished to provide compounds of formula 60 by using a variety of methods, including DBU and carbonyidiimidazole or trichloroacetyl isocyanate. Compounds of formula 60 can be converted to those of formula 61 by a variety of synthetic routes using conventional methods known to those skilled in the art. Compounds of formula 61 can undergo beta-elimination in the presence of a base such as DBU or triethylamine. Reaction of compounds of formula 62 with carbonyldiimidazole and a base such as DBU or metal hydride can provide compounds of formula 63. Compounds of formula 61 can be converted directly to compounds of formula 63 by treatment with a base and carbonyidiimidazole. Addition of compounds of formula 63 with $R^6B^1NH_2$, wherein $R^6$ and $B^1$ are as defined previously, by following substantially the same procedures as those reported in Agouridas et al., J. Med. Chem., vol. 41, pp. 40804100 (1998) (hereinafter "Agouridas"); W. W. Baker et al., J. Org. Chem., pp. 2340–2345 (1988); or G. Griesgraber et al., J. Antibiotics, vol. 49, pp. 465–77 (1996), can afford compounds of formula 64. The protecting group of the 2' hydroxyl of compounds of formula 64 can be removed by using conventional methods known to those skilled in the art. Further conventional chemical manipulation of the 2' hydroxyl of compounds of formula 64 can furnish compounds of formula 65.

SCHEME 15
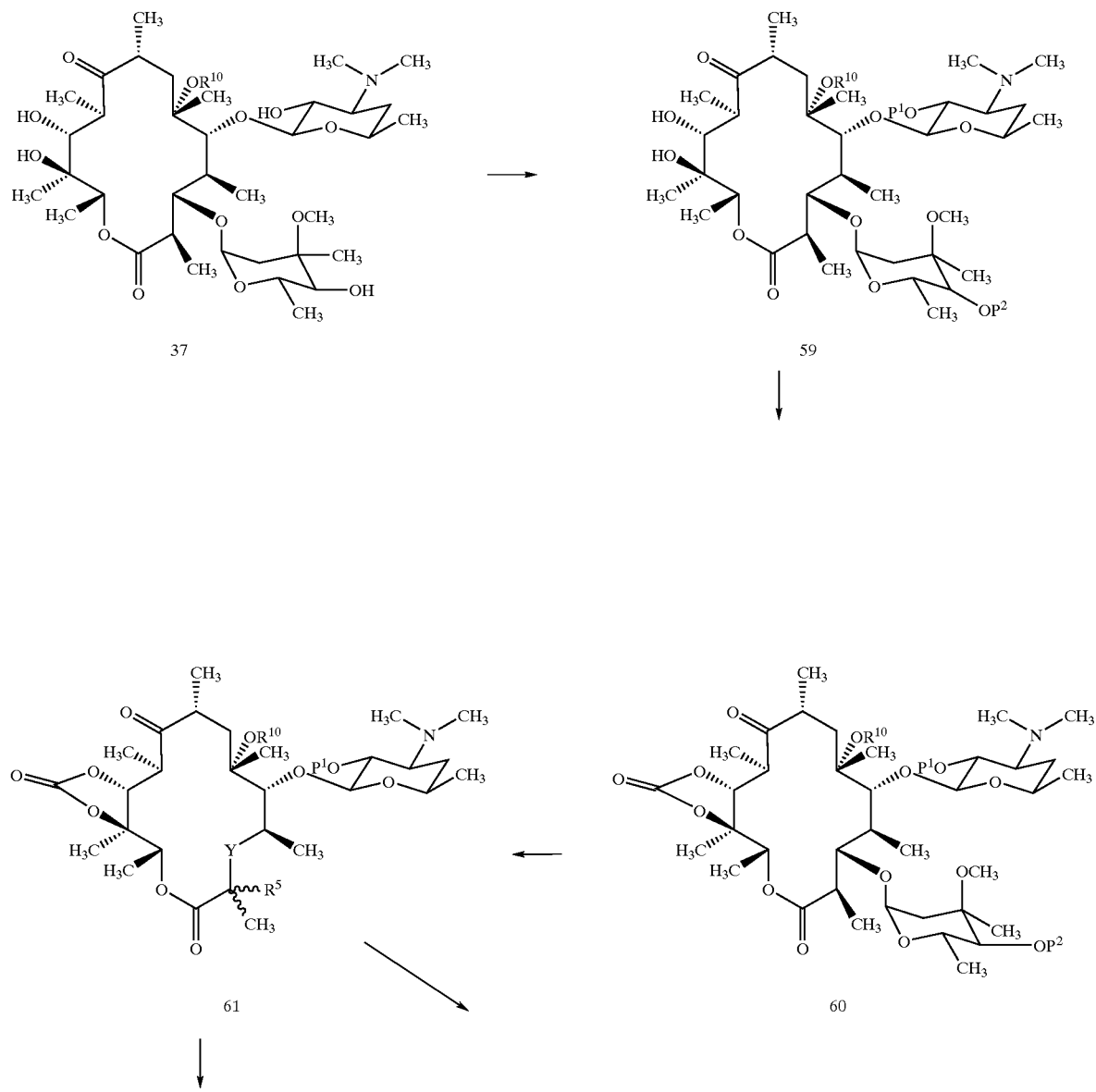

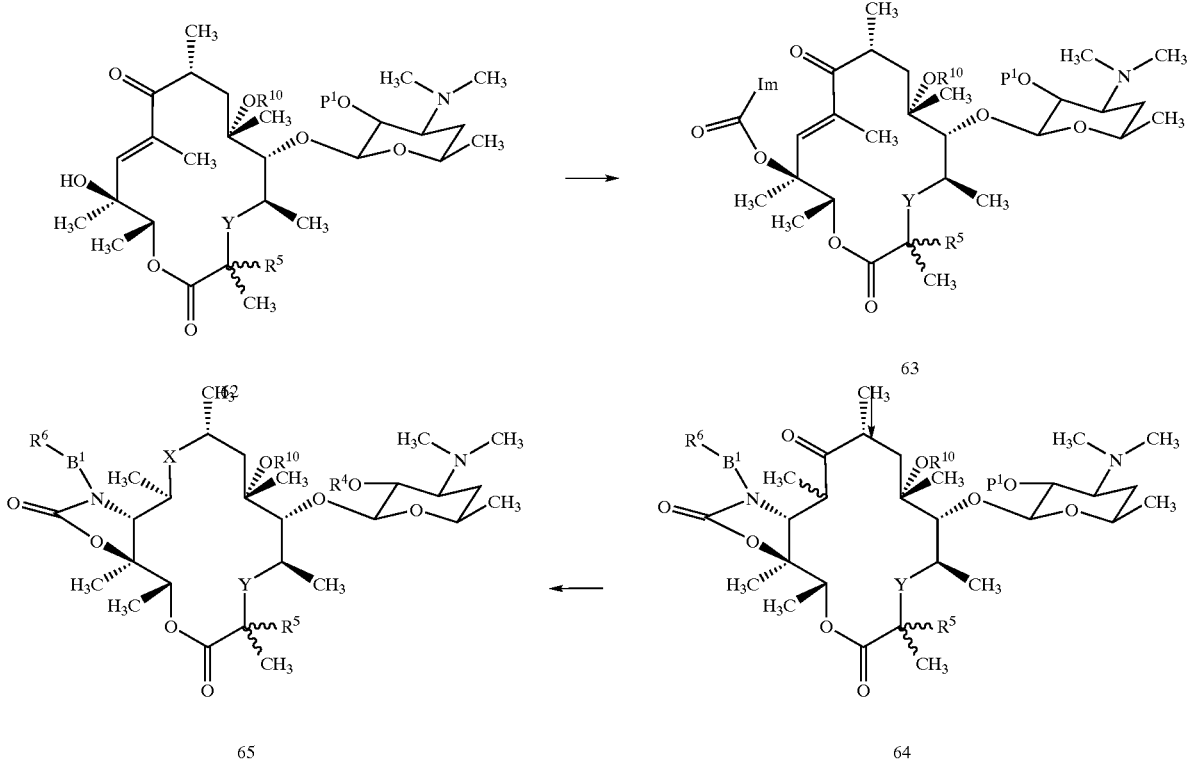

Scheme 16

Scheme 16 outlines the synthesis of compounds of formula 1 wherein $R^1$ and $R^2$ together with X form two additional rings as shown in formula 66. Starting compounds of formula 63 are available from Scheme 15. Reaction of compounds of formula 63 with $NH_2C(D)(E)C(F)(G)NH_2$, wherein D, E, F and G are as defined previously, followed by deprotection of $P^1$ at 2' and subsequent conventional chemical manipulation of the 2' hydroxyl can provide compounds of formula 66.

SCHEME 16

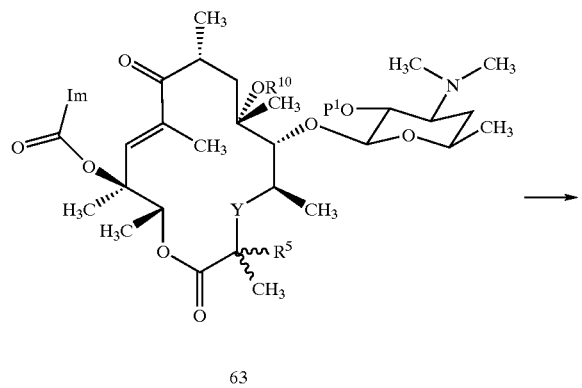

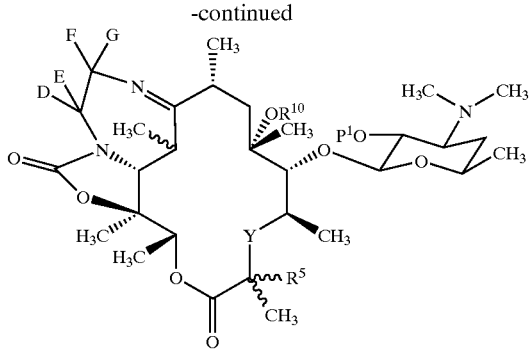

Scheme 17

Scheme 17 outlines the synthesis of compounds of formula 1 wherein $R^1$ and $R^2$ together with X form two additional rings as shown in formula 72. Starting compounds of formula 67 can be prepared according to Scheme 15. Oximation of compounds of formula 68 can be carried out by using conventional methods well known to those skilled in the art. The conversion of compounds of formula 68 wherein $R^8$ is hydrogen to those of formula 69 can be achieved by using a reducing agent such as $TiCl_3$, followed by $NaBH_3CN$ or by catalytic hydrogenation. Reaction of compounds of formula 69 with C(D)(E)(O), wherein D and E are as defined previously, in the presence of a acid such as formic acid or acetic acid can generate compounds of formula 70, which can undergo reductive alkylation or direct alkylation to provide compounds of formula 71. Treatment of compounds of formula 71 with a base followed by a halogenating agent or an appropriate electrophile using the procedures described in WO 99/21865, published May 6, 1999, can generate compounds of formula 72. Examples of suitable bases include sodium hydride, potassium hydride, DBU, lithium or sodium or potassium diisopropylamide, or potassium or sodium hydroxide. Examples of a suitable halogenating agent include 1-(chloromethyl)4-fluoro-1,4-diazonibicyclo(2.2.2)octane bis(tetrafluoroborate) and $(ArSO_2)_2N$-halogen, wherein Ar is a $C_6$–$C_{10}$ aryl.

compounds of formula 73 can be prepared according to Scheme 17. Treatment of compounds of formula 73 with tosyl chloride or mesyl chloride and a base such as triethylamine, pyridine or DBU can provide compounds of formula 74. Treatment of compounds of formula 74 with a base followed by a halogenating agent or an appropriate electrophile can generate compounds of formula 75. Examples of suitable bases include sodium hydride, potassium hydride, DBU, lithium or sodium or potassium

SCHEME 17

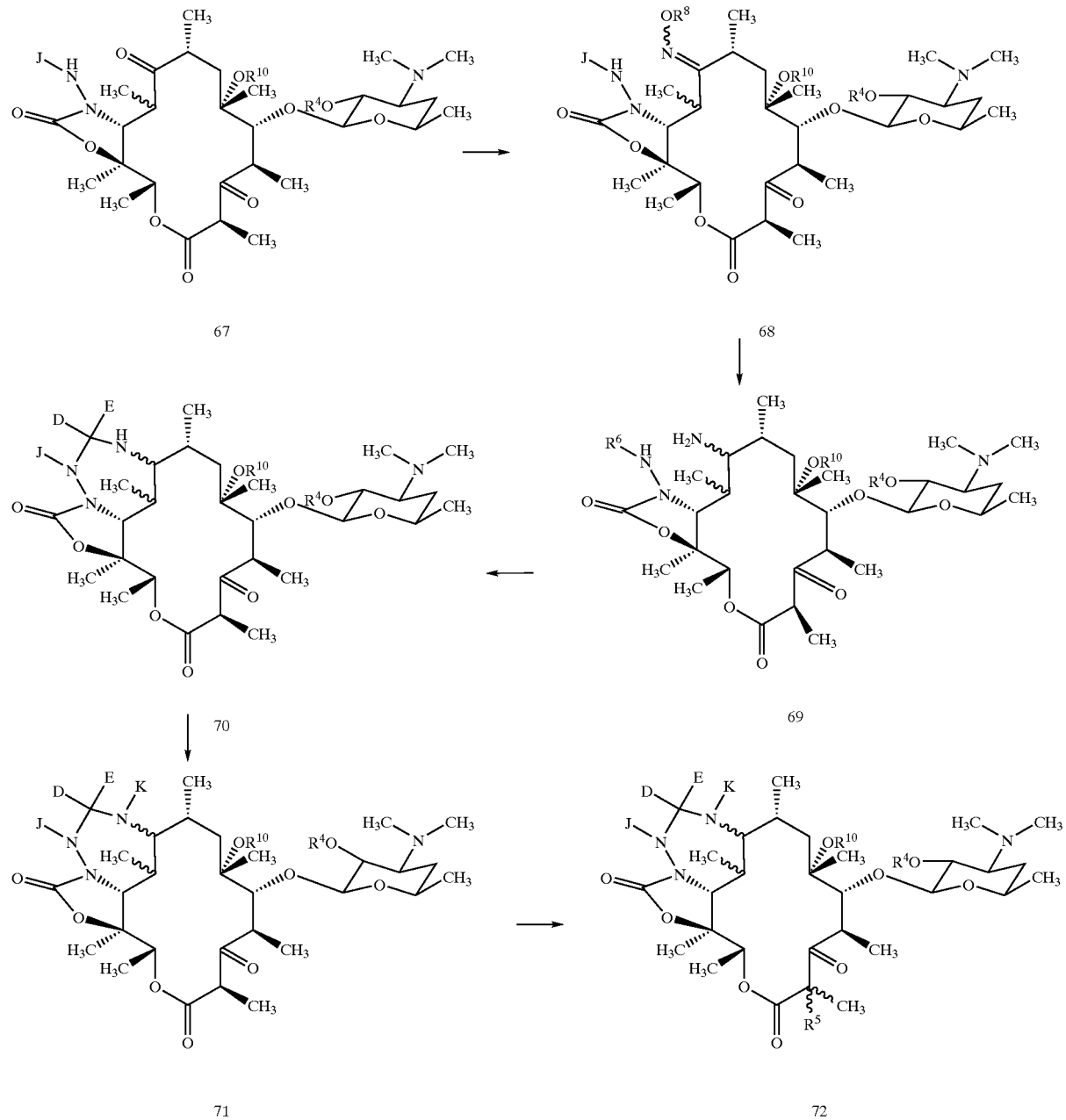

Scheme 18

Scheme 18 outlines the synthesis of compounds of formula 1 wherein $R^1$ and $R^2$ together with X form two additional rings as shown in formulas 75, 77 and 78. Starting diisopropylamide, or potassium or sodium hydroxide. Examples of a suitable halogenating agent include 1-(chloromethyl)4-fluoro-1,4-diazonibicyclo(2.2.2)octane bis(tetrafluoroborate) and $(ArSO_2)_2N$-halogen, wherein Ar is a $C_6$–$C_{10}$ aryl. Reaction of compounds of formula 73 with C(D)(E)(O), wherein D and E are as defined previously, in the presence of an acid such formic acid or acetic acid can provide compounds of formula 76. Compounds of formula 76 can be converted to those of formula 77 in a fashion similar to the conversion of compounds of formula 74 to those of formula 75. Reduction of compounds of formula 77 to those of formula 78 can be carried out by using a reducing agent, for example, triphenylphosphine, or by catalytic hydrogenation by following substantially the same procedures as those described in WO 99/21865.

Scheme 19

Scheme 19 outlines the synthesis of compounds of formula 1 wherein $R^1$ and $R^2$ together form a cyclic urea as shown in formula 86. Starting compounds of formula 60 can be made from 13-methyl erythromycin A according to Scheme 15. The cladinose moiety of compounds of formula 60 can be removed to provide compounds of formula 79 by treatment with an acid such as hydrochloric acid or sulfuric acid. Oxidation of compounds of formula 79 can be accomplished to provide compounds of formula 80 by using a variety of conventional methods well known to those skilled in the art, such as the modified Pfitzner-Moffat procedure as

SCHEME 18

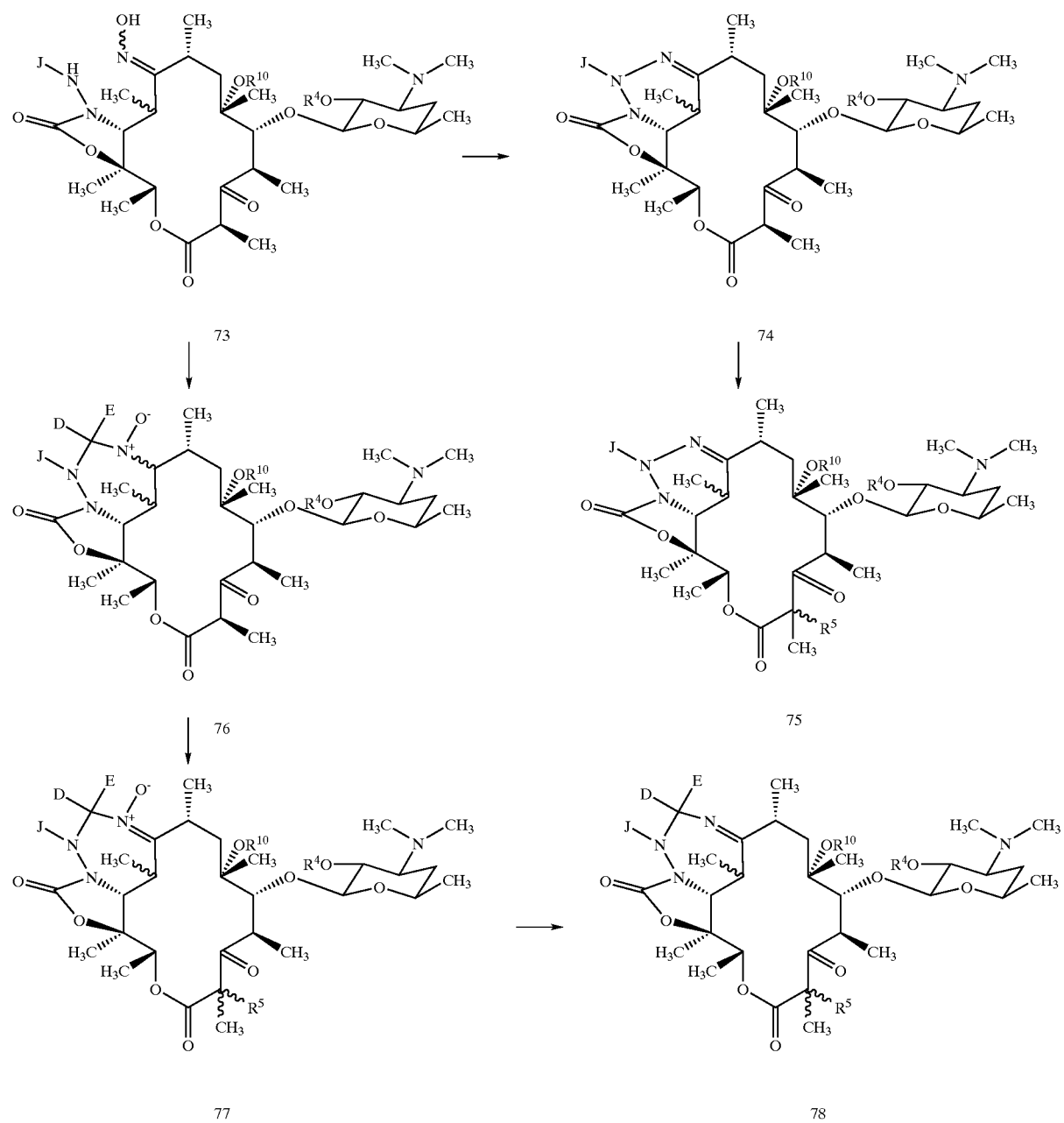

described in *Agouridas*, pp. 4080–4100. Reaction of compounds of formula 80 with a base such as triethylamine or DBU can promote beta-elimination to generate the alcohols of formula 81. Compounds of formula 81 can be converted to those of formula 82 by treatment with carbonyldiimidazole and a base such as triethylamine or DBU. Compounds of formula 80 can be converted directly to those of formula 82 by reacting the compounds of formula 80 with carbonyidiimidazole and a base, such as DBU and triethylamine. The acetal opening reaction can be carried out to provide the azides of formula 83 by treating compounds of formula 82 with an azide reagent, such as TMS-N3 in the presence of a Lewis acid, such as $Me_3Al$ or $Me_2AlCl$. The conversion of compounds of formula 83 to those of formula 84 can be achieved by reduction with a reducing agent such as triphenylphosphine or by catalytic hydrogenation. Reaction of compounds of formula 84 with a base, such as metal hydride or DBU, and carbonyidiimidazole followed by $R^6B^1NH_2$, wherein $R^6$ and $B^1$ are as defined previously, can afford the 11,12-cyclic ureas of formula 85. The 2' protecting group can be removed by using the methods summarized in *Greene and Wuts*, pp. 10–142. Subsequent conventional chemical manipulation of the 2' hydroxyl group can provide compounds of formula 86.

SCHEME 19

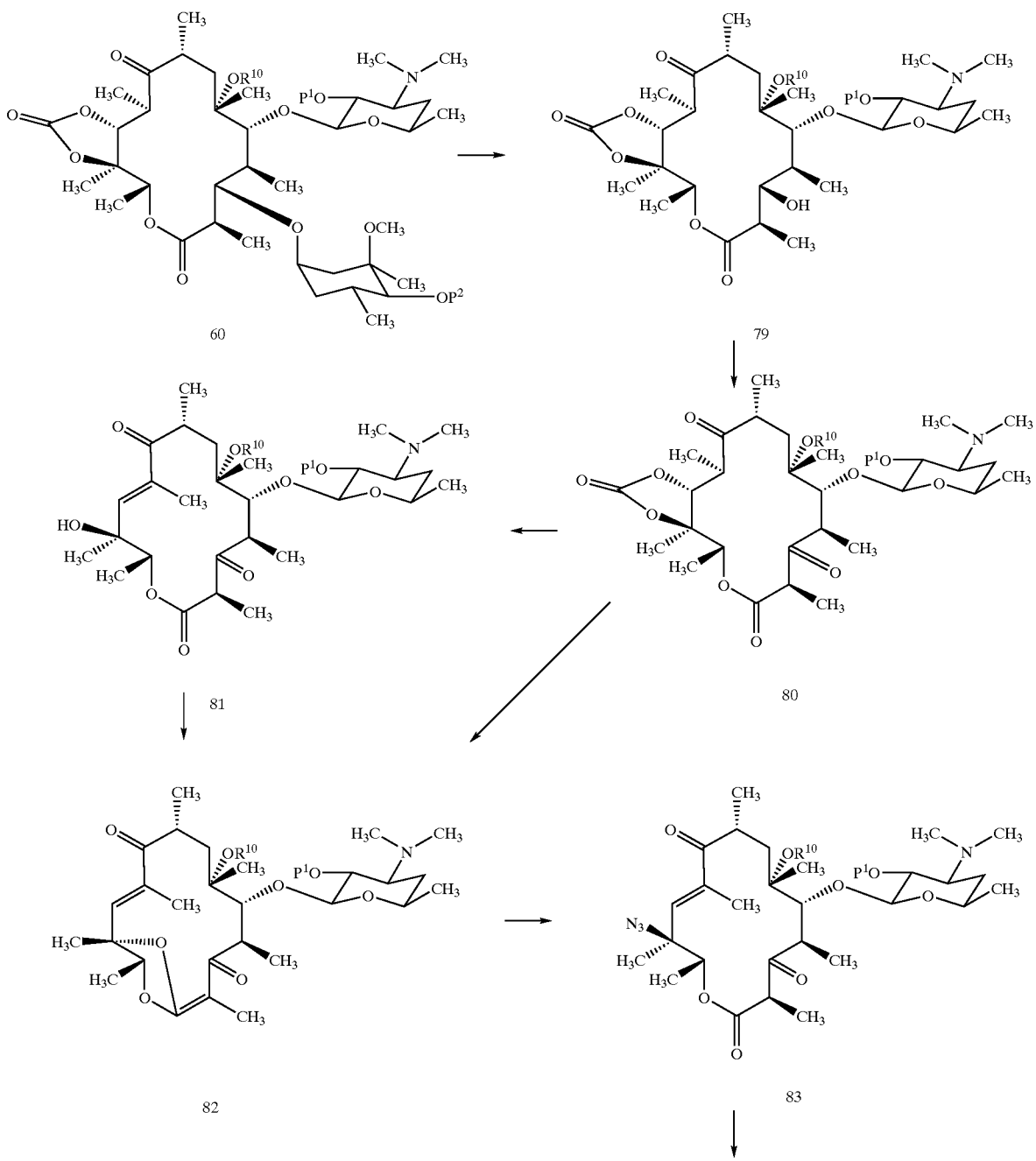

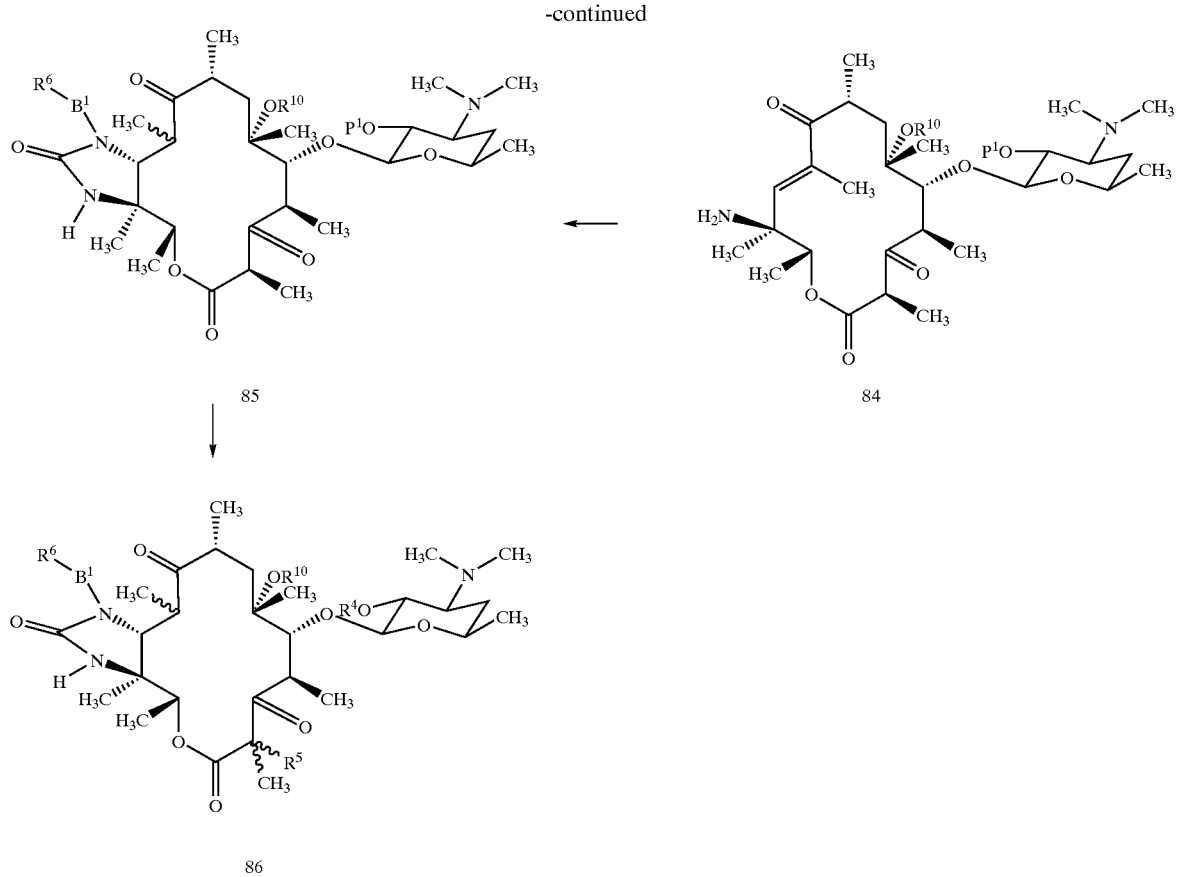

Scheme 20

Scheme 20 outlines the synthesis of compounds of formula 1 wherein $R^3$ and Y together form a cyclic ketal as shown in formula 88. Starting compounds of formula 38 can be made from 13-methyl erythromycin A by using methods well known to those skilled in the art. The cladinose moiety of compounds of formula 38 can be removed to provide compounds of formula 87 by treatment with an acid, such hydrochloric acid or sulfuric acid. The ketals of formula 88 can be formed from the compounds of formula 87 by reaction with $R^{14}R^{15}C(O)$, wherein $R^{14}$ and $R^{15}$ are as defined previously, in the presence of an acid. The preferred acid is p-toluenesulfonic acid.

SCHEME 20

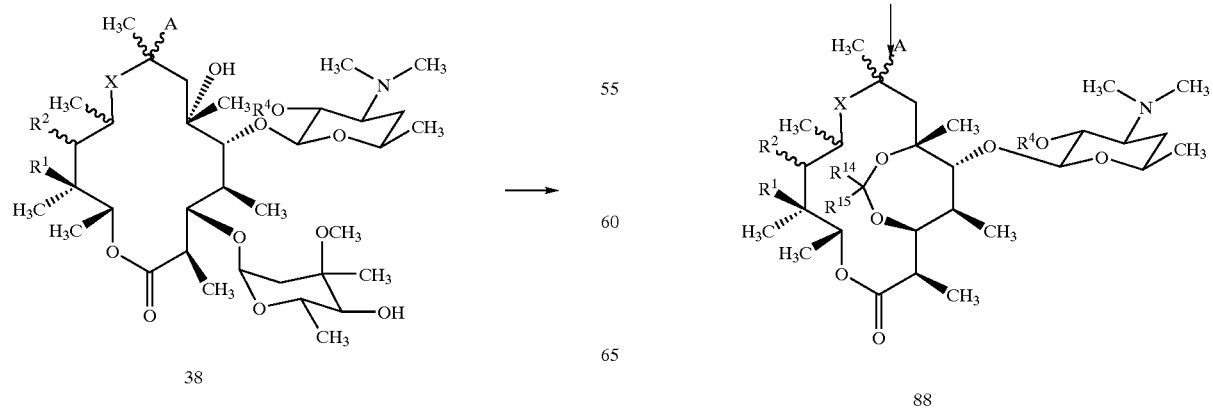

The compounds of the present invention may have asymmetric carbon atoms. Such diastereomeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomeric mixture by reaction with an appropriate optically active compound (e.g., alcohol), separating the diastereomers and converting (e.g., hydrolyzing) the individual diastereomers to the corresponding pure enantiomers. All such isomers, including the enantiomer mixtures, the diastereomer mixtures, the pure diastereomers and the pure enantiomers, are considered to be part of the invention.

The compounds of formulas 1 and 1A that are basic in nature are capable of forming a wide variety of salts with various inorganic and organic acids. Although such salts must be pharmaceutically acceptable for administration to animals (including mammals, fish and birds), it is often desirable in practice to initially isolate a compound of formula 1 or 1A from the reaction mixture as a pharmaceutically unacceptable salt, to then simply convert the latter back to the free base compound by treatment with an alkaline reagent, and to subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of formulas 1 and 1A that are acidic in nature are capable of forming base salts with various pharmacologically acceptable cations. Examples of such salts include the alkali metal or alkaline earth metal salts and, particularly, the sodium and potassium salts. These salts may be prepared by conventional techniques. The chemical bases that are used as reagents to prepare the pharmaceutically acceptable base salts of this invention are those that form non-toxic base salts with the acidic compounds of formulas 1 and 1A. Such non-toxic base salts include those derived from such pharmacologically acceptable cations as sodium, potassium, calcium and magnesium, etc. These salts can be prepared by treating the corresponding acidic compounds with an aqueous solution containing the desired pharmacologically acceptable cations and then evaporating the resulting solution to dryness, preferably under reduced pressure. Alternatively, they may also be prepared by mixing lower alkanolic solutions of the acidic compounds and the desired alkali metal alkoxide together and then evaporating the resulting solution to dryness in the same manner as before. In either case, stoichiometric quantities of reagents are preferably employed in order to ensure completeness of the reaction and maximum yields of the desired final product.

The compounds of formulas 1 and 1A and their pharmaceutically acceptable salts, prodrugs and solvates (hereinafter referred to collectively as "the active compounds of this invention") may be administered alone or in combination with pharmaceutically acceptable carriers, in either single or multiple doses. A pharmaceutically acceptable carrier will generally be selected with regard to the intended route of administration and standard pharmaceutical practice.

Pharmaceutical compositions of this invention comprise any of the compounds of the present invention, and pharmaceutically acceptable salts, prodrugs and solvates thereof, together with any pharmaceutically acceptable carrier. Suitable pharmaceutical carriers include, but are not limited to, inert solid diluents or fillers, sterile aqueous solutions and various organic solvents. Examples of suitable pharmaceutically acceptable carriers include ion exchangers, alumina, aluminum stearate, lecithin, self-emulsifying drug delivery systems (SEDDS), surfactants used in pharmaceutical dosage forms such as Tweens or other similar polymeric delivery matrices, serum proteins, such as human serum albumin, polyethylene glycol polymers such as PEG400, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, sodium carboxymethylcellulose, polyacrylates, waxes, polyethylene-polyoxypropylene-block polymers and wool fat.

The pharmaceutical compositions formed using the active compounds of this invention may be administered orally, parenterally, by inhalation spray, topically, rectally, nasally, buccally, vaginally or via an implanted reservoir. The pharmaceutical compositions of this invention may contain any conventional non-toxic pharmaceutically acceptable carriers. In some cases, the pH of the formulation may be adjusted with pharmaceutically acceptable acids, bases or buffers to enhance the stability of the formulated compound or its delivery form. The term "parenteral" as used herein includes subcutaneous, intracutaneous, intravenous, intramuscular, intra-articular, intraperitoneal, intrasynovial, intrasternal, intrathecal, intralesional and intracranial injection or infusion techniques.

For parenteral administration, the pharmaceutical compositions of this invention may be in the form of solutions containing sesame or peanut oil, aqueous propylene glycol or sterile aqueous solution. Aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

The pharmaceutical compositions of this invention may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed, including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as carboxymethyl cellulose or similar dispersing agents that are commonly used in the formulation of pharmaceutically acceptable dosage forms such as emulsions and/or suspensions. Other commonly used surfactants such as Tweens and Spans and/or other similar emulsifying agents or bioavailability enhancers that are commonly used in the manufacture of pharmaceutically acceptable solid, liquid or other dosage forms may also be used for the purposes of formulation.

The pharmaceutical compositions of this invention may be orally administered in any orally acceptable dosage form including, but not limited to, hard or soft gelatin capsules, tablets, powders, lozenges, emulsions and aqueous suspensions, dispersions and solutions. In the case of tablets for oral use, carriers that are commonly used include lactose and corn starch. Various excipients such as sodium citrate, calcium carbonate and calcium phosphate may be employed along with disintegrants such as starch, methylcellulose, alginic acid and certain complex silicates, together with binding agents such as polyvinylpyrrolidone, sucrose, gelatin and acacia. Lubricating agents, such as magnesium stearate, sodium lauryl sulfate and talc, are also typically added. Solid compositions of a similar type may also be employed as fillers for oral administration in the form of soft and hard filled gelatin capsules. Preferred diluents for oral administration in a capsule form include lactose or milk sugar and high molecular weight polyethylene glycols. When aqueous suspensions and/or emulsions are administered orally, the active ingredient is combined with emulsifying and/or suspending agents and/or diluents such as water, ethanol, propylene glycol, glycerin and combinations thereof. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient that is solid at room temperature but liquid at the rectal temperature. The excipient will therefore melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyidodecanol, benzyl alcohol and water. The pharmaceutical compositions of this invention may also be topically applied to the lower intestinal tract by rectal suppository formulation or in a suitable enema formulation. Topically transdermal patches are also included in this invention.

The pharmaceutical compositions of this invention may be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

To implement the methods of this invention, an effective dose of an active compound of this invention is administered to a susceptible or infected animal (including mammals, fish and birds) by parenteral, oral, nasal, buccal, vaginal or rectal routes, or locally as a topical application to the skin and/or mucous membranes. The route of administration will depend on the mammal, fish or bird that is being treated.

The daily dose will usually range from about 0.25 to about 150 mg/kg body weight of the patient to be treated, preferably from about 0.25 to about 25 mg/kg. Typically, the compounds and compositions of this invention will be administered from about__to about__times per day or, alternatively, as a continuous infusion. Such administration can be used as a chronic or acute therapy. The amount of active ingredient that may be combined with the carrier materials to produce a single dosage form will vary depending upon the host treated and the particular mode of administration.

As the skilled artisan will appreciate, lower or higher doses than those recited above may be required. Specific dosage and treatment regimens for any particular patient will depend upon a variety of factors, including the severity of the disease, the activity of the specific compound employed, the age, body weight, general health status, sex and diet of the patient, the time of administration, the rate of excretion of the drug, whether a drug combination is employed, the severity and course of the disorder, the patientp's disposition to the disorder and the judgment of the treating physician.

The compounds of this invention may be administered to a patient either as a single agent or in combination with other agents. The compounds of this invention may be co-administered with other compounds of this invention or with other antibacterial or antiprotozoal agents to increase the effect of therapy. Combination therapies according to this invention may exert an additive or synergistic antibacterial or antiprotozoal effect, e.g., because each component agent of the combination may act on a different site or through a different mechanism. The use of such combination therapies may also advantageously reduce the dosage of a given conventional antibiotic agent that would be required for a desired therapeutic effect, as compared to when that agent is administered as a monotherapy. Such combinations may reduce or eliminate the side effects of conventional antibiotic therapies, while not interfering with the antibiotic activity of those agents. These combinations reduce the potential of resistance to single agent therapies, while minimizing any associated toxicity. Alternatively, pharmaceutical compositions according to this invention may be comprised of a combination of a compound of this invention and another agent having a different therapeutic or prophylactic effect.

When the compounds of this invention are administered in combination therapies with other agents, they may be administered sequentially or concurrently to the patient. The additional agents may be administered separately, as part of a multiple dose regimen, from the compounds of this invention. Alternatively, those agents may be part of a single dosage form, mixed together with the compounds of this invention in a single composition. The pharmaceutical compositions according to this invention may comprise a combination of an antibacterial or antiprotozoal agent according to this invention and one or more therapeutic agents.

The activity of each of the compounds of the present invention may be tested in various ways. For example, the activity of each of the compounds of the present invention against bacterial and protozoal pathogens is demonstrated by each compound's ability to inhibit the growth of defined strains of human (Assay I) or animal (Assays II and ll) pathogens.

Assay I

Assay I, described below, employs conventional methodology and interpretation criteria. This assay is designed to identify chemical modifications that may lead to compounds that circumvent defined macrolide resistance mechanisms. Assay I employs a panel of bacterial strains that includes a variety of target pathogenic species, including representatives of previously characterized macrolide resistance mechanisms. Use of this panel demonstrates the relationship between the chemical structure of a compound and its activity with respect to potency, spectrum of activity, and structural elements or modifications that may be necessary to obviate resistance mechanisms. The bacterial pathogens that are included in the screening panel are shown in the table below. In many cases, both the macrolide-susceptible parent strain and the macrolide-resistant strain derived from it are available to provide a more accurate assessment of the compound's ability to circumvent the resistance mechanism.

Strains that contain the gene with the designation of ermAlermB/ermC are resistant to macrolides, lincosamides and streptogramin B antibiotics. This resistance is due to modification (methylation) of 23S rRNA molecules by an Erm methylase, which generally prevents the binding of all three structural classes. Two types of macrolide efflux have been described; msrA encodes a component of an efflux system in staphylococci that prevents the entry of macrolides and streptogramins, while mefA/E encodes a transmembrane protein that appears to efflux only macrolides. Inactivation of macrolide antibiotics can occur and can be mediated either by a phosphorylation of the 2'-hydroxyl (mph) or by cleavage of the macrocyclic lactone (esterase). The strains may be characterized using conventional polymerase chain reaction (PCR) technology and/or by sequencing the resistance determinant. The use of PCR technology in this application is described in J. Sutcliffe et al., "Detection of Erythromycin-Resistant Determinants by PCR", *Antimicrobial Agents and Chemotheraphy*, vol. 40, no. 11, pp. 2562–2566 (1996).

The test compounds are initially dissolved in dimethylsulfoxide (DMSO) as 40 mg/ml stock solutions. The antibacterial assay is performed in microtiter trays and interpreted according to *Performance Standards for Antimicrobial Disk Susceptibility Tests—Sixth Edition: Approved Standard*, published by The National Committee for Clinical Laboratory Standards (NCCLS) guidelines; the minimum inhibitory concentration (MIC) is used to compare the strains. The terms "acr AB" and "acr AB-like" indicate that an intrinsia multidrug efflux pump exists in the strain.

| Starin Designation | Macrolide Resistance Mechanism(s) |
| --- | --- |
| *Staphylococcus aureus* 1116 | susceptible parent |
| *Staphylococcus aureus* 1117 | ErmB |
| *Staphylococcus aureus* 0052 | susceptible parent |
| *Staphylococcus aureus* 1120 | ErmC |
| *Staphylococcus aureus* 1032 | msrA, mph, esterase |
| *Staphylococcus hemolyticus* 1006 | msrA, mph |
| *Staphylococcus pyogenes* 203 | susceptible parent |
| *Staphylococcus pyogenes* 1079 | ErmB |
| *Staphylococcus pyogenes* 1062 | susceptible parent |
| *Streptococcus pyogenes* 1061 | ErmB |
| *Streptococcus pyogenes* 1064 | MefA |
| *Streptococcus agalactiae* 1024 | susceptible parent |
| *Streptococcus agalactiae* 1023 | ErmB |
| *Streptococcus pneumoniae* 1016 | susceptible |
| *Streptococcus pneumoniae* 1046 | ErmB |
| *Streptococcus pneumoniae* 1095 | ErmB |
| *Streptococcus pneumoniae* 1175 | MefE |
| *Haemophilus pneumoniae* 0085 | susceptible; acr AB-like |
| *Haemophilus pneumoniae* 0131 | susceptible; acr AB-like |
| *Moraxella catarrhalis* 0040 | susceptible |
| *Moraxella catarrhalis* 1055 | erythromycin intermediate resistance |
| *Escherichia coli* 0266 | susceptible; acr AB |
| *Haemophilus influenzae* 1100 | susceptible; acr AB-like |

Assay II is used to test for activity against *Pasteurella multocida*.

Assay II

This assay is based on the liquid dilution method in microliter format. A single colony of *P. multocida* (strain 59A067) is inoculated into 5 ml of brain heart infusion (BHI) broth. The test compounds are prepared by solubilizing 1 mg of the compound in 125 μl of dimethylsulfoxide (DMSO). Dilutions of the test compound are prepared using uninoculated BHI broth. The concentrations of the test compound used range from 200 μg/ml to 0.098 μg/ml by two-fold serial dilutions. The *P. multocida*-inoculated BHI is diluted with uninoculated BHI broth to make a $10^4$ cell suspension per 200 μl. The BHI cell suspensions are mixed with respective serial dilutions of the test compound and incubated at 37° C. for 18 hours.

The minimum inhibitory concentration (MIC) is equal to the concentration of the compound exhibiting 100% inhibition of growth of *P. multocida* as determined by comparison with an uninoculated control.

Assay III is used to test for activity against *Pasteurella haemolytica*.

Assay III

This assay is based on the agar dilution method using a Steers Replicator. Two to five colonies isolated from an agar plate are inoculated into BHI broth and incubated overnight at 37° C. with shaking (200 rpm). The next morning, 300 µl of the fully grown *P. haemolytica* preculture is inoculated into 3 ml of fresh BHI broth and is incubated at 37° C. with shaking (200 rpm). The appropriate amounts of the test compounds are dissolved in ethanol and a series of two-fold serial dilutions are prepared. Two ml of the respective serial dilution is mixed with 18 ml of molten BHI agar and solidified. When the inoculated *P. haemolytica* culture reaches 0.5 McFarland standard density, about 5 µl of the *P. haemolytica* culture is inoculated onto BHI agar plates containing the various concentrations of the test compound using a Steers Replicator and incubated for 18 hours at 37° C. Initial concentrations of the test compound range from 100–200 µg/ml.

The MIC is equal to the concentration of the test compound exhibiting 100% inhibition of growth of *P. haemolytica* as determined by comparison with an uninoculated control.

The in vivo activity of the compounds of the present invention can be determined by conventional animal protection studies well known to those skilled in the art, usually carried out in mice. Assay IV is an example of an animal protection study performed in mice and used to test for activity against *P. multocida*.

Assay IV

Mice are allotted to cages (10 per cage) upon their arrival, and allowed to acclimate for a minimum of 48 hours before being used. Animals are inoculated with 0.5 ml of a 3×10³ CFU/ml bacterial suspension (*P. multocida* strain 59A006) intraperitoneally. Each experiment has at least 3 non-medicated control groups, including one infected with a 0.1×challenge dose and two infected with a 1×challenge dose; a 1×challenge data group may also be used. Generally, all mice in a given study can be challenged within 30–90 minutes, especially if a repeating syringe (such as a Cornwall® syringe) is used to administer the challenge. Thirty minutes after challenging has begun, the first compound treatment is given. It may be necessary for a second person to begin compound dosing if all of the animals have not been challenged at the end of 30 minutes. The routes of administration are subcutaneous or oral. Subcutaneous doses are administered into the loose skin in the back of the neck, whereas oral doses are given by means of a feeding needle. In both cases, a volume of 0.2 ml is used per mouse.

The test compounds are administered 30 minutes, 4 hours and 24 hours after challenge. A control compound of known efficacy administered by the same route is included in each test. The animals are observed daily, and the number of survivors in each group is recorded. The *P. multocida* model monitoring continues for 96 hours (four days) post challenge.

The $PD_{50}$ is a calculated dose at which the test compound protects 50% of a group of mice from mortality due to a bacterial infection that would be lethal in the absence of drug treatment.

EXAMPLE 1

Compound of Formula 14

200 mg of 13-methyl erythromycin A is dissolved in 10 mL of anhydrous pyridine. Hydroxylamine hydrochloride (0.145 g, 7.5 equiv.) is added, and the solution is heated to 60° C. and stirred for 24 hours. The reaction is worked up by decanting into 25 mL of a 1:1 mixture of methylene chloride and water. The pH is adjusted to 10 using 1N NaOH, extracted with 3×25 mL methylene chloride, and dried over $Na_2SO_4$. Filtration and concentration of filtrate yields a light yellow solid product. The product (0.195 g) is purified by HPLC to yield the title compound as a white solid (0.085 g).

MS: m/z 735 (M+H).

EXAMPLE 2

Compound of Formula 15

70 mg of the compound of formula 14, obtained from Example 1, is dissolved in 1.5 mL of acetone. An aqueous solution of $Na_2HCO_3$ (1.0 9 in 10.0 mL water) is added (0.33 mL) and the resulting mixture is cooled to 0° C. A solution of para-toluenesulfonyl chloride (0.380 g) in acetone (1.0 mL), cooled to 0° C., is added (0.1 mL) and the mixture stirred overnight. The reaction is worked up by decanting into 30 mL of a 1:1 mixture of methylene chloride and water. The pH is adjusted to 10 using 1N NaOH, extracted with 3×20 mL methylene chloride, and dried over $Na_2SO_4$. Filtration and concentration of filtrate yields the title compound as a solid (0.062 g).

MS: m/z 717 (M+H).

EXAMPLE 3

Compound of Formula 16

60 mg of the compound of formula 15, obtained from Example 2, is dissolved in 0.50 mL tetrahydrofuran and 2.5 mL ethylene glycol and then cooled to 0–5° C. $NaBH_4$ (0.047 g) is added and the reaction stirred for 10 hours at 0–5° C. The reaction is worked up by decanting into 20 mL of a 1:1 mixture of methylene chloride and water. The aqueous is re-extracted with 1×10 mL methylene chloride. The organic layers are combined and dried over $Na_2SO_4$. Filtration and concentration yields the title compound as a solid (0.037 g).

MS: m/z 721 (M+H).

Compound 16

| Carbon # | $^{13}$C - ppm | $^1$H - ppm |
|---|---|---|
| 1 | 178.13 | — |
| 2 | 45.24 | 2.72 |
| 3 | 78.06 | 4.31 |
| 4 | 43.18 | 2.06 |
| 5 | 83.33 | 3.70 |
| 6 | 74.42 | — |
| 7 | 43.15 | 1.78 |
|   |       | 1.44 |
| 8 | 30.52 | 1.82 |
| 9 | 57.93 | 3.10 |
|   |       | 1.97 |
| 10 | 57.17 | 2.71 |
| 11 | 72.68 | 3.74 |
| 12 | 74.33 | — |
| 13 | 73.52 | 4.87 |
| 14 | 13.58 | 1.28 (3) |
| 15 | 14.24 | 1.21 (3) |
| 16 | 9.69 | 1.10 (3) |
| 17 | 28.04 | 1.34 (3) |
| 18 | 22.52 | 1.00 (3) |
| 19 | 14.78 | 1.22 (3) |
| 20 | 16.36 | 1.14 (3) |
| 1' | 103.28 | 4.48 |
| 2' | 71.28 | 3.26 |
| 3' | 66.28 | 2.49 |
| 4' | 29.14 | 1.71 |
|    |       | 1.27 |
| 5' | 69.19 | 3.56 |
| 6' | 21.83 | 1.27 (3) |
| 7' | 40.80 | 2.33 (3) |
| 8' | 40.80 | 2.33 (3) |
| 1" | 95.16 | 5.14 |
| 2" | 35.21 | 2.42 |
|    |       | 1.63 |
| 3" | 73.46 | — |
| 4" | 78.58 | 3.08 |
| 5" | 65.95 | 4.12 |
| 6" | 18.60 | 1.36 (3) |
| 7" | 49.90 | 3.39 (3) |
| 8" | 22.07 | 1.29 (3) |

EXAMPLE 4

Compound of formula 17 wherein $R^9$ is Me

The compound of formula 17, obtained from Example 3, is dissolved in chloroform. 37% formaldehyde (3.0 equiv.) and formic acid (3.0 equiv.) are added and the solution stirred at 45–50° C. for 12–24 hours. The reaction mixture is concentrated under vacuum. The residue is then dissolved in 1–2 mL of methylene chloride. 2–5 mL of a saturated NaHCO$_3$ aqueous solution is then added. The layers are separated and the aqueous re-extracted with an equal volume of methylene chloride. The organics are combined and dried over Na$_2$SO$_4$. Filtration, concentration and isolation yield the title compound as a solid.

EXAMPLE 5

Compound of Formula 23

The compound of formula 14, obtained from Example 4, is dissolved in ethanol. Lithium hydroxide monohydrate (2 equivalents) is added and the reaction mixture stirred overnight at room temperature. The reaction is concentrated under vacuum and partitioned between brine and ethyl acetate. The pH of the reaction mixture is adjusted to 9–10. The reaction mixture is extracted with ethyl acetate and dried over Na$_2$SO$_4$. A 4:1 ratio of Z:E isomers is produced. The crude product is purified by either silica chromatography or crystallization from nitromethane to give the title compound.

EXAMPLE 6

Compound of Formula 24

The compound of formula 23, obtained from Example 5, is dissolved in acetone. A 0.1 M aqueous solution of NaHCO$_3$ (2 equiv.) is added, and the resulting mixture is cooled to 0–5° C. A 0.1 M solution of para-toluenesulfonyl chloride in acetone is added and the mixture stirred overnight. The reaction is worked up by decanting into 25 mL of a 1:1 mixture of methylene chloride and water. The pH of the reaction mixture is adjusted to 9–10 using 1N NaOH. The reaction mixture is extracted with 3×20 mL methylene chloride and dried over Na$_2$SO$_4$. Filtration and concentration of filtrate yields the title compound as a solid product.

EXAMPLE 7

Compound of Formula 26

Method A: The compound of formula 24, obtained from Example 6, is dissolved in glacial acetic acid. Platinum oxide catalyst (50 mole %) is added, and the reaction is flushed with nitrogen, placed under 50 psi hydrogen and shaken at room temperature for 24 hours. Additional platinum oxide catalyst (50 mole %) is added, and the reaction is flushed with nitrogen, placed under 50 psi hydrogen and shaken at room temperature for an additional 24–48 hours. The reaction is worked up by filtration through Celite™. A volume of 25 mL of water is added, and the pH of the reaction mixture is adjusted to 9–10 using 1 N NaOH. The reaction mixture is extracted with 3×25 mL methylene chloride and dried over Na$_2$SO$_4$. Filtration and concentration yields the title compound as a solid product.

Method B: The compound of formula 24 is dissolved in 0.5 mL MeOH and cooled to 0–5° C. NaBH$_4$ (10 equiv.) is added, and the reaction is stirred for 4 hours at 0–5° C., warmed to room temperature and stirred overnight. The reaction is worked up by decanting into 10 mL of a 1:1 mixture of methylene chloride and water. The pH of the reaction mixture is adjusted to 8–9 using 1N NaOH, extracted with 3×5 mL methylene chloride and dried over Na$_2$SO$_4$. Filtration and concentration yields the title compound as a solid product.

EXAMPLE 8

Compound of Formula 27 wherein R$^9$ is Me

The compound of formula 26, obtained from Example 7, is dissolved in chloroform. 37% formaldehyde (1.0 equiv.) and formic acid (1.0 equiv.) is added and the solution stirred at 45–50° C. for 48–72 hours. The reaction mixture is then decanted into a 1:1 mixture of chloroform and water. The pH of the reaction mixture is adjusted to 9–10 using 1N NaOH, and the reaction mixture is extracted with chloroform and dried over Na$_2$SO$_4$. Filtration and concentration yields the title compound as a solid product.

While we have described a number of embodiments of this invention, it is apparent that our basic constructions may be altered to provide other embodiments that utilize the products and processes of this invention. Therefore, it will be appreciated that the scope of this invention is to be defined by the appended claims, rather than by the specific embodiments that have been presented by way of example.

What is claimed is:

1. A compound of formula 1

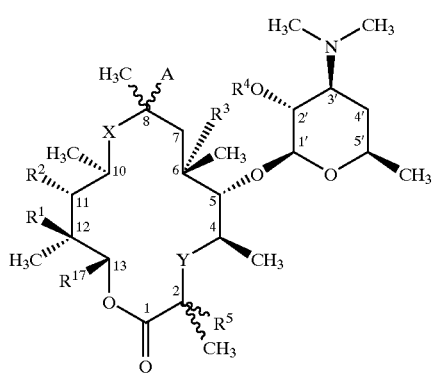

or a pharmaceutically acceptable salt, prodrug or solvate thereof, wherein:

A is H or halogen;

X is selected from —C(O)—, —CH(NR$^8$R$^9$)—, —CHR$^8$NR$^9$—, —NR$^9$CHR$^8$—, —C(=NR$^8$)— and —C(=N—OR$^8$)—, wherein the first dash of each of the foregoing X groups is attached to the C-10 carbon of the compound of formula 1 and the last dash of each group is attached to the C-8 carbon of the compound of formula 1;

Y is selected from CH$_2$, C(O), CHF, CF$_2$, C=C(R$^a$R$^b$), CHSR$^7$, CHR$^7$, C=S, —C(=NR$^8$)—, —C(=N—OR$^8$), CH(OR$^8$), CH(OC(O)R$^8$), CH(OC(O)Ar), CH(OC(O)NR$^8$R$^9$), CH(O(CR$^a$R$^b$)$_n$Ar), CH(OC(O)(CR$^a$R$^b$)$_n$Ar), CH(OC(O)(CR$^a$R$^b$)$_n$NR$^8$(CR$^a$R$^b$)$_n$Ar), CH(OC(O)NR$^8$NR$^8$R$^9$), CH(OC(O)NR$^8$(CR$^a$R$^b$)$_n$NR$^8$(CR$^a$R$^b$)$_n$Ar), CH(OC(O)NR$^8$NR$^8$(CR$^a$R$^b$)$_n$NR$^8$(CR$^a$R$^b$)$_n$Ar), —CH(NR$^8$R$^9$)—, CH(NR$^8$C(O)R$^8$), CH(NR$^8$C(O)NR$^8$R$^9$), CH(NR$^8$C(O)OR$^8$), CH(S(CR$^a$R$^b$)$_n$Ar), —CH(NH(CR$^a$R$^b$)$_n$NR$^8$(CR$^a$R$^b$)$_n$Ar) and CH(NH(CR$^a$R$^b$)$_n$Ar), wherein n is an integer ranging from 0 to 10;

or Y has the following structure:

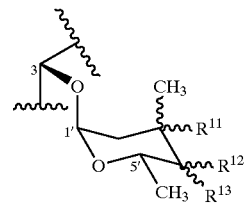

each of R$^a$ and R$^b$ is independently selected from H, halo and a C$_1$–C$_6$ alkyl; R$^a$ and R$^b$ together with the carbon to which they are attached can form a 3- to 10-membered cyclic or heterocydic diradical, wherein one or two carbons of said diradical are optionally replaced by a diradical independently selected from —O—, —S—, —S(O)—, —S(O)$_2$—, a —N(C$_1$-C$_6$) alkyl- and —C(O)— and are optionally substituted by 1 to 3 substituents independently selected from the group S substituents;

(CR$^a$R$^b$)$_n$ is alkylene, wherein n is an integer ranging from 0 to 10, uninterrupted or interrupted by a diradical independently selected from —O—, —S—, —S(O)—, —S(O)$_2$—, a —N(C$_6$)alkyl- and —C(O)— and optionally substituted by 1 to 3 substituents independently selected from the group S substituents;

R$^1$ and R$^2$ taken with the intervening atoms form an additional ring having one of the following structures:

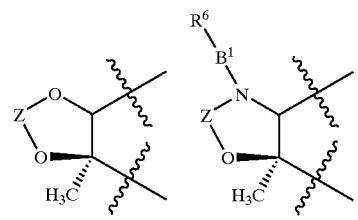

wherein Z is CH$_2$ or C(=O); B$^1$ is selected from NH, NMe and CH$_2$; and R$^6$ is (CH$_2$)$_n$Ar$^1$, wherein n is an integer ranging from 0 to 10 and Ar$^1$ is selected from quinolin-4-yl, 4-phenyl-imidazol-1-yl, imidazo(4,5-b)pyridin-3-yl and 4-pyridin-3-yl-imidazol-1-yl;

R$^3$ is OR$^{10}$;

R$^3$ and X can be taken together;

when taken together, R$^3$ and X taken with the intervening atoms form an additional ring having one of the following structures:

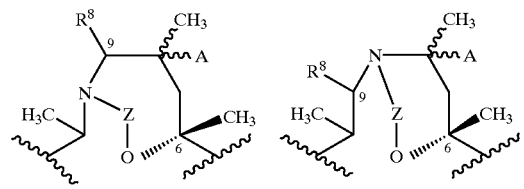

R$^3$ and Y can be taken together;

when taken together, R$^3$ and Y taken with the intervening atoms form an additional ring having one of the following structures:

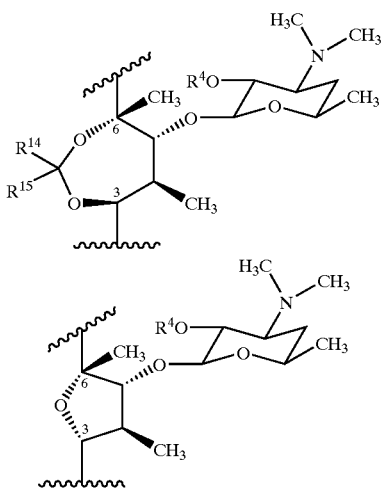

$R^4$ is selected from H, a $C(O)(C_1-C_{18})$alkyl, $C(O)Ar$, a $OC(O)(C_1-C_{18})$alkyl and $OC(O)Ar$, wherein the alkyl moieties of the foregoing $R^4$ groups are optionally replaced by a diradical independently selected from —O—, —S—, —S(O)—, —S(O)$_2$—, a —N(C$_1$–C$_6$)alkyl- and —C(O)— and are optionally substituted by 1 to 3 substituents independently selected from the group S substituents;

$R^5$ is selected from H, halo, a $C_1-C_{10}$ alkyl, a $C_3-C_{10}$ alkenyl, a $C_3-C_{10}$ alkynyl, —C(R$^a$R$^b$)—C(R$^a$)═C (R$^b$)—Ar, (CR$^a$R$^b$)$_n$Ar, OR$^8$, O(CO)R$^8$, OC(O)NR$^8$R$^9$, NR$^8$R$^9$, NR$^8$C(O)R$^8$ NR$^8$C(O)NR$^8$R$^9$, O(CR$^a$R$^b$)$_n$Ar, S(CR$^a$R$^b$)$_n$Ar and NR$^8$(CR$^a$R$^b$)$_n$Ar, wherein n is an integer ranging from 0 to 10, wherein one or two carbons of said alkyl, alkenyl and alkynyl are optionally replaced by a diradical independently selected from —O—, —S—, —S(O)—, —S(O)$_2$—, a —N(C$_1$–C$_6$)alkyl- and —C(O)— and are optionally substituted by 1 to 3 substituents independently selected from the group S substituents;

$R^5$ Y can be taken together;

when taken together, $R^5$ and Y taken with the intervening atoms form the following structure:

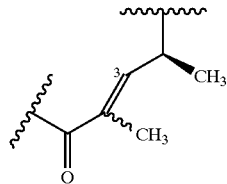

each of $R^7$, $R^8$ and $R^9$ is independently selected from H and a $C_1-C_{12}$ alkyl, wherein one or two carbons of said alkyl are optionally replaced by a diradical independently selected from —O—, —S—, —S(O)—, —S(O)$_2$—, a —N(C$_1$–C$_6$) alkyl- and —C(O)— and are optionally substituted by 1 to 3 substituents independently selected from the group S substituents;

$R^8$ and $R^9$ together with the nitrogen to which they are attached can form a 3- to 10-membered ring, in which one or two carbons are optionally replaced by a diradical independently selected from —O—, —S—, —S(O)—, —S(O)$_2$—, a —N(C$_1$–C$_6$) alkyl- and —C(O)— and are optionally substituted by 1 to 3 substituents independently selected from the group S substituents;

$R^{10}$ is selected from a $C_1-C_{10}$ alkyl, a $C_3-C_{10}$ alkenyl, a $C_3-C_{10}$ alkynyl, —C(R$^a$R$^b$)— C(R$^a$)═C(R$^b$)—Ar and (CR$^a$R$^b$)$_n$Ar, wherein n is an integer ranging from 1 to 10, wherein one or two carbons of said alkyl, alkenyl and alkynyl are optionally replaced by a diradical independently selected from —O—, —S—, —S(O)—, —S(O)$_2$—, a —N(C$_1$–C$_6$)alkyl- and —C(O)— and are optionally substituted by 1 to 3 substituents independently selected from the group S substituents, provided that $R^{10}$ not unsubstituted methyl;

$R^{11}$ is H or OCH$_3$;

$R^{12}$ and $R^{13}$ together with the carbon to which they are attached can form —C(O)—, —C(═NR$^8$)— or —C(═N—OR$^8$);

$R^{12}$ and $R^{13}$ together with the carbon to which they are attached can form a 3- to 10-membered ring, wherein one or two carbons of said ring are optionally replaced by a diradical independently selected from —O—, —S—, —S(O)—, —S(O)$_2$—, a —N(C$_1$–C$_6$)alkyl- and —C(O)— and are optionally substituted by 1 to 3 substituents independently selected from the group S substituents;

$R^{12}$ is selected from H, a $C_1-C_{10}$ alkyl, a $C_3-C_{10}$ alkenyl, a $C_3-C_{10}$ alkynyl, —C(R$^a$R$^b$)— C(R$^a$)═C(R$^b$)—Ar and (CR$^a$R$^b$)$_n$Ar, wherein n is an integer ranging from 0 to 10, wherein one or two carbons of said alkyl, alkenyl and alkynyl are optionally replaced by a diradical independently selected from —O—, —S—, —S(O)—, —S(O)$_2$—, a —N(C$_1$–C$_6$)alkyl- and —C(O)— and are optionally substituted by 1 to 3 substituents independently selected from the group S substituents;

$R^{13}$ is selected from H, a $C_1-C_{10}$ alkyl, a $C_3-C_{10}$ alkenyl, a $C_3-C_{10}$ alkynyl, OR$^8$, OC(O)R$^8$, OC(O)(CR$^a$R$^b$)$_n$Ar, OC(O)(CR$^a$R$^b$)$_n$NR$^8$(CR$^a$R$^b$)$_n$Ar, OC(O)NR$^8$R$^9$, OC(O)NR$^8$NR$^8$R$^9$, OC(O)NR$^8$(CR$^a$R$^b$)$_n$NR$^8$(CR$^a$R$^b$)$_n$ Ar, OC(O)NR$^8$NR$^8$(CR$^a$R$^b$)$_n$NR$^8$(CR$^a$R$^b$)$_n$Ar, NR$^8$R$^9$, NR$^8$(CO)R$^8$, NR$^8$C(O)NR$^8$R$^9$, NR$^8$C(O)OR$^8$, O(CR$^a$R$^b$)$_n$Ar, O(CR$^a$R$^b$)$_n$NR$^8$(CR$^a$R$^b$)$_n$Ar, S(CR$^a$R$^b$)$_n$ Ar, NH(CR$^a$R$^b$)$_n$NR$^8$(CR$^a$R$^b$)$_n$Ar and NH(CR$^a$R$^b$)$_n$ Ar, wherein n is an integer ranging from 0 to 10;

each of $R^{14}$ and $R^{15}$ is independently selected from H, a $C_1-C_{12}$ alkyl, an aryl-substituted $C_1-C_{12}$ alkyl and a heteroaryl-substituted $C_1-C_{12}$ alkyl, wherein one or two carbons of said alkyl are optionally replaced by a diradical independently selected from —O—, —S—, —S(O)—, —S(O)$_2$—, a —N(C$_1$–C$_6$) alkyl- and —C(O)— and are optionally substituted by 1 to 3 substituents independently selected from the group S substituents;

$R^4$ and $R^{15}$ together with the carbon to which they are attached can form a 3- to 10-membered ring, in which one or two carbons are optionally replaced by a diradical independently selected from —O—, —S—, —S(O)—, —S(O)$_2$—, a —N(C$_1$–C$_6$)alkyl- and —C(O)— and are optionally substituted by 1 to 3 substituents independently selected from the group S substituents;

$R^{17}$ is a $C_1-C_{20}$ alkcyl, wherein one or two carbons of said alkyl is/are optionally replaced by a diradical independently selected from —O—, —S—, —S(O)—, —S(O)$_2$—, a —N(C$_1$–C$_6$)alkyl- and —C(O)— and one or two carbons of said alkyl is/are optionally substituted by 1 to 3 substituents independently selected from the group S substituents, provided that $R^{17}$ is not unsubstituted ethyl;

$R^{18}$ is selected from the group consisting of an aryl, a substituted aryl, a heteroaryl, a substituted heteroaryl and a heterocycloalkyl;

each of $R^{19}$ and $R^{20}$ independently selected from the group consisting of a $C_1$–$C_{12}$ alkenyl, a $C_1$–$C_{12}$ alkynyl, an aryl, a $C_3$–$C_8$ cycloalkyl, a heterocycloalkcyl and a heteroaryl, wherein said alkenyl, alkynyl, aryl, cycloalkyl, heterocycloalkyl and heteroaryl are substituted or unsubstituted;

$R^{19}$ and $R^{20}$ together with the carbon to which they are attached can form a 3- to 10-membered heterocycloalkyl ring that may be substituted with one or more substituents independently selected from the group consisting of halogen, hydroxy, a $C_1$–$C_3$ alkcoxy, a $C_1$–$C_3$ alkoxy-$C_1$–$C_3$ alkoxy, oxo, a $C_1$–$C_3$ alkyl, a halo-$C_1$–$C_3$ alkyl and a $C_1$–$C_3$ alkoxy-$C_1$–$C_3$ alkyl;

each Ar is independently a 4- to 10-membered heterocyclic or a $C_6$–$C_{10}$ aryl, wherein said heterocyclic and aryl groups are optionally substituted by one or more substituents independently selected from the group S substituents; and the group S substituents are selected from the group consisting of:
nitro, halogens, hydroxy, $N_3$, CN, CHO, $C_1$–$C_{10}$ alkoxy, $C_1$–$C_3$ alkoxy-$C_1$–$C_3$ alkoxy, oxo, $C_1$–$C_{10}$ alkanoyl, $C_1$–$C_{10}$ alkyl, $C_1$–$C_{12}$ alkyl substituted with an aromatic heterocyclic, $C_1$–$C_6$ alkyl substituted with O—$SO_2$, $C_2$–$C_{10}$ alkenyl, $C_2$–$C_{10}$ alkynyl, $C_3$–$C_{10}$ cycloalkyl, substituted $C_3$–$C_{10}$ cycloalkyl, 4 to 10 membered heterocyclic, substituted heterocyclic, aryl, substituted aryl, trialkylsilyl, —C(O)$R^8$, —C(O)$R^{18}$, —C(O)O$R^8$, —C(O)N$R^8R^9$, —N$R^8R^9$, —N$R^{19}R^{20}$, —NHC(O)$R^8$, —NHC(O)N$R^8R^9$, =N—O—$R^8$, =N—N$R^8R^9$, =N—N$R^{19}R^{20}$, =N—$R^8$, =N—$R^{18}$, =N—NHC(O)$R^8$, =N—NHC(O)N$R^8R^9$, —C≡N, —S(O)$_n$, wherein n is 0, 1 or 2, —S(O)$_nR^8$, wherein n is 0, 1 or 2, —O—S(O)$_nR^8$, wherein n is 0, 1 or 2, and —$SO_2NR^8R^9$.

2. A compound of formula 1:

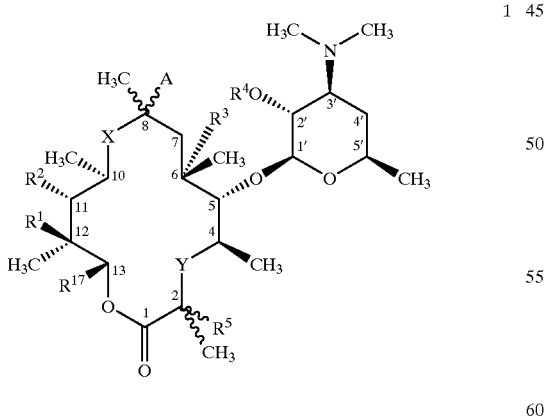

1 or a pharmaceutically acceptable salt, prodrug or solvate thereof, wherein:

A is H or halogen;

X is selected from —C(O)—, —CH(N$R^8R^9$)—, —CH$R^8NR^9$—, —$NR^9CHR^8$—, —C(=$NR^8$)— and —C(=N—O$R^8$)—, wherein the first dash of each of the foregoing X groups is attached to the C-10 carbon of the compound of formula 1 and the last dash of each group is attached to the C-8 carbon of the compound of formula 1;

Y is selected from $CH_2$, C(O), C=S, CH(O$R^8$), CH(OC(O)$R^8$), CH(OC(O)Ar), CH(OC(O)N$R^8R^9$) and CH(O(C$R^aR^b$)$_n$Ar), wherein n is an integer ranging from 0 to 10;

$R^1$ and $R^2$ can be taken separately or together;

when taken separately, $R^1$ is independently selected from O$R^8$, OC(O)$R^8$, OC(O)N$R^8R^9$, N$R^8R^9$, $NR^8$C(O)$R^8$, $NR^8$C(O)N$R^8R^9$, O(C$R^aR^b$)$_n$Ar, S(C$R^aR^b$)$_n$Ar and N(C$R^aR^b$)$_n$Ar, wherein n is an integer ranging from 0 to 10;

when taken separately, $R^2$ is independently selected from O$R^8$, O-mesyl, O-tosyl, OC(O)$R^8$, OC(O)N$R^8R^9$, N$R^8R^9$, $NR^8$C(O)$R^8$, $NR^8$C(O)N$R^8R^9$, O(C$R^aR^b$)$_n$Ar, S(C$R^aR^b$)$_n$Ar and NH(C$R^aR^b$)$_n$Ar, wherein n is an integer ranging from 0 to 10; each of $R^a$ and $R^b$ is independently selected from H, halo and a $C_1$–$C_6$ alkyl;

$R^a$ and $R^b$ together with the carbon to which they are attached can form a 3- to 10-membered cyclic or heterocyclic diradical, wherein one or two carbons of said diradical are optionally replaced by a diradical independently selected from —O—, —S—, —S(O)—, —S(O)$_2$—, a —N($C_1$–$C_6$)alkyl- and —C(O)— and are optionally substituted by 1 to 3 substituents independently selected from the group S substituents;

(C$R^aR^b$)$_n$ is alkylene, wherein n is an integer ranging from 0 to 10, uninterrupted or interrupted by a diradical independently selected from —O—, —S—, —S(O)—, —S(O)$_2$—, a —N($C_1$–$C_6$)alkyl- and —C(O)— and optionally substituted by 1 to 3 substituents independently selected from the group S substituents;

when taken together, $R^1$ and $R^2$ taken with the intervening atoms form an additional ring having one of the following structures:

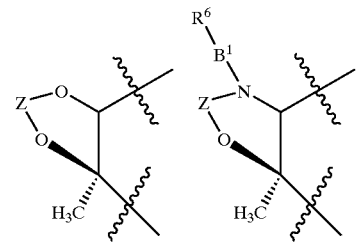

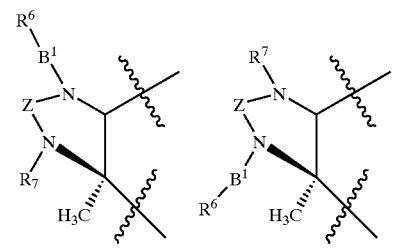

-continued

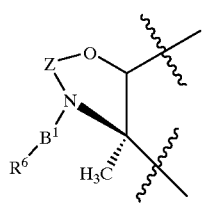

B¹ is selected from O, $(CR^{aa}R^{bb})_m$, $SO_2$, O and $NR^7$, wherein m is 0 or 1;

Z is selected from $(CR^{aa}R^{bb})_m$, C(O), C($NR^{aa}$), P—$OR^{aa}$, P(O)$OR^{aa}$, P(O)$NR^{aa}R^{bb}$, Si($R^cR^d$), SO, $SO_2$, $(CR^{aa}R^{bb})_m$CO and CO($(CR^{aa}R^{bb}))_m$, wherein m is 1 or 2;

$R^c$ and $R^d$ are independently selected from a $C_1$–$C_8$ alkyl, a $C_6$–$C_{10}$ aryl and a $C_4$–$C_{10}$ heterocyclic;

$R^{aa}$ and $R^{bb}$ are independently selected from H and a $C_1$–$C_6$ alkyl;

$R^{aa}$ and $R^{bb}$ together with the carbon to which they are attached can form a 3- to 10-membered cyclic or heterocyclic diradical, wherein one or two carbons of said diradical are optionally replaced by a diradical independently selected from —O—, —S—, —S(O)—, —S(O)$_2$—, a —N($C_1$-$C_6$)alkyl- and —C(O)— and are optionally substituted by 1 to 3 substituents independently selected from the group S substituents;

when B¹ is $NR^7$, B¹ and $R^6$ together with the nitrogen to which they are attached can form a 3- to 10-membered ring wherein one or two carbons of said ring are optionally replaced by a diradical independently selected from —O—, —S—, —S(O)—, —S(O)$_2$—, a —N($C_1$-$C_6$) alkyl- and —C(O)— and are optionally substituted by 1 to 3 substituents independently selected from the group S substituents;

when B¹ is $NR^7$, B¹ and $R^6$ together with the nitrogen to which they are attached can form —N=C($R^7$)($R^aR^b$)$_n$Ar, wherein n is an integer ranging from 0 to 10;

$R^1$, $R^2$ and X can be taken together;

when taken together, $R^1$, $R^2$ and X taken with the intervening atoms form an additional two rings having one of the following structures:

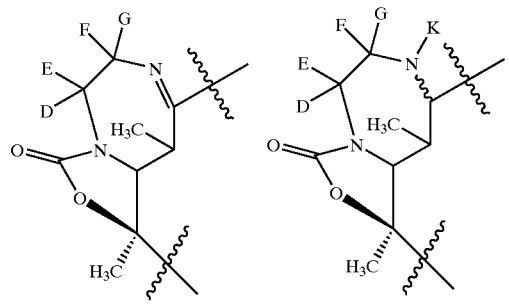

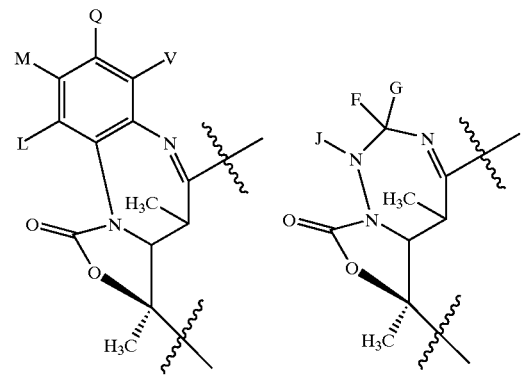

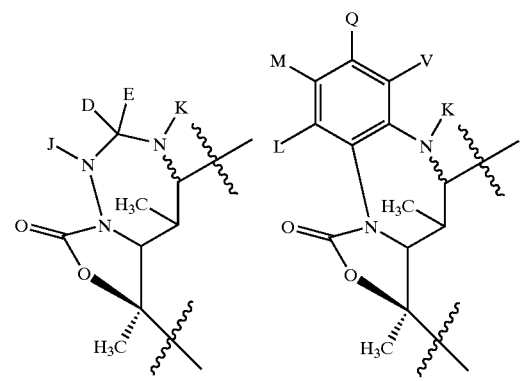

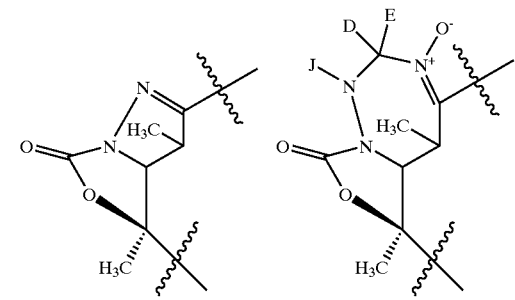

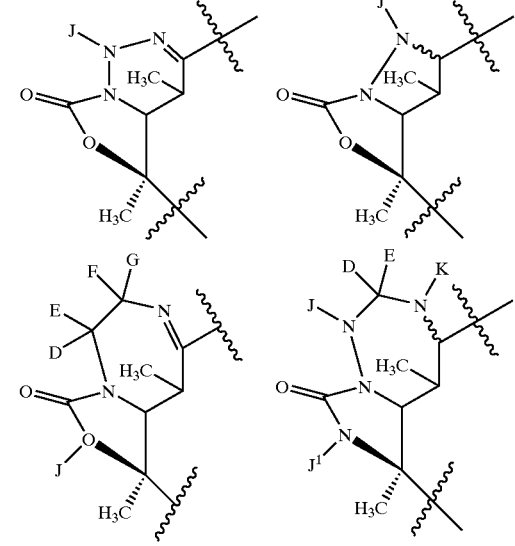

each of D, E, F and G is independently selected from H, halo, a $C_1$–$C_{12}$ alkyl, a $C_3$–$C_{10}$ alkenyl, a $C_3$–$C_{10}$ alkynyl and $CH_2(R^aR^b)_nAr$, wherein n is an integer ranging from 0 to 10, wherein one or two carbons of said alkyl are optionally replaced by a diradical independently selected from —O—, —S—, —S(O)—, —S(O)$_2$—, a —N($C_1$–$C_6$)alkyl- and —C(O)— and are optionally substituted by 1 to 3 substituents independently selected from the group S substituents;

D and E or F and G together with the carbon to which they are attached can form a 3- to 10-membered cyclic or heterocyclic diradical, wherein one or two carbons of said diradical are optionally replaced by a diradical independently selected from —O—, —S—, —S(O)—, —S(O)$_2$—, a —N($C_1$–$C_6$)alkyl- and —C(O)— and are optionally substituted by 1 to 3 substituents independently selected from the group S substituents;

Each of J, $J^1$ and K is independently selected from $C(O)R^8$, $C(O)NR^8R^9$, $C(O)OR^8$, $(CR^aR^b)_nAr$, $S(CR^aR^b)_nAr$ and $NH(CR^aR^b)_nAr$; wherein n is an integer ranging from 0 to 10; each of L, M, Q and V is independently selected from the group S substituents; one or two carbons of the phenyl ring in which L, M, Q and V are attached can be replaced with nitrogen;

$R^1$ and X can be taken together;

when taken together, $R^1$ and X taken with the intervening atoms form an additional ring having one of the following structures:

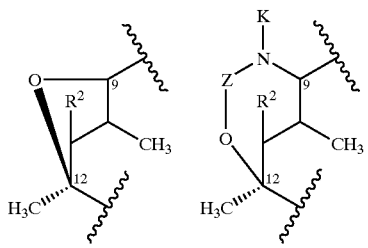

$R^2$ and X can be taken together;

when taken together, $R^2$ and X taken with the intervening atoms form an additional ring having one of the following structures:

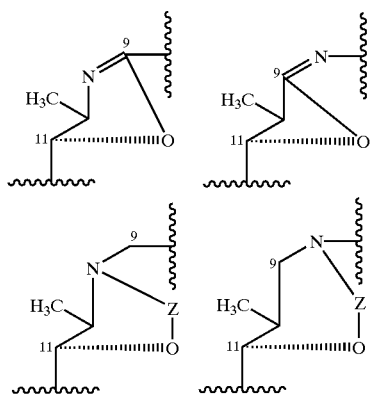

$R^3$ is $OR^{10}$;

$R^3$ and X can be taken together;

when taken together, $R^3$ and X taken with the intervening atoms form an additional ring having one of the following structures:

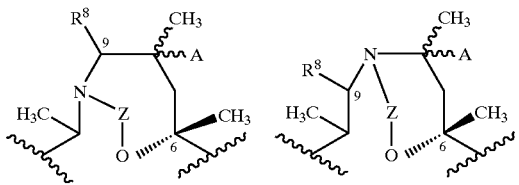

$R^4$ is selected from H, a $C(O)(C_1$–$C_{18})$alkyl, C(O)Ar, a $OC(O)(C_1$–$C_{18})$alkyl and OC(O)Ar, wherein the alkyl moieties of the foregoing $R^4$ groups are optionally replaced by a diradical independently selected from —O—, —S—, —S(O)—, —S(O)$_2$—, a —N($C_1$–$C_6$) alkyl- and —C(O)— and are optionally substituted by 1 to 3 substituents independently selected from the group S substituents;

$R^5$ is selected from H, halo, a $C_1$–$C_{10}$ alkyl, a $C_3$–$C_{10}$ alkenyl, a $C_3$–$C_{10}$ alkynyl, —C($R^aR^b$)—C($R^a$)=C($R^b$)—Ar, $(CR^aR^b)_nAr$, $OR^8$, $O(CO)R^8$, $OC(O)NR^8R^9$, $NR^8R^9$, $NR^8C(O)R^8$, $NR^8C(O)NR^8R^9$, $O(CR^aR^b)_nAr$, $S(CR^aR^b)_nAr$ and $NR^8(CR^aR^b)_nAr$, wherein n is an integer ranging from 0 to 10, wherein one or two carbons of said alkyl, alkenyl and alkynyl are optionally replaced by a diradical independently selected from —O—, —S—, —S(O)—, —S(O)$_2$—, a —N($C_1$–$C_6$)alkyl- and —C(O)— and are optionally substituted by 1 to 3 substituents independently selected from the group S substituents;

$R^6$ is selected from H, a $C_1$–$C_{12}$ alkyl, a $C_3$–$C_{10}$ alkenyl, a $C_3$–$C_{10}$ alkynyl and $CH_2(R^aR^b)_nAr$, wherein n is an integer ranging from 0 to 10, wherein one or two carbons of said alkyl are optionally replaced by a diradical independently selected from —O—, —S—, —S(O)—, —S(O)$_2$—, a —N($C_1$–$C_6$)alkyl- and —C(O)— and are optionally substituted by 1 to 3 substituents independently selected from the group S substituents;

each of $R^7$, $R^8$ and $R^9$ is independently selected from H and a $C_1$–$C_{12}$ alkyl, wherein one or two carbons of said alkyl are optionally replaced by a diradical independently selected from —O—, —S—, —S(O)—, —S(O)$_2$—, a —N($C_1$ –$C_6$) alkyl- and —C(O)— and are optionally substituted by 1 to 3 substituents independently selected from the group S substituents;

$R^8$ $R^9$ together with the nitrogen to which they are attached can form a 3- to 10-membered ring, in which one or two carbons are optionally replaced by a diradical independently selected from —O—, —S—, —S(O)—, —S(O)$_2$—, a —N($C_1$–$C_6$) alkyl- and —C(O)— and are optionally substituted by 1 to 3 substituents independently selected from the group S substituents;

$R^{10}$ is selected from a $C_1$–$C_{10}$ alkyl, a $C_3$–$C_{10}$ alkenyl, a $C_3C_{10}$ alkynyl, —C($R^aR^b$)— C($R^a$)=C($R^b$)—Ar and $(CR^aR^b)_nAr$, wherein n is an integer ranging from 1 to 10, wherein one or two carbons of said alkyl, alkenyl and alkynyl are optionally replaced by a diradical independently selected from —O—, —S—, —S(O)—, —S(O)$_2$—, a —N($C_1$–$C_6$)alkyl- and —C(O)— and are optionally substituted by 1 to 3 substituents independently selected from the group S substituents, provided that $R^{10}$ not unsubstituted methyl;

$R^{17}$ is methyl;

$R^{18}$ is selected from the group consisting of an aryl, a substituted aryl, a heteroaryl, a substituted heteroaryl and a heterocycloalkyl;

each of $R^{19}$ and $R^{20}$ is independently selected from the group consisting of a $C_1-C_{12}$ alkenyl, a $C_1-C_{12}$ alkynyl, an aryl, a $C_3-C_8$ cycloalkyl, a heterocycloalkyl and a heteroaryl, wherein said alkenyl, alkynyl, aryl, cycloalkyl, heterocycloalkyl and heteroaryl are substituted or unsubstituted;

$R^{19}$ and $R^{20}$ together with the carbon to which they are attached can form a 3- to 10-membered heterocycloalkyl ring that may be substituted with one or more substituents independently selected from the group consisting of halogen, hydroxy, a $C_1-C_3$ alkoxy, a $C_1-C_3$ alkoxy-$C_1-C_3$ alkoxy, oxo, a $C_1-C_3$ alkyl, a halo-$C_1-C_3$ alkyl and a $C_1-C_3$ alkoxy-$C_1-C_3$ alkyl;

each Ar is independently a 4- to 10-membered heterocyclic or a $C_6-C_{10}$ aryl, wherein said heterocyclic and aryl groups are optionally substituted by one or more substituents independently selected from the group S substituents; and the group S substituents are selected from the group consisting of:

nitro, halogens, hydroxy, $N_3$, CN, CHO, $C_1-C_{10}$ alkoxy, $C_1-C_3$ alkoxy-$C_1-C_3$ alkoxy, oxo, $C_1-C_{10}$ alkanoyl, $C_1-C_{10}$ alkyl, $C_1-C_{12}$ alkyl substituted with an aromatic heterocyclic, $C_1-C_6$ alkyl substituted with O—$SO_2$, $C_2C_{10}$ alkenyl, $C_2-C_{10}$ alkynyl, $C_3-C_{10}$ cycloalkyl, substituted $C_3-C_{10}$ cycloalkyl, 4 to 10 membered heterocyclic, substituted heterocyclic, aryl, substituted aryl, trialkylsilyl, —C(O)$R^8$, —C(O)$R^{18}$, —C(O)O$R^8$, —C(O)N$R^8R^9$, —N$R^8R^9$, —N$R^{19}R^{20}$, —NHC(O)$R^8$, —NHC(O)N$R^8R^9$, =N—O—$R^8$, =N—N$R^8R^9$, =N—N$R^{19}R^{20}$, =N—$R^8$, =N—$R^{18}$, =N—NHC(O)$R^8$, =N—NHC(O)N$R^8R^9$, —C≡N, —S(O)$_n$, wherein n is 0, 1 or 2, —S(O)$_nR^8$, wherein n is 0, 1 or 2, —O—S(O)$_nR^8$, wherein n is 0, 1 or 2, and —SO$_2$N$R^9$.

3. The compound of claim 1, having the following formula:

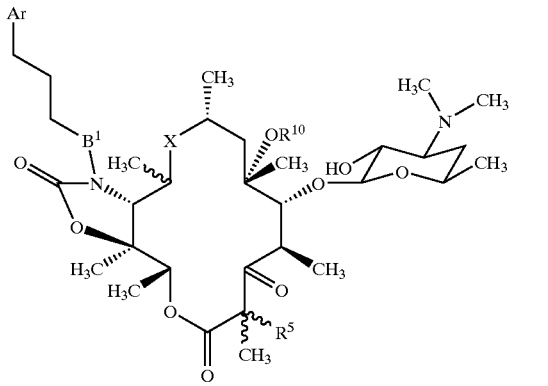

wherein $B^1$ is selected from NH, O and CH$_2$;

X is selected from —C(O)—, —CH$_2$NH—, —CH$_2$NMe—, —NHCH$_2$—, —N(Me)CH$_2$—, —CH(NH$_2$)—, —C(=N—OMe)— and —C(=N—OCH$_2$O(CH$_2$)$_2$OMe)—;

$R_5$ is H or F; and

Ar is selected from quinolin-4-yl, 7-methoxy-quinolin-4-yl, 4-phenyl-imidazoi-1-yl, pyridin-4-yl, pyridin-3-yl, pyridin-2-yl, 4-pyridin-3-yl-imidazol-1-yl, phenyl, imidazo(4,5-b)pyridin-3-yl, 2-phenyl-thiazol-5-yl, 2-pyridin-3-yl-thiazol-4-yl and benzoimidazol-1-yl.

4. The compound of claim 2, wherein said compound has the following formula:

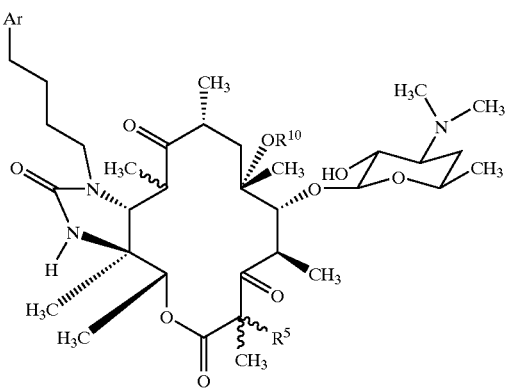

wherein

Ar is selected from quinolin-4-yl, 7-methoxy-quinolin-4-yl, 4-phenyl-imidazol-1-yl, pyridin-4-yl, pyridin-3-yl, pyridin-2-yl, 4-pyridin-3-yl-imidazol-1-yl, phenyl, imidazo(4,5-b)pyridin-3-yl, 2-phenyl-thiazol-5-yl, 2-pyridin-3-yl-thiazol-4-yl and benzoimidazol-1 -yl; and $R^5$ is H or F.

5. A compound selected from the group consisting of:

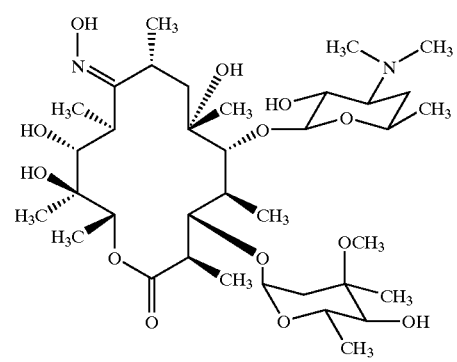

14

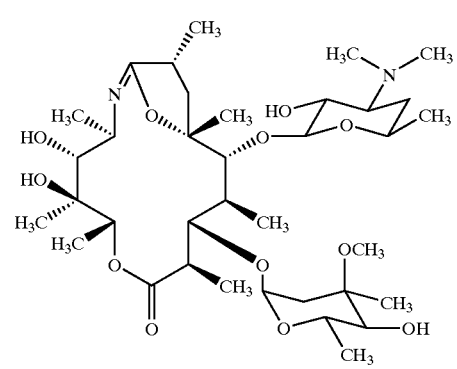

15

17
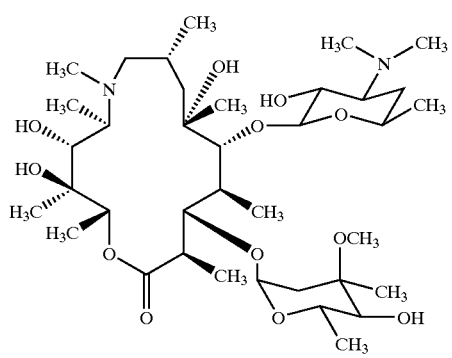
16
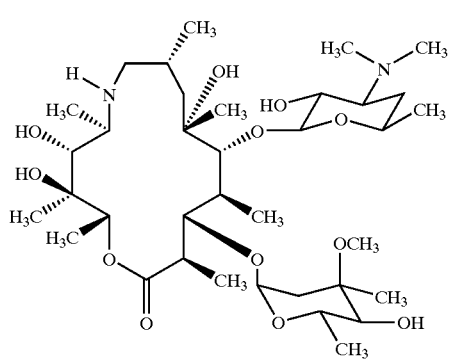
23
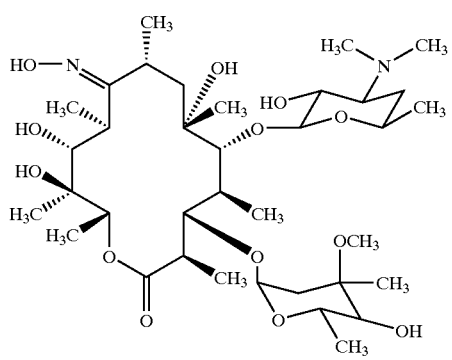
24
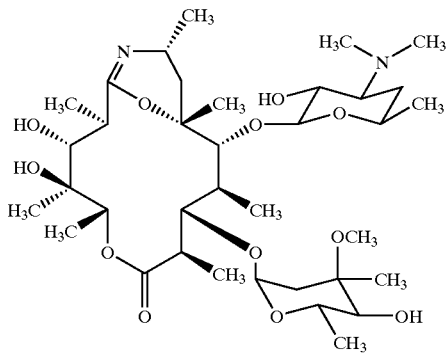
26
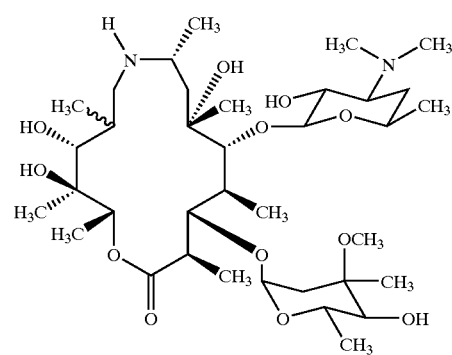
and
27
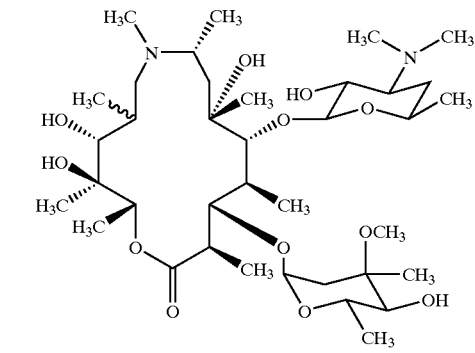
and the pharmaceutically acceptable salts, prodrugs, and solvates of the above compounds.
* * * * *